(12) United States Patent
Rubinstein et al.

(10) Patent No.: US 8,071,391 B2
(45) Date of Patent: Dec. 6, 2011

(54) METHOD AND APPARATUS FOR DETECTING AND QUANTIFYING A CHEMICAL SUBSTANCE EMPLOYING AN OPTICAL TRANSMISSION PROPERTY OF METALLIC ISLANDS ON A TRANSPARENT SUBSTRATE

(75) Inventors: Israel Rubinstein, Rehovot (IL); Alexander Vaskevich, Rehovot (IL); Gregory Kalyuzhny, Rehovot (IL)

(73) Assignee: Yeda Research and Development Company Ltd., Rehovot (IL)

( * ) Notice: Subject to any disclaimer, the term of this patent is extended or adjusted under 35 U.S.C. 154(b) by 196 days.

(21) Appl. No.: 09/922,220

(22) Filed: Aug. 3, 2001

(65) Prior Publication Data
US 2002/0160522 A1      Oct. 31, 2002

Related U.S. Application Data

(60) Provisional application No. 60/271,620, filed on Feb. 26, 2001.

(51) Int. Cl.
*G01N 33/553* (2006.01)
(52) U.S. Cl. ..... 436/171; 436/518; 436/525; 422/82.05; 422/82.11; 356/301; 356/246
(58) Field of Classification Search ............... 422/82.05, 422/82.09, 82.11; 356/234, 246, 301; 436/171, 436/518, 525
See application file for complete search history.

(56) References Cited

U.S. PATENT DOCUMENTS

| | | | |
|---|---|---|---|
| 4,720,633 A | 1/1988 | Nelson | |
| 4,764,343 A | 8/1988 | Nyberg | 422/83 |
| 4,802,761 A * | 2/1989 | Bowen et al. | 356/301 |
| 4,880,976 A | 11/1989 | Mancuso et al. | |
| 5,412,211 A | 5/1995 | Knowles | |
| 5,449,918 A | 9/1995 | Krull et al. | 250/458.1 |
| 5,611,998 A | 3/1997 | Aussenegg et al. | 422/82.05 |

(Continued)

FOREIGN PATENT DOCUMENTS

EP      0 846 946 A2     6/1998

(Continued)

OTHER PUBLICATIONS

Aussenegg F.R. et al: "The metal island coated swelling polymer over mirror systems (MICSPONS): a new principle for measuring ionic strength." Sensors and Acruators B 29(1995) pp. 204-209.

(Continued)

*Primary Examiner* — Lyle Alexander
(74) *Attorney, Agent, or Firm* — Houston Eliseeva, LLP

(57) ABSTRACT

This invention seeks to provide methods and apparatus for analysis. Electromagnetic radiation is transmitted through a plurality of metallic islands on a transparent substrate. A resultant optical property of the plurality of metallic islands is measured. Thereafter a chemical substance is adsorbed onto the plurality of metallic islands so as to produce a chemical substance-metallic islands moiety.

Electromagnetic radiation is transmitted through the chemical substance-metallic islands moiety and a resultant optical property of metallic islands in the chemical substance-metallic islands moiety is measured. The resultant optical property of the metallic islands in chemical substance-metallic islands moiety and the resultant optical property of the plurality of metallic islands are employed so as to provide at least one of a quantitative indication and a qualitative indication of at least one of: the chemical substance-metallic islands moiety, a functionality of the chemical substance-metallic islands moiety, the plurality of metallic islands, a functionality of the plurality of metallic islands, the chemical substance and a functionality of the chemical substance.

36 Claims, 29 Drawing Sheets

U.S. PATENT DOCUMENTS

| | | | | |
|---|---|---|---|---|
| 5,670,978 | A | 9/1997 | Kobayashi et al. | 345/94 |
| 5,715,334 | A | 2/1998 | Peters | 382/254 |
| 5,789,748 | A | 8/1998 | Liu et al. | |
| 5,792,667 | A * | 8/1998 | Florin et al. | 436/147 |
| 5,858,799 | A * | 1/1999 | Yee et al. | 436/164 |
| 5,866,433 | A | 2/1999 | Schalkhammer et al. | 436/525 |
| 5,999,315 | A | 12/1999 | Fukano et al. | 359/492 |
| 6,168,825 | B1 | 1/2001 | O'Brien et al. | 427/160 |
| 6,184,610 | B1 | 2/2001 | Shibata et al. | 313/309 |
| 6,208,422 | B1 | 3/2001 | Naya | 356/445 |
| 6,221,426 | B1 | 4/2001 | Yamanobe | 427/77 |
| 6,459,482 | B1 | 10/2002 | Singh et al. | |
| 6,623,977 | B1 * | 9/2003 | Farquharson et al. | 436/164 |
| 6,728,429 | B1 * | 4/2004 | Melman et al. | 385/12 |

FOREIGN PATENT DOCUMENTS

| | | |
|---|---|---|
| JP | 2000356587 A | 12/2000 |
| WO | 98/09153 A1 | 3/1998 |

OTHER PUBLICATIONS

Schalkhammer Th. et al: "Detection of fluorophore-labelled antibodies by surface-enhanced fluroecence on metal nanoislands." SPIE vol. 2976, pp. 129-136 (1997).

Schalkhammer Th..et al: "The use of metal-island-coated pH-sensitive swelling polymers for biosensor applications." "Sensors and Actuators" B 24-25 (1995) pp. 166-172.

Palkovits R. et al: "Structural behavior of nanometric carbohydrate films transduced by a resonant technique." Biopolymres, vol. 69 pp. 333-342 (2003).

Mayer Ch. et al: "Surface enhanced resonance of metal nano clusters: a novel tool for Proteomics." Journal of Nanoparticle Research 3: pp. 361-371 (Dec. 2001).

Supplemental European Search Report, dated Mar. 10, 2009, from corresponding European Application No. EP 01 95 8330.

Kalyuzhny, G. et al., "Spectroscopic Characterization of self-Assembled Macrocycle Monolayers on Gold", I. Rev. Anal. Chem. 1999, 18, pp. 237-242.

Kalyuzhny, G. et al., "UV/Vis Spectroscopy of Metalloporphyrin and Metallophthalocynanine Monolayers Self-Assembled on Ultrathin Gold Films", I. 2000, J. Phys. Chem. B 104, pp. 8238-8244.

www.cranfield.ac.uk/biotech/spr.htm, 2001.

Charles A. Goss, et al., "Application of (3-Mercaptopropyl) Trimethoxysilane as a Molecular Adhesive in the Fabrication of Vapor-Deposited Gold Electrodes on Glass Substrates", M. Anal. Chem. 1991, 63, pp. 85-88.

Kalyuzhny, G. et al., "Differential Plasmon Spectroscopy as a Tool for Monitoring Molecular Binding to Ultrathin Gold Films", J. Am. Chem. Soc. 2001, 123, pp. 3177-3178.

* cited by examiner

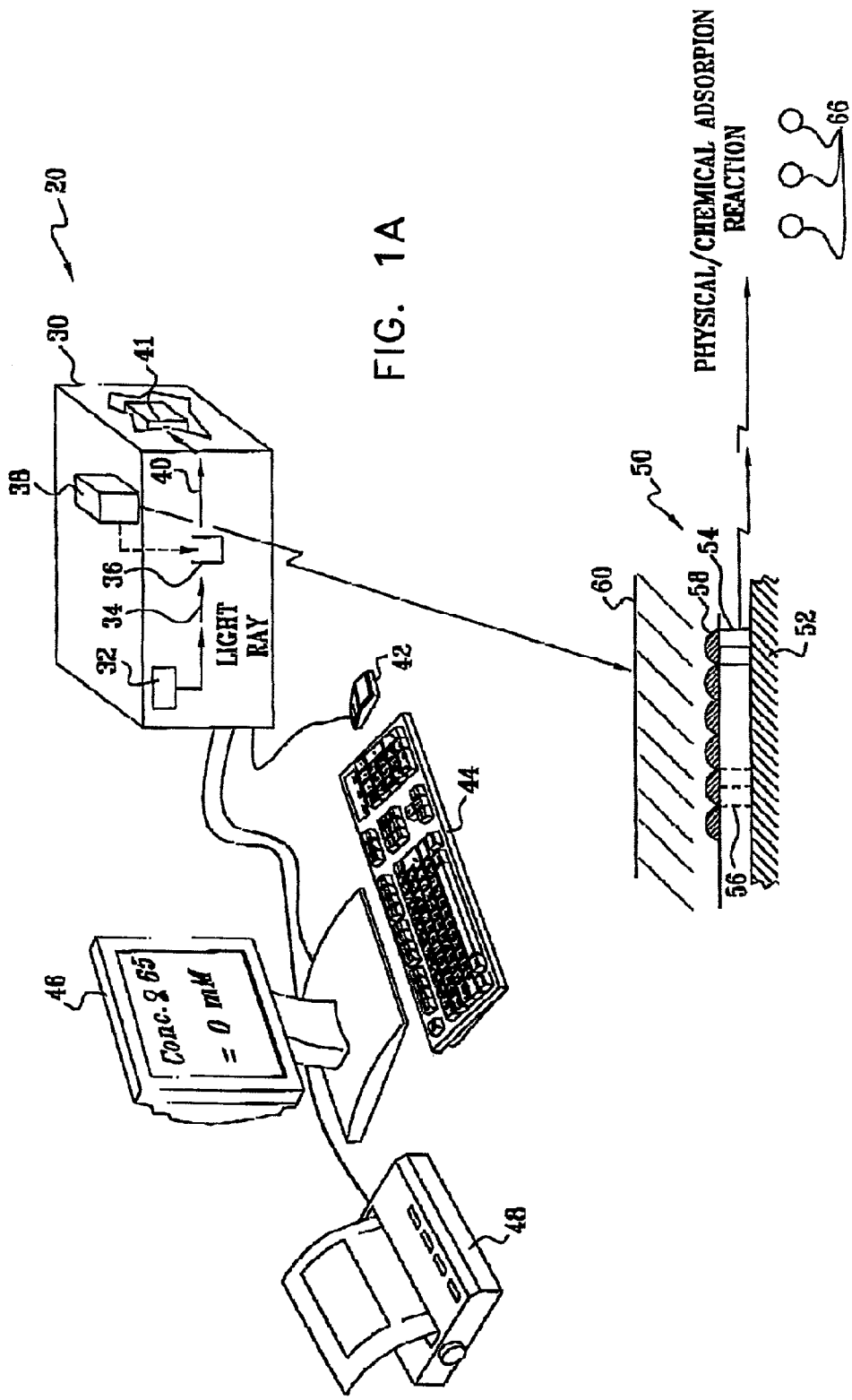

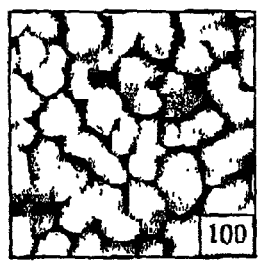
FIG. 4C/1
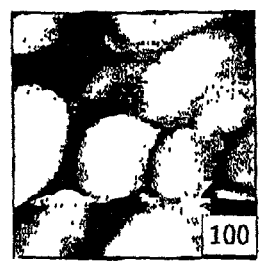
FIG. 4C/2
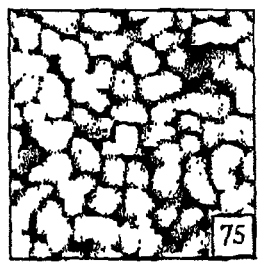
FIG. 4C/3
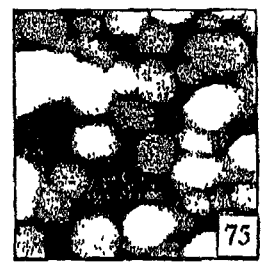
FIG. 4C/4
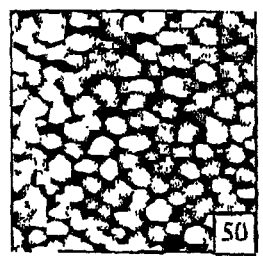
FIG. 4C/5
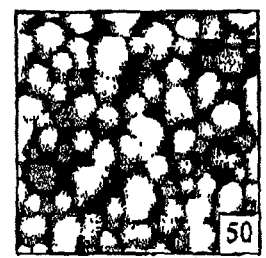
FIG. 4C/6
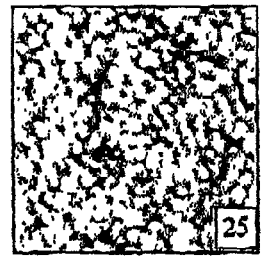
FIG. 4C/7
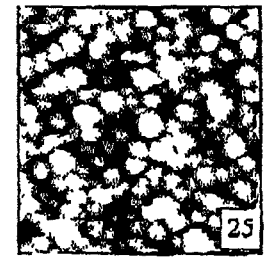
FIG. 4C/8
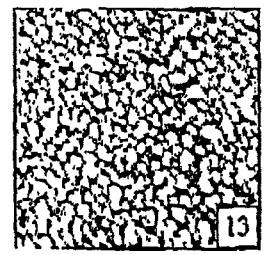
FIG. 4C/9
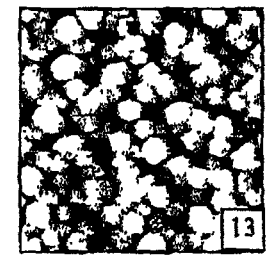
FIG. 4C/10

FIG. 4G/1
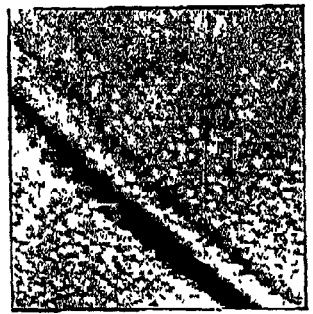
FIG. 4G/2
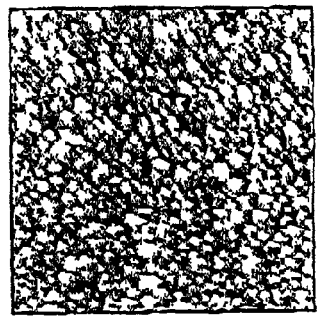
FIG. 4G/3
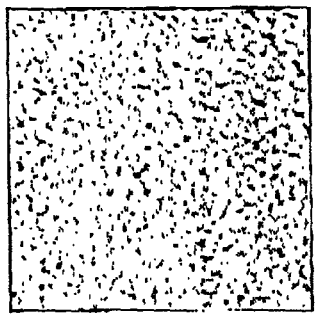
FIG. 4G/4
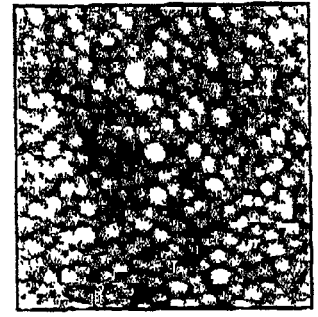
FIG. 4G/5
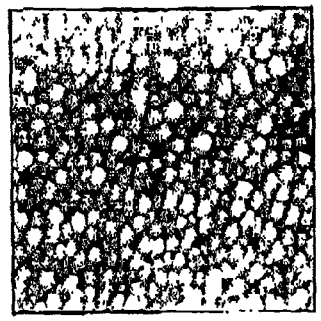
FIG. 4G/6
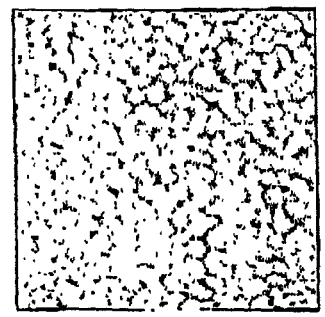
FIG. 4G/7
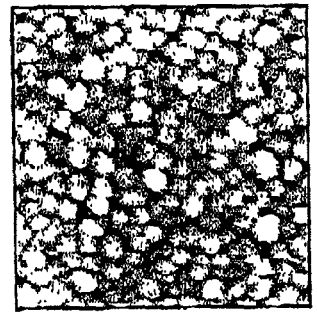
FIG. 4G/8
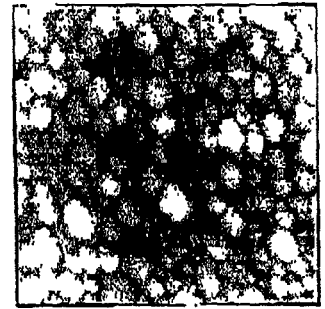
FIG. 4G/9

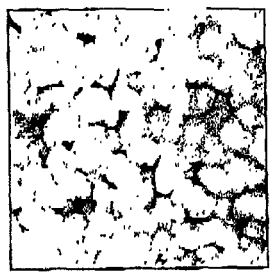  
FIG. 4G/10     FIG. 4G/11     FIG. 4G/12

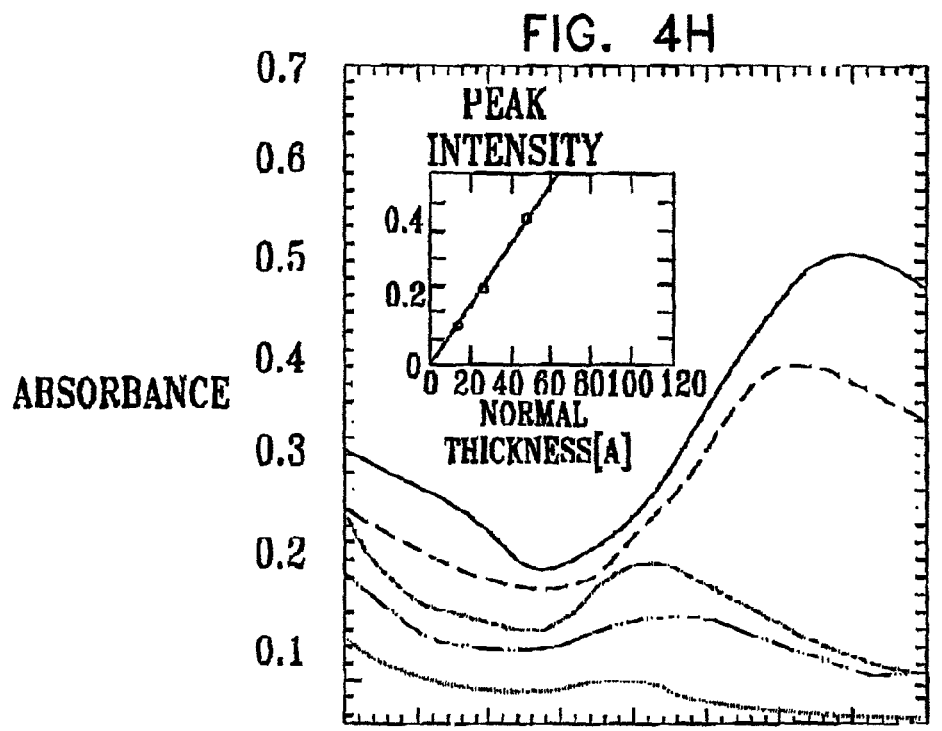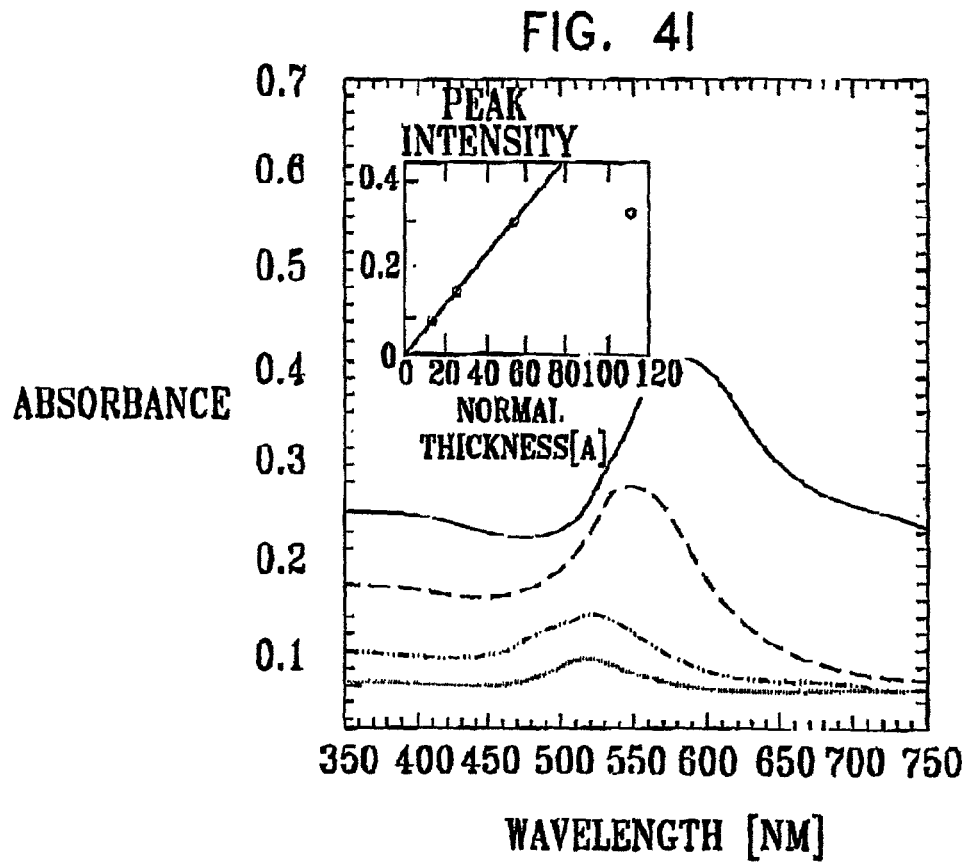

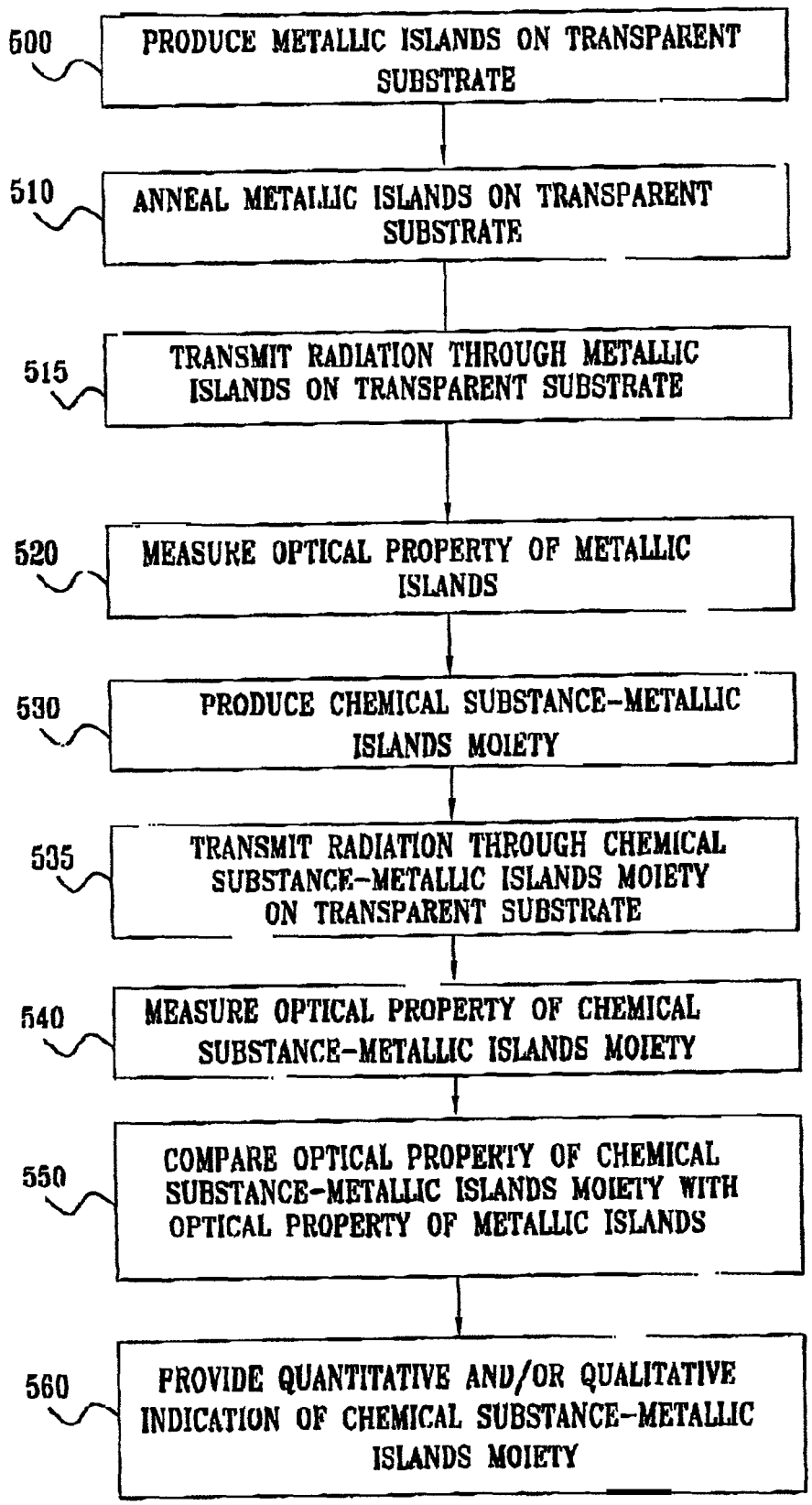

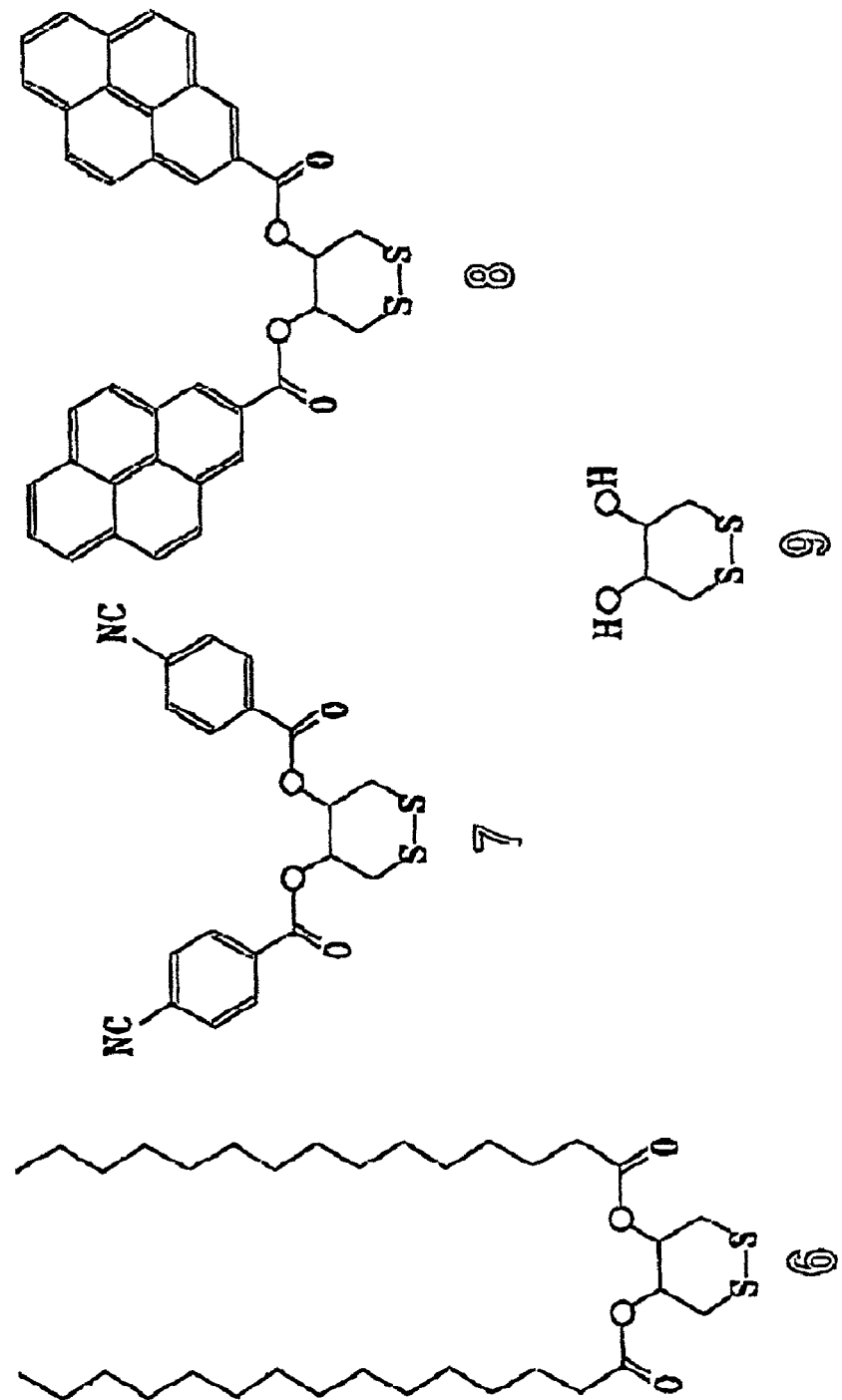

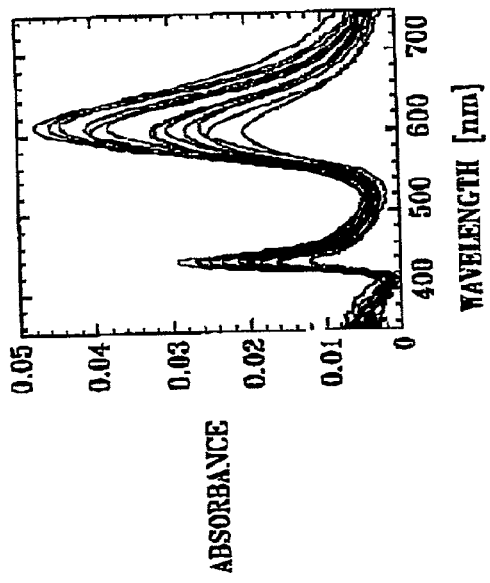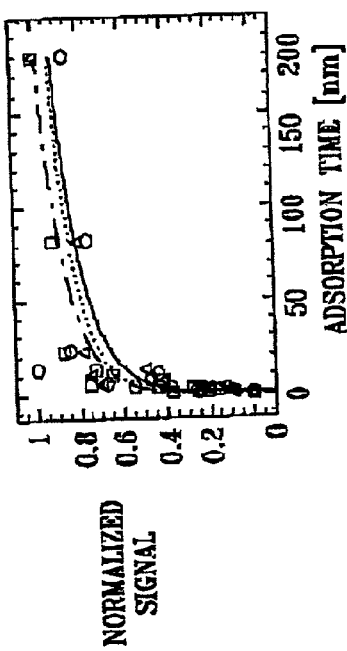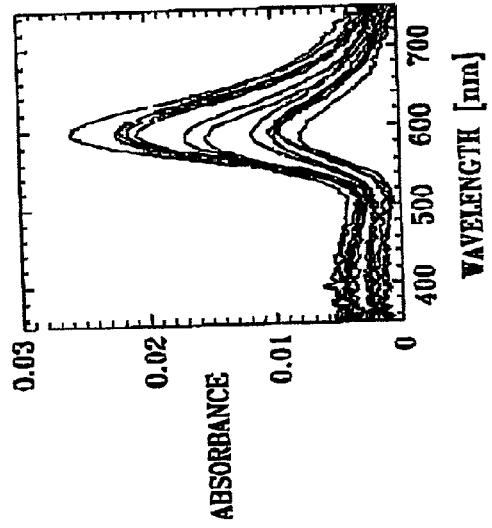

METHOD AND APPARATUS FOR DETECTING AND QUANTIFYING A CHEMICAL SUBSTANCE EMPLOYING AN OPTICAL TRANSMISSION PROPERTY OF METALLIC ISLANDS ON A TRANSPARENT SUBSTRATE

REFERENCE TO CO-PENDING APPLICATIONS

This application claims priority of U.S. Provisional Patent Application Ser. No. 60/271,620 filed Feb. 26, 2001, entitled UV/vis Surface Plasmon Measurements for Monitoring Adsorption on Ultrathin Gold films.

FIELD OF THE INVENTION

The present invention relates generally to chemical detection methods and apparatus, and more specifically to chemical detection methods and apparatus employing optical properties.

BACKGROUND OF THE INVENTION

The properties of ultra-thin films of metals of less than 10 nm thickness, are quite different to the properties of bulk metal. These metallic films may be transparent up to a thickness of 30 nm. The physical and chemical properties of these films are reviewed in the following references, which are believed to be representative of the state of the art: Kalyuzhny, G.; Vaskevich, A.; Matlis, S.; Rubinstein, I. Rev. *Anal. Chem.* 1999, 18, 237-242, and Kalyuzhny, G., Vaskevich A., Ashkenasy G., Shanzer A., and Rubinstein I. 2000, *J. Phys. Chem.* B 104, 8238-8244.

An article published on the Internet entitled Cranfield Biotechnology Centre-surface plasmon resonance appears at website www.cranfield.ac.uk/biotech/spr.htm describes use of reflected light for using surface plasmon resonance in diagnostic and sensing systems.

The following patents are believed to be representative of the state of the art: U.S. Pat. No. 5,449,918 to Krull et al., which describes a novel optical chemical sensor for direct and continuous detection of organic species in process streams employing thin metal island films, and U.S. Pat. No. 6,208,422 to Naya which describes a surface plasmon sensor including a dielectric block, a metal film having a sample supporting side which is faced toward a face of the dielectric block.

SUMMARY OF THE INVENTION

It is an object of some aspects of the present invention to provide chemical detection and quantification methods and apparatus employing optical properties of ultra-thin metallic films.

In preferred embodiments of the present invention, improved methods and apparatus are provided for detecting changes in surface plasmon intensity of an ultra-thin metallic film so as to provide a quantitative indication of an adsorbed or non-adsorbed chemical substance.

In other preferred embodiments of the present invention, improved methods and apparatus are provided for detecting changes in surface plasmon intensity of an ultra-thin metallic film so as to provide a qualitative indication of an adsorbed or non-adsorbed chemical substance.

In further preferred embodiments of the present invention, methods and apparatus for chemical quantification are provided employing adsorption of a chemical substance onto a plurality of metallic islands on a transparent substrate.

A typical method comprises electromagnetic radiation in the range of 300-1100 nm being transmitted through of a plurality of metallic islands on a transparent substrate, and a resultant optical property of the plurality of metallic islands on the transparent substrate is measured. The transparent substrate typically comprises glass, plastic, polystyrene, a polymeric material, quartz and mica, and is typically fully or substantially transparent in some or all of the UV/visible/IR range (300-1100 nm).

Thereafter a chemical substance is adsorbed the plurality of metallic islands so as to produce a chemical substance-metallic islands moiety on the transparent substrate. Electromagnetic radiation in the range of 300-1100 nm is transmitted through the chemical substance-metallic islands moiety on the transparent substrate, and a resultant optical property of the metallic islands in the chemical substance-metallic islands moiety is then measured. A comparison is made between the resultant optical property of the metallic islands in the chemical substance-metallic islands moiety and the resultant optical property of the plurality of metallic islands so as to provide an indication a quantity of at least one of the chemical substance-metallic islands moiety, a functionality thereof, the plurality of metallic islands, a functionality thereof, the chemical substance and a functionality thereof.

This method may be applied to quantify the concentration of chemical substances in a gaseous- and/or liquid-phase system. Similarly, the method may be applied to continuous monitoring or monitoring of kinetics of a chemical reaction.

In yet further preferred embodiments of the present invention, methods and apparatus for chemical detection employing a chemical substance adsorbed onto a plurality of metallic islands for detecting adsorption of a chemical substance onto a plurality of metallic islands are described.

Typically, electromagnetic radiation in the range of 300-1100 nm being transmitted through of a plurality of metallic islands on a transparent substrate, and a resultant optical property of the plurality of metallic islands on the transparent substrate is measured. The transparent substrate typically comprises glass, plastic, polystyrene, a polymeric material, quartz and mica, and is typically fully or substantially transparent in some or all of the UV/visible/IR range (300-1100 nm).

Thereafter a chemical substance is adsorbed the plurality of metallic islands so as to produce a chemical substance-metallic islands moiety on the transparent substrate. Electromagnetic radiation in the range of 300-1100 nm is transmitted through the chemical substance-metallic islands moiety on the transparent substrate, and a resultant optical property of the metallic islands in the chemical substance-metallic islands moiety is then measured. A comparison is made between the resultant optical property of the chemical substance-metallic islands moiety and the resultant optical property of the plurality of metallic islands so as to provide an indication a quantity of at least one of the chemical substance-metallic islands moiety, a functionality thereof, the plurality of metallic islands, a functionality thereof, the chemical substance and a functionality thereof.

In additional preferred embodiments for the present invention, the monitoring of changes in the surface plasmon intensity of a plurality of gold islands on a transparent substrate is performed by measuring changes in an optical property of the gold island's UV/visible/IR transmission spectrum. Preferably the optical property is a wavelength of maximum absorbance. Additionally or alternatively, the optical property is an intensity of absorbance band for a range of wavelengths in the UV/visible range/IR (300-1100 nm), known as a surface plasmon absorption band.

In some preferred embodiments, the metallic islands on the transparent substrate are annealed prior to adsorption of the chemical substance.

In some other preferred embodiments, an intermediate layer is formed in between the transparent layer and the metallic islands. The intermediate layer typically comprises a metal or metallic oxide, such as titanium oxide, nickel oxide or chromium oxide. This layer may enhance the adhesion of the metallic islands to the transparent substrate. Additionally or alternatively, the transparent substrate may be chemically treated to improve the metallic island adhesion thereto.

In some other preferred embodiments of the present invention, apparatus and methods for chemical quantification are provided employing a second chemical substance communicating with a first a chemical substance adsorbed onto a plurality of metallic islands so as to form a first chemical substance-metallic islands moiety. Typically the method comprises transmitting electromagnetic radiation in the range of 300-1100 nm through the first chemical substance-metallic islands moiety and the transparent substrate. A resultant optical property of metallic islands in the first chemical substance-metallic islands moiety is measured. Thereafter, communication of the second chemical substance with the first chemical substance induces formation of a second chemical substance-first chemical substance-metallic islands moiety. Electromagnetic radiation in the range of 300-1100 nm is transmitted through the second chemical substance-first chemical substance-metallic islands moiety on the transparent substrate, and a resultant optical property of the metallic islands therein is then measured.

The resultant optical property of metallic islands in the second chemical substance-first chemical substance-metallic islands moiety is measured and compared to that of the metallic islands in first chemical substance-metallic islands moiety so as to provide an indication of a quantity of at least one of the second chemical substance, a functionality thereof, the second chemical substance-first chemical substance-metallic islands moiety, a functionality thereof; the first chemical substance-metallic islands moiety, a functionality thereof; the plurality of metallic islands, a functionality thereof, the first chemical substance and a functionality thereof. This method may also be used in qualitative detection systems.

In other preferred embodiments of the present invention, the methods described herein are used in the preparation of chemical quantification kits and chemical qualitative detection kits. These kits typically comprise a plurality of metallic islands on a transparent substrate, a transmitter configured to transmit electromagnetic radiation through the plurality of metallic islands on the transparent substrate so as to enable measurement of a resultant optical property of the plurality of metallic islands on the transparent substrate, and further configured to transmit electromagnetic radiation through a chemical substance-metallic islands moiety on the transparent substrate so as to enable measurement of a resultant optical property of the chemical substance-metallic islands moiety on the transparent substrate; and processing element adapted to compare the resultant optical property of the chemical substance-metallic islands moiety with the resultant optical property of the plurality of metallic islands so as to provide an indication of a quantity of at least one of the chemical substance, a functionality thereof, the chemical substance-metallic islands moiety, a functionality thereof; the plurality of metallic islands and a functionality thereof.

Additionally or alternatively, kits may comprise two or more chemical substances capable of communicating with the metallic islands or intercommunicating. The communication may be physical or chemical adsorption, or chemical bonding. The chemical substances may bind together, may be ions, reactants, ligands, activators, inhibitors, enzymes, genetic elements and nucleic acids, for example.

In other preferred embodiments of the present invention, a method and system is described for using ultra-thin gold islands on transparent substrates as optical sensors. Preferably, such sensors can monitor quantitative or qualitative changes in both liquid- and gaseous-phase systems. The sensors may monitor at least one of a large variety of parameters. These parameters include, but are not limited to a concentration, a quantity, a binding parameter, a kinetics parameter. For example, a sensor may be used to detect an ion concentration in a fluid stream. Alternatively, a sensor may be used to determine inhibition kinetics of a bound enzyme, for example.

There is thus provided in accordance with a preferred embodiment of the present invention, a method for analysis including:
  transmitting electromagnetic radiation through a plurality of metallic islands on a transparent substrate,
  measuring a resultant optical property of the plurality of metallic islands on the transparent substrate,
  adsorbing a chemical substance onto the plurality of metallic islands so as to produce a chemical substance-metallic islands moiety on the transparent substrate,
  transmitting electromagnetic radiation through the chemical substance-metallic islands moiety,
  measuring a resultant optical property of metallic islands in the chemical substance-metallic islands moiety, and
  employing the resultant optical property of metallic islands in the chemical substance-metallic islands moiety and the resultant optical property of the metallic islands in the plurality of metallic islands so as to provide at least one of a quantitative indication and a qualitative indication of at least one of: the chemical substance-metallic islands moiety, a functionality of the chemical substance-metallic islands moiety, the plurality of metallic islands, a functionality of the plurality of metallic islands, the chemical substance and a functionality of the chemical substance.

In one preferred embodiment, adsorbing the chemical substance includes producing at least one of the following interactions between the chemical substance and the plurality of metallic islands: a hydrogen bond, an ionic bond, a covalent bond, a Van der Waals force, an electrostatic force and a physical force.

In another preferred embodiment, transmitting the electromagnetic radiation through the plurality of metallic islands on the transparent substrate includes transmitting electromagnetic radiation in the ultraviolet/visible/infra-red range.

In yet another preferred embodiment, transmitting the electromagnetic radiation through the plurality of metallic islands on the transparent substrate includes transmitting electromagnetic radiation in the range of 300-1100 nm.

In another preferred embodiment, transmitting the electromagnetic radiation through the chemical substance-metallic islands moiety on the transparent substrate includes transmitting electromagnetic radiation in the ultraviolet/visible/infra-red range.

In yet another preferred embodiment, transmitting the electromagnetic radiation through the chemical substance-metallic islands moiety on the transparent substrate includes transmitting electromagnetic radiation in the range of 300-1100 nm.

In another preferred embodiment, transmitting the electromagnetic radiation through the plurality of metallic islands on the transparent substrate includes transmitting electromagnetic radiation through the transparent substrate including at least one of the following: glass, plastic, polystyrene, a polymeric material, an inorganic oxide, quartz and mica.

Preferably, transmitting the electromagnetic radiation through the plurality of metallic islands on the transparent substrate includes transmitting electromagnetic radiation through the transparent substrate having a thickness of up to 5 mm.

Further preferably, transmitting the electromagnetic radiation through the plurality of metallic islands on the transparent substrate includes transmitting electromagnetic radiation through metallic islands including at least one of the following: gold, silver, copper, titanium, vanadium, chromium, steel, at least one ultra-thin layer of a metal, a binary alloy of the following elements: gold, silver, copper, titanium, vanadium, and chromium, or a ternary alloy of the following elements: gold, silver, copper, titanium, vanadium, and chromium.

Yet further preferably, the metallic islands are gold islands.

In another preferred embodiment, transmitting the electromagnetic radiation through the plurality of metallic islands on the transparent substrate includes transmitting electromagnetic radiation through metallic islands having a thickness of up to 400 Angstrom units. More preferably, the thickness is between 10 to 100 Angstrom units.

In yet another preferred embodiment, employing the resultant optical property of the plurality of metallic islands includes measuring a change in a surface plasmon absorbance of the plurality of metallic islands.

Preferably, the resultant optical property of the plurality of metallic islands includes a peak of maximal absorbance.

In another preferred embodiment, the resultant optical property of the chemical substance-metallic islands moiety includes a peak of maximal absorbance.

In yet another preferred embodiment, the resultant optical property of the chemical substance-metallic islands moiety includes an absorbance of metallic islands in the chemical substance-metallic islands moiety at a specific wavelength.

In another preferred embodiment, measuring a resultant optical property of the chemical substance-metallic islands moiety on the transparent substrate includes performing real-time measurements of the optical property of metallic islands in the chemical substance-metallic islands moiety.

In another preferred embodiment, employing the resultant optical property of the metallic islands in the chemical substance-metallic islands moiety and the resultant optical property of the plurality of metallic islands includes comparing the resultant optical property of the metallic islands in the chemical substance-metallic islands moiety and the resultant optical property of the plurality of metallic islands.

In another preferred embodiment, measuring a resultant optical property of the chemical substance-metallic islands moiety on the transparent substrate includes performing continuous measurements of the optical property of metallic islands in the chemical substance-metallic islands moiety.

In another preferred embodiment, measuring a resultant optical property of the chemical substance-metallic islands moiety on the transparent substrate includes performing kinetic monitoring of the resultant optical property of metallic islands in the chemical substance-metallic islands moiety.

In another preferred embodiment, the method includes producing the plurality of metallic islands on the transparent substrate.

In another preferred embodiment, producing the plurality of metallic islands producing the plurality of metallic islands from at least one of the following: gold, silver, copper, titanium, vanadium, chromium, steel, at least one ultra-thin layer of a metal, a binary alloy of the following elements: gold, silver, copper, titanium, vanadium, and chromium, or a ternary alloy of the following elements: gold, silver, copper, titanium, vanadium, and chromium.

In another preferred embodiment, producing the plurality of metallic islands includes evaporating the plurality of metallic islands.

In yet another preferred embodiment, producing the plurality of metallic islands includes sputtering the plurality of metallic islands.

In another preferred embodiment, producing the plurality of metallic islands includes electroless deposition of the plurality of metallic islands.

In another preferred embodiment, producing the plurality of metallic islands includes electrolytic deposition of the plurality of metallic islands.

In another preferred embodiment, producing the plurality of metallic islands includes hot-melt deposition of the plurality of metallic islands.

In another preferred embodiment, the method further includes annealing the plurality of metallic islands on the transparent substrate.

In another preferred embodiment, the annealing is performed prior to adsorbing the chemical substance onto the plurality of metallic islands. Preferably, annealing the plurality of metallic islands on the transparent substrate includes heating the plurality of metallic islands on the transparent substrate for up to 24 hours at up to 400° C. More preferably, annealing the plurality of metallic islands on the transparent substrate includes heating the plurality of metallic islands on the transparent substrate for up to 4 hours at up to 350° C.

There is thus provided in accordance with another preferred embodiment of the present invention, a method for analysis including:
  producing a plurality of metallic islands on an intermediate layer on a transparent substrate,
  transmitting electromagnetic radiation through the plurality of metallic islands on the intermediate layer on the transparent substrate,
  measuring a resultant optical property of the plurality of metallic islands,
  adsorbing a chemical substance onto the plurality of metallic islands so as to produce a chemical substance-metallic islands moiety on the intermediate layer on the transparent substrate,
  transmitting electromagnetic radiation through the chemical substance-metallic islands moiety,
  measuring a resultant optical property of metallic islands in the chemical substance-metallic islands moiety, and
  employing the resultant optical property the metallic islands in the chemical substance-metallic islands moiety and the resultant optical property of the plurality of metallic islands so as to provide at least one of a quantitative indication and a qualitative indication of at least one of: the chemical substance-metallic islands moiety, a functionality of the chemical substance-metallic islands moiety, the plurality of metallic islands, a functionality of the plurality of metallic islands, the chemical substance and a functionality of the chemical substance.

In a preferred embodiment, the intermediate layer includes at least one metal oxide.

In another preferred embodiment, the at least one metallic oxide includes at least one of the following: chromium oxide, titanium oxide, nickel oxide, lead oxide and tin oxide.

In a preferred embodiment, the intermediate layer includes a metal.

In another preferred embodiment, the intermediate layer includes at least one of a nitrogen containing moiety, a sulfur containing moiety and an inorganic hydrogen-containing moiety. Preferably, the intermediate layer includes at least one of the following chemical groups: sulfhydryl, thiocyanate, thiol, sulfide, disulfide and amine.

In another preferred embodiment, the intermediate layer includes an organic layer.

In another preferred embodiment, adsorbing the chemical substance includes producing at least one of the following interactions between the chemical substance and the plurality of metallic islands: a hydrogen bond, an ionic bond, a covalent bond, a Van der Waals force, an electrostatic force and a physical force.

In another preferred embodiment, transmitting the electromagnetic radiation through the plurality of metallic islands on the transparent substrate includes transmitting electromagnetic radiation in the ultraviolet/visible/infra-red range.

In yet another preferred embodiment, transmitting the electromagnetic radiation through the plurality of metallic islands on the transparent substrate includes transmitting electromagnetic radiation in the range of 300-1100 nm.

In a preferred embodiment, transmitting the electromagnetic radiation through the chemical substance-metallic islands moiety on the transparent substrate includes transmitting electromagnetic radiation in the ultraviolet/visible/infra-red range.

In another preferred embodiment, transmitting the electromagnetic radiation through the chemical substance-metallic islands moiety on the transparent substrate includes transmitting electromagnetic radiation in the range of 300-1100 nm.

In another preferred embodiment, transmitting the electromagnetic radiation through the plurality of metallic islands on the transparent substrate includes transmitting electromagnetic radiation through the transparent substrate including at least one of the following: glass, plastic, polystyrene, a polymeric material, an inorganic oxide, quartz and mica.

In yet another preferred embodiment, transmitting the electromagnetic radiation through the plurality of metallic islands on the transparent substrate includes transmitting electromagnetic radiation through the transparent substrate having a thickness of up to 5 mm.

In another preferred embodiment, transmitting the electromagnetic radiation through the plurality of metallic islands on the transparent substrate includes transmitting electromagnetic radiation through metallic islands including at least one of the following: gold, silver, copper, titanium, vanadium, chromium, steel, at least one ultra-thin layer of a metal, a binary alloy of the following elements: gold, silver, copper, titanium, vanadium, and chromium, or a ternary alloy of the following elements: gold, silver, copper, titanium, vanadium, and chromium.

More preferably, the metallic islands are gold islands.

In another preferred embodiment, transmitting the electromagnetic radiation through the plurality of metallic islands on the transparent substrate includes transmitting electromagnetic radiation through metallic islands having a thickness of up to 400 Angstrom units.

More preferably, the thickness is between 10 to 100 Angstrom units.

In another preferred embodiment, employing the resultant optical property of the plurality of metallic islands includes measuring a change in a surface plasmon absorbance of the plurality of metallic islands.

In another preferred embodiment, the resultant optical property of the plurality of metallic islands includes a peak of maximal absorbance.

In another preferred embodiment, the resultant optical property of the chemical substance-metallic islands moiety includes a peak of maximal absorbance of the metallic islands in the chemical substance-metallic islands moiety.

In another preferred embodiment, the resultant optical property of the chemical substance-metallic islands moiety includes an absorbance of the metallic islands in the chemical substance-metallic islands moiety at a specific wavelength.

In another preferred embodiment, measuring a resultant optical property of the chemical substance-metallic islands moiety on the transparent substrate includes performing real-time measurements of the optical property of the chemical substance-metallic islands moiety.

In yet another preferred embodiment, employing the resultant optical property of the chemical substance-metallic islands moiety and the resultant optical property of the plurality of metallic islands includes comparing the resultant optical property of metallic islands in the chemical substance-metallic islands moiety and the resultant optical property of the plurality of metallic islands.

In another preferred embodiment, measuring a resultant optical property of the chemical substance-metallic islands moiety on the transparent substrate of the chemical substance-metallic islands moiety includes performing continuous measurements of the optical property of the chemical substance-metallic islands moiety.

In another preferred embodiment, measuring a resultant optical property of the chemical substance-metallic islands moiety on the transparent substrate includes performing kinetic monitoring of the resultant optical property of the metallic islands in the chemical substance-metallic islands moiety.

There is thus provided in accordance with another preferred embodiment of the present invention, a method for analysis including:

transmitting electromagnetic radiation through a first chemical substance-metallic islands moiety on a transparent substrate, measuring a resultant optical property of the first chemical substance-metallic islands moiety, communicating the second chemical substance with the first chemical substance so as to form a second chemical substance-first chemical substance-metallic islands moiety, transmitting electromagnetic radiation through the second chemical substance-first chemical substance-metallic islands moiety on the transparent substrate, measuring a resultant optical property of metallic islands in the second chemical substance-first chemical substance-metallic islands moiety, and employing the resultant optical property of metallic islands in the second chemical substance-first chemical substance-metallic islands moiety and the resultant optical property of the first chemical substance-metallic islands moiety so as to provide at least one of a quantitative indication and a qualitative indication of at least one of: the second chemical substance, a functionality of the second chemical substance, the second chemical substance-first chemical substance-metallic islands moiety, a functionality of the second chemical substance-first chemical substance-metallic islands moiety, the first chemical substance-metallic islands moiety, a functionality of the first chemical substance-metallic islands moiety, the plurality of metallic islands, a functionality of the plurality of metallic islands, the first chemical substance and a functionality of the first chemical substance.

In a preferred embodiment, the first chemical substance includes at least one of the following: a chemical ion, an organic molecule, a polymer, an inorganic molecule, an enzyme, a nucleic acid, an antibody, and an antigen.

In another preferred embodiment, the second substance includes at least one of the following: a chemical ion, an organic molecule, an inorganic molecule, a polymer, an enzyme, a nucleic acid, an antibody, and an antigen.

In a preferred embodiment, communicating the second chemical substance with the first chemical substance includes at least one of the following: a physical adsorption, a chemical adsorption, a chemical reaction, a antigen-antibody interaction, a hybridization reaction, an enzyme-substrate interaction, an enzyme inhibitor interaction, an amplification reaction, a polymerase chain reaction, and a precipitation.

In another preferred embodiment, communicating the second chemical substance with the first chemical substance includes producing at least one of the following interactions between the chemical substance and the plurality of metallic islands: a hydrogen bond, an ionic bond, a covalent bond, a Van der Waals force, an electrostatic force and a physical force.

In a preferred embodiment, transmitting the electromagnetic radiation through the first chemical substance-metallic islands moiety includes transmitting electromagnetic radiation in the ultraviolet/visible/infra-red range.

In another preferred embodiment, transmitting the electromagnetic radiation through the first chemical substance-metallic islands moiety includes transmitting electromagnetic radiation in the range of 300-1100 nm.

In a preferred embodiment, transmitting the electromagnetic radiation through the chemical substance-metallic islands moiety on the transparent substrate includes transmitting electromagnetic radiation in the ultraviolet/visible/infra-red range.

There is thus provided in accordance with another preferred embodiment of the present invention, apparatus for analysis including:
an adsorption enabling element operative to enable adsorption of a chemical substance onto a plurality of metallic islands on a transparent substrate so as to produce a chemical substance-metallic islands moiety,
a transmitter operative to transmit electromagnetic radiation through the plurality of metallic islands, and which is further operative to transmit electromagnetic radiation through the chemical substance-metallic islands moiety,
a detector adapted to detect a resultant optical property of the plurality of metallic islands, and further configured to detect a resultant optical property of metallic islands in the chemical substance-metallic islands moiety, and
a processor operative to employ the resultant optical property of the metallic islands in the chemical substance-metallic islands moiety and the resultant optical property of the plurality of metallic islands so as to provide at least one of a quantitative indication and a qualitative indication of at least one of: the chemical substance-metallic islands moiety, a functionality of the chemical substance-metallic islands moiety, the plurality of metallic islands, a functionality of the plurality of metallic islands, the chemical substance and a functionality of the chemical substance.

In a preferred embodiment, the adsorption enabling element is operative to produce at least one of the following interactions between the chemical substance and the plurality of metallic islands: a hydrogen bond, an ionic bond, a covalent bond, a Van der Waals force, an electrostatic force and a physical force.

In a preferred embodiment, the electromagnetic radiation includes electromagnetic radiation in the ultraviolet/visible/infra-red range.

In a preferred embodiment, the electromagnetic radiation includes electromagnetic radiation in the range of 300-1100 nm.

In another preferred embodiment, the transparent substrate includes at least one of the following: glass, plastic, polystyrene, a polymeric material, an inorganic oxide, quartz and mica.

In a preferred embodiment, the transparent substrate has a thickness of up to 5 mm.

In a preferred embodiment, the plurality of metallic islands includes at least one of the following: gold, silver, copper, titanium, vanadium, chromium, steel, at least one ultra-thin layer of a metal, a binary alloy of the following elements: gold, silver, copper, titanium, vanadium, and chromium, or a ternary alloy of the following elements: gold, silver, copper, titanium, vanadium, and chromium.

Preferably, the metallic islands are gold islands.

In a preferred embodiment, the processor is further operative to compare the resultant optical property of metallic islands in the chemical substance-metallic islands moiety and the resultant optical property of the plurality of metallic islands.

In another preferred embodiment, the detector is further configured to perform continuous measurements of the optical property of the chemical substance-metallic islands moiety.

In a preferred embodiment, the detector is further configured to perform kinetic monitoring of the resultant optical property of the chemical substance-metallic islands moiety.

In a preferred embodiment, the apparatus includes a metal deposition element operative to produce the plurality of metallic islands on the transparent substrate.

In a preferred embodiment, the metal deposition element is operative to produce the plurality of metallic islands from at least one of the following: gold, silver, copper, titanium, vanadium, chromium, steel, at least one ultra-thin layer of a metal, a binary alloy of the following elements: gold, silver, copper, titanium, vanadium, and chromium, or a ternary alloy of the following elements: gold, silver, copper, titanium, vanadium, and chromium.

In a preferred embodiment, the metal deposition element is operative to evaporate the plurality of metallic islands.

In another preferred embodiment, the metal deposition element is operative to sputter the plurality of metallic islands.

In another preferred embodiment, the metal deposition element is operative to deposit by electroless deposition the plurality of metallic islands.

In a preferred embodiment, the metal deposition element is operative to deposit by electrolytic deposition the plurality of metallic islands.

In another preferred embodiment, the metal deposition element is operative to deposit by a hot-melt deposition the plurality of metallic islands.

In a preferred embodiment, the apparatus further includes a heating element operative to anneal the plurality of metallic islands on the transparent substrate.

In a preferred embodiment, the heating element is operative to heat the plurality of metallic islands for up to 24 hours at up to 400° C.

More preferably, the heating element is operative to heat the plurality of metallic islands for up to 4 hours at up to 350° C.

In a preferred embodiment, the adsorption enabling element is further configured to enable adsorption of an intermediate layer on the transparent substrate.

In a preferred embodiment,

132. Apparatus according to claim 131 and wherein the intermediate layer includes at least one metal oxide.

133. Apparatus according to claim 131 and wherein the at least one metallic oxide includes at least one of the following: chromium oxide, titanium oxide, nickel oxide, lead oxide and tin oxide.

There is thus provided in accordance with another preferred embodiment of the present invention, apparatus for analysis including:
- an adsorption enabling element configured to enable adsorption of a chemical substance onto a plurality of metallic islands on a transparent substrate so as to produce a first chemical substance-metallic islands moiety, and further to enable adsorption of a second chemical substance so as to form a second chemical substance-first chemical substance-metallic islands moiety,
- a transmitter operative to transmit electromagnetic radiation through the first chemical substance-metallic islands moiety and further operative to transmit electromagnetic radiation through the second chemical substance-first chemical substance-metallic islands moiety,
- a detector operative to detect a resultant optical property of metallic islands in the first chemical substance-metallic islands moiety, and further configured to detect a resultant optical property of metallic islands in the second chemical substance-first chemical substance-metallic islands moiety,
- a processor adapted to employ the resultant optical property of the metallic islands in the first chemical substance-metallic islands moiety and the resultant optical property of the of metallic islands in the second chemical substance-first chemical substance-metallic islands moiety so as to provide at least one of a quantitative indication and a qualitative indication of at least one of: the second chemical substance, a functionality of the second chemical substance, the second chemical substance-first chemical substance-metallic islands moiety, a functionality of the second chemical substance-first chemical substance-metallic islands moiety, the first chemical substance-metallic islands moiety, a functionality of the first chemical substance-metallic islands moiety, the plurality of metallic islands, a functionality of the plurality of metallic islands, the first chemical substance and a functionality of the first chemical substance.

In a preferred embodiment, the first chemical substance includes at least one of the following: a chemical ion, an organic molecule, a polymer, an inorganic molecule, an enzyme, a nucleic acid, an antibody, and an antigen.

In a preferred embodiment, the first second substance includes at least one of the following: a chemical ion, an organic molecule, an inorganic molecule, a polymer, an enzyme, a nucleic acid, an antibody, and an antigen.

In a preferred embodiment, the adsorption enabling element is further configured to enable communication of the second chemical substance with the first chemical substance by means of at least one of the following: a physical adsorption, a chemical adsorption, a chemical reaction, a antigen-antibody interaction, a hybridization reaction, an enzyme-substrate interaction, an enzyme inhibitor interaction, an amplification reaction, a polymerase chain reaction, and a precipitation.

In a preferred embodiment, the adsorption enabling element is further configured to produce at least one of the following interactions: a hydrogen bond, an ionic bond, a covalent bond, a Van der Waals force, an electrostatic force and a physical force.

In a preferred embodiment, the electromagnetic radiation includes electromagnetic radiation in the ultraviolet/visible/infra-red range.

In a preferred embodiment, the detector is further operative to detect a change in a surface plasmon absorbance.

In a preferred embodiment, the processor is further operative to compare the resultant optical property of metallic islands in the first chemical substance-metallic islands moiety and the resultant optical property of metallic islands in the second chemical substance-first chemical substance-metallic islands moiety.

In a preferred embodiment, the detector is further configured to perform continuous measurements of the optical property of metallic islands in the second chemical substance-first chemical substance-metallic islands moiety.

In another preferred embodiment, the detector is further configured to perform kinetic monitoring of the resultant optical property of metallic islands in the first chemical substance-metallic islands moiety.

In a preferred embodiment, the adsorption enabling element is further configured to enable adsorption of an intermediate layer on the transparent substrate.

There is thus provided in accordance with another preferred embodiment of the present invention, a kit for analysis including:
- a plurality of metallic islands on a transparent substrate,
- a transmitter configured to transmit electromagnetic radiation through the plurality of metallic islands on the transparent substrate, and further configured to transmit electromagnetic radiation through a chemical substance-metallic islands moiety on the transparent substrate,
- a detector adapted to detect a resultant optical property of the plurality of metallic islands, and further configured to detect a resultant optical property of metallic islands in the chemical substance-metallic islands moiety, and
- a processor configured to employ the resultant optical property of the metallic islands in chemical substance-metallic islands moiety with and resultant optical property of the plurality of metallic islands so as to provide at least one of a quantitative indication and a qualitative indication of at least one of: the chemical substance-metallic islands moiety, a functionality of the chemical substance-metallic islands moiety, the plurality of metallic islands, a functionality of the plurality of metallic islands, the chemical substance and a functionality of the chemical substance.

There is thus provided in accordance with another preferred embodiment of the present invention, a kit for analysis including:
- a first chemical substance adsorbed onto plurality of metallic islands on a transparent substrate so as to form a first chemical substance-metallic islands moiety, and wherein the first chemical substance-metallic islands moiety is configured to bind a second chemical substance so as to form a second chemical substance-first chemical substance-metallic islands moiety,
- a transmitter operative to transmit electromagnetic radiation through the first chemical substance-metallic islands moiety and which is further operative to transmit electromagnetic radiation through the second chemical substance-first chemical substance-metallic islands moiety, a detector adapted to detect a resultant optical property of metallic islands in the first chemical substance-metallic islands moiety, and further configured to detect a resultant optical property of metallic islands in the second chemical substance-first chemical substance-metallic islands moiety, a processor adapted to employ the resultant optical property of the metallic islands in the chemical substance-metallic islands moiety and the resultant optical property of the metallic islands in the second chemical substance-first chemical substance-metallic islands moiety so as to provide at least one of a quantitative indication and a qualitative indication of at least one of: the second chemical substance, a functionality of the second chemical substance, the second chemical substance-first chemical substance-metallic islands moiety, a functionality of the second chemical substance-first chemical substance-metallic islands moiety, the first chemical substance-metallic islands moiety, a functionality of the first chemical substance-metallic islands moiety, the plurality of metallic islands, a functionality of the plurality of metallic islands, the first chemical substance and a functionality of the first chemical substance.

There is thus provided in accordance with another preferred embodiment of the present invention, an optical sensor for analysis including:

a plurality of metallic islands on a transparent substrate, a transmitter configured to transmit electromagnetic radiation through the plurality of metallic islands on the transparent substrate, and further configured to transmit electromagnetic radiation through a chemical substance-metallic islands moiety on the transparent substrate, a detector adapted to detect a resultant optical property of the plurality of metallic islands, and further configured to detect a resultant optical property of metallic islands in the chemical substance-metallic islands moiety, and a processor adapted to employ the resultant optical property of the metallic islands in the chemical substance-metallic islands moiety and the resultant optical property of the plurality of metallic islands so as to provide at least one of a quantitative indication and a qualitative indication of at least one of: the chemical substance-metallic islands moiety, a functionality of the chemical substance-metallic islands moiety, the plurality of metallic islands, a functionality of the plurality of metallic islands, the chemical substance and a functionality of the chemical substance.

There is thus provided in accordance with another preferred embodiment of the present invention, an optical sensor for analysis including:

a first chemical substance adsorbed onto plurality of metallic islands on a transparent substrate so as to form a first chemical substance-metallic islands moiety, a transmitter configured to transmit electromagnetic radiation through the first chemical substance-metallic islands moiety on the transparent substrate, and further configured to transmit electromagnetic radiation through the second chemical substance-first chemical substance-metallic islands moiety on the transparent substrate, a detector adapted to detect a resultant optical property of metallic islands in the first chemical substance-metallic islands moiety, and further configured to detect a resultant optical property of metallic islands in the second chemical substance-first chemical substance-metallic islands moiety, and a processor adapted to employ the resultant optical property of the metallic islands in the chemical substance-metallic islands moiety and the resultant optical property of the metallic islands in the second chemical substance-first chemical substance-metallic islands moiety so as to provide at least one of a quantitative indication and a qualitative indication of at least one of: the second chemical substance, a functionality of the second chemical substance, the second chemical substance-first chemical substance-metallic islands moiety, a functionality of the second chemical substance-first chemical substance-metallic islands moiety, the first chemical substance-metallic islands moiety, a functionality of the first chemical substance-metallic islands moiety, the plurality of metallic islands, a functionality of the plurality of metallic islands, the first chemical substance and a functionality of the first chemical substance.

There is thus provided in accordance with another preferred embodiment of the present invention, a computer program product for analysis, the product including a computer-readable medium having program instructions embodied therein, which instructions, when read by a computer, cause the computer to:

transmit electromagnetic radiation through a plurality of metallic islands on a transparent substrate, measure an optical property of a plurality of metallic islands on a transparent substrate, adsorb a chemical substance onto the plurality of metallic islands so as to produce a chemical substance-metallic islands moiety on the transparent substrate, transmit electromagnetic radiation through the chemical substance-metallic islands moiety, measure an optical property of metallic island in the chemical substance-metallic islands moiety, and compare the optical property of metallic islands in the chemical substance-metallic islands moiety with the optical property of the plurality of metallic islands so as to provide at least one of a quantitative indication and a qualitative indication of at least one of: the chemical substance-metallic islands moiety, a functionality of the chemical substance-metallic islands moiety, the plurality of metallic islands, a functionality of the plurality of metallic islands, the chemical substance and a functionality of the chemical substance.

There is thus provided in accordance with another preferred embodiment of the present invention, a computer program product for analysis, the product including a computer-readable medium having program instructions embodied therein, which instructions, when read by a computer, cause the computer to:

transmit electromagnetic radiation through a first chemical substance-metallic islands moiety, measure an optical property of the first chemical substance-metallic islands moiety on a transparent substrate, communicate the second chemical substance with the first chemical substance so as to form a second chemical substance-first chemical substance-metallic islands moiety, transmit electromagnetic radiation through the second chemical substance-first chemical substance-metallic islands moiety, measure the optical property of metallic islands in the second chemical substance-first chemical substance-metallic islands moiety, and compare the optical property of the metallic islands in the second chemical substance-first chemical substance-metallic islands moiety with the optical property of the first chemical substance-metallic islands moiety so as to provide at least one of a quantitative indication and a qualitative indication of at least one of: the second chemical substance, a functionality of the second chemical substance, the second chemical substance-first chemical substance-metallic islands moiety, a functionality of the second chemical substance-first chemical substance-metallic islands moiety, the first chemical substance-metallic islands moiety, a functionality of the first chemical substance-metallic islands moiety, the plurality of metallic islands, a functionality of the plurality of metallic islands, the first chemical substance and a functionality of the first chemical substance.

The present invention will be more fully understood from the following detailed description of the preferred embodiments thereof, taken together with the drawings, in which:

BRIEF DESCRIPTION OF THE DRAWINGS

FIG. 1A is a simplified pictorial illustration showing a system for measuring an optical transmission property of metallic islands on a transparent substrate, in accordance with a preferred embodiment of the present invention;

FIGS. 4C/1-4C/10 is a series of images produced employing tapping mode scanning force microscopic topography prior to and following annealing, in accordance with a preferred embodiment of the present invention;

FIGS. 4G/1-4G/12 are a series of images produced by tapping mode scanning force microscopic topography of ultra-thin gold films on quartz, in accordance with a preferred embodiment of the present invention;

FIG. 4H are a series of UV/visible/IR spectra of non-annealed ultra-thin gold films on quartz, in accordance with a preferred embodiment of the present invention;

FIG. 4I are a series of UV/visible/IR spectra of annealed ultra-thin gold films on quartz, in accordance with a preferred embodiment of the present invention;

FIG. 5 is a simplified flowchart depicting a method for producing metallic islands and annealing them on a transparent substrate and thereafter detecting and quantifying a chemical substance employing an optical property of the metallic islands, in accordance with a preferred embodiment of the present invention;

FIG. 10B is a schematic representation of molecules 6-9 as is known in the art;

FIG. 11A is a series of successive UV/visible/IR spectra of self-assembled monolayers of ligand 1 adsorbed from a 0.4 mM solution of trichloromethane, in accordance with a preferred embodiment of the present invention;

FIG. 11B is a series of successive UV/visible/IR spectra of cobalt tetraphenylporphyrin (CoTPP) adsorbed onto a self-assembled monolayer of ligand 1, in accordance with a preferred embodiment of the present invention;

FIG. 11C is a graph showing the relation between adsorption times and the normalized quantities of absorption bands of a) plasmon intensity change after adsorption of molecule 1 of FIG. 11A [triangles], b) the plasmon intensity change accompanying CoTPP binding to the self-assembled monolayer of 1 as in FIG. 11B [squares], and Soret band absorbance after adsorption of CoTPP onto the self-assembled monolayer of ligand 1 of FIG. 11B;

DETAILED DESCRIPTION OF PREFERRED EMBODIMENTS

Figure 1B:
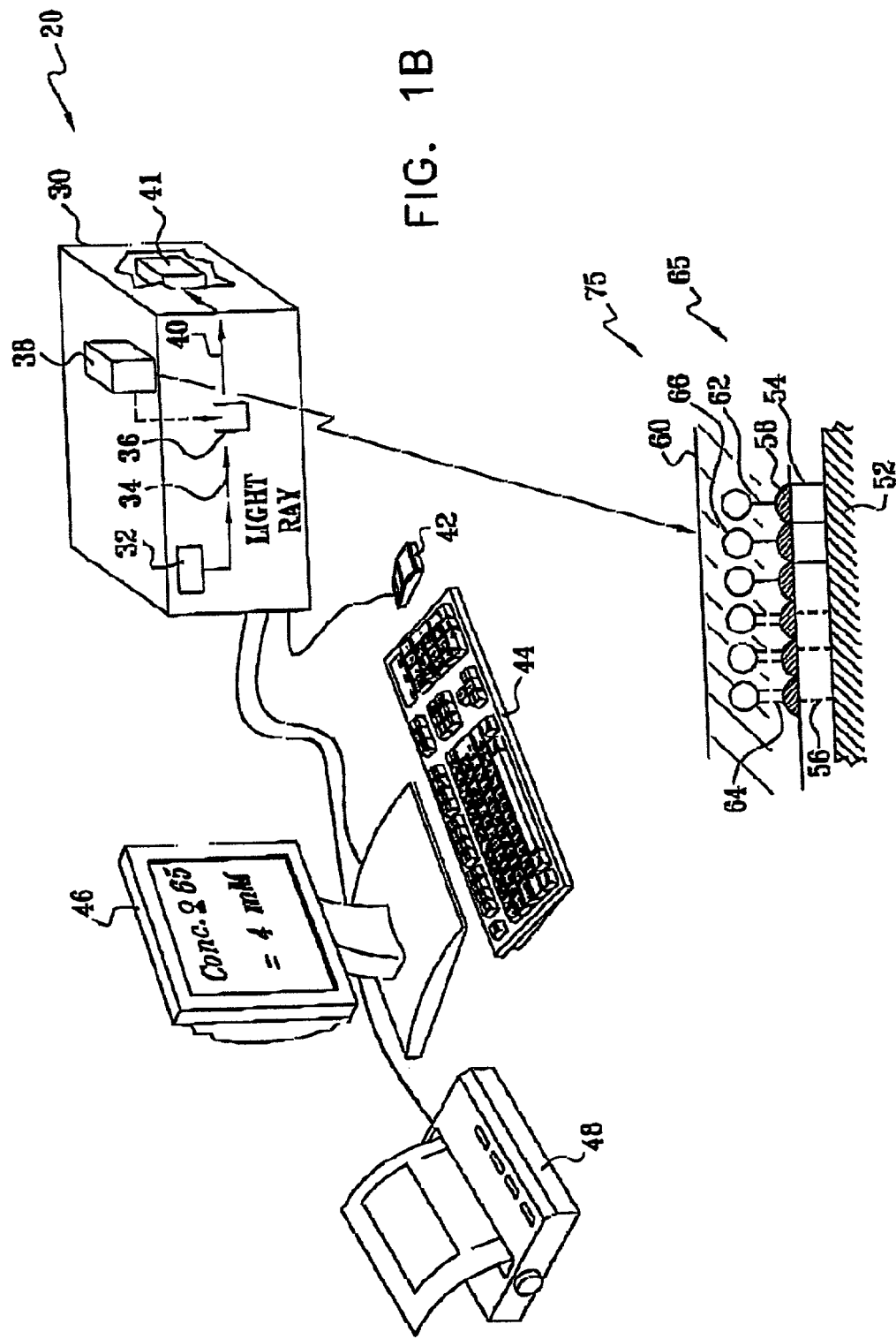
FIG. 1B is a simplified pictorial illustration showing a system for measuring an optical transmission property of a chemical substance-metallic islands moiety on a transparent substrate, in accordance with a preferred embodiment of the present invention.

Reference is now made to FIG. 1A, which is a simplified pictorial illustration showing a system 20 for measuring an optical property of a plurality of metallic islands 58 on a transparent substrate 52, in accordance with a preferred embodiment of the present invention.

System 20 typically comprises a processor 30 and a generator of electromagnetic energy, such as light. Generator 32 emits a light ray 34 to a receptacle receiving element 36. A receptacle 38 may be placed in receiving element 36 so that light ray 34 is transmitted therethrough. A resultant light ray 40 is emitted from receptacle 38. The properties of light ray 34 and resultant light ray 40 are typically measured by optical element 41. Output data from the optical element is processed by processor 30. Further data may be input manually employing a mouse 42 and or a keyboard 44. Both output and input data may be displayed on display 46, and printed on a printer 48. System 20 may comprise a spectrophotometer or other apparatus known in the art. Alternatively, system 20 may comprise a circuit with the microchips performing the functions of processor 30, generator 32 and optical element 41.

Typically, an adsorption system 50 comprises a transparent substrate 52 having adsorbed thereto by at least one chemical bond 54 and or by a physical contact 56, the plurality of metallic islands. Transparent substrate 52 typically comprises glass, plastic, polystyrene, quartz and mica, and is typically fully or substantially transparent in some or all of the UV/visible/IR range (300-1100 nm).

At least one chemical bond 54 may comprise by at least one of the following: a hydrogen bond, an ionic bond, a covalent bond, a Van der Waals force. Physical contact 56 may include an electrostatic force and a physical force.

The plurality of metallic islands typically comprise at least one of the following metals: gold, silver, copper, titanium, vanadium, chromium, steel, at least one ultra-thin layer of a metal, a binary alloy of the following elements: gold, silver, copper, titanium, vanadium, and chromium; or a ternary alloy of the following elements: gold, silver, copper, titanium, vanadium, and chromium. Most preferably, the metallic islands comprise gold.

In order to improve the adhesion between gold islands and the transparent substrate, an intermediate layer of oxides (NiO, $Cr_2O_3$, $TiO_2$) with thickness up to 5 nm may be deposited. Resistive evaporation of gold on these substrates is performed at rates 0.01-0.5 nm/s. Films with a gold layer thickness of less than 10 nm exhibit surface plasmon absorption band and are stable in organic as well as aqueous solutions.

Improvement of the adhesion of gold islands 58 to some substrates 52 such as glass and quartz may be achieved by silanization of the surface of the substrate [Goss, C. A.; Charych, D. H.; Majda, M. *Anal. Chem.* 1991, 63, 85-88] prior to gold deposition. Highly adhesive gold islands may also be obtained by similarly evaporating gold onto polymeric substrates, such as polystyrene. Deformation of the substrate may be avoided by control of the deposition time, the deposition rate and the substrate temperature during deposition or evaporation of the gold islands.

Metallic islands 58 are typically stable in a fluid phase 60 thereabove. Fluid phase 60 may comprise an aqueous or organic liquid, and/or a gaseous phase.

Adsorption system 50 may be placed in receptacle 38, such that light ray 34 is transmitted therethrough, and at least one resultant optical property of system 50 may be measured by system 20. The resultant optical property may comprise measuring a spectrum in the UV/visible/IR range, or more typically 300-1100 nm. Typically the optical property comprises a peak of maximal absorbance. Additionally or alternatively the optical property comprises measuring an absorbance at specific wavelength. The optical property may be measured continuously, in real-time, intermittently, or once off, for example.

After the resultant optical property of the plurality of metallic islands has been measured and preferably recorded, a chemical substance 66 may be communicated with adsorption system 50. This communication may involve chemical reaction, chemical adsorption or physical adsorption.

Reference is now made to FIG. 1B, which is a simplified pictorial illustration showing system 20 for measuring a resultant optical property of a chemical substance-metallic islands moiety 65 on transparent substrate 52, in accordance with a preferred embodiment of the present invention. Chemical substance 66 is adsorbed onto plurality of metallic islands 58, by at least one chemical bond 62 and/or at least one physical mechanism 64.

Adsorption system 50 with chemical substance 66 adsorbed thereto is referred to as a chemical substance-metallic islands moiety system 75. System 75 may be placed in receptacle 38, and light ray 34 is transmitted therethrough and at least one resultant optical property of system 75 may be measured by system 20. The resultant optical property may comprise measuring a spectrum in the UV/visible/IR range. Typically the resultant optical property comprises a peak of maximal absorbance. Additionally or alternatively the resultant optical property comprises measuring an absorbance at specific wavelength. The resultant optical property may be measured continuously, in real-time, intermittently, or once off, for example.

The resultant optical property of the chemical substance-metallic islands moiety 65 may be identical or substantially similar to that of system 75. The resultant optical property of the chemical substance-metallic islands moiety 65 is measured and preferably recorded by processor 30.

Processor 30 may then provide an indication of a quantity or quality of at least one of the chemical substance-metallic islands moiety 65, a functionality thereof, the plurality of metallic islands 58, a functionality thereof, the chemical substance 66 and a functionality thereof. For example, FIG. 1B shows a concentration of the chemical substance-metallic islands moiety 65 on display 46 calculated by processor 30 from information received from optical element 41 about resultant light ray 40.

Figure 1C:
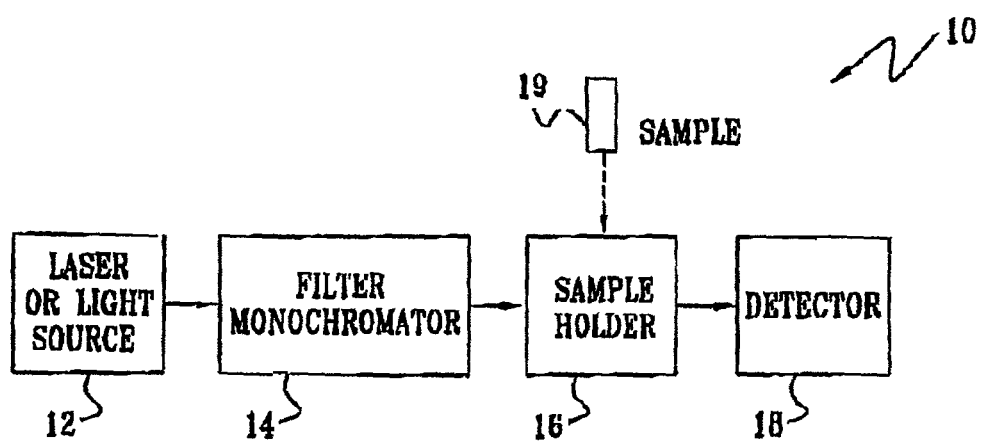
FIG. 1C is a simplified pictorial illustration of a system for measuring an optical transmission property of a chemical substance-metallic islands moiety on a transparent substrate, in accordance with a preferred embodiment of the present invention.

Reference is now made to FIG. 1C, which is a simplified pictorial illustration of a system for measuring an optical property of a chemical substance-metallic islands moiety on a transparent substrate, in accordance with a preferred embodiment of the present invention. In some cases system 20 of FIG. 1 may be too large and cumbersome or in some other way inappropriate for measuring an optical property of adsorption system 50 (FIGS. 1A & 1B). In such a case, an alternative optical property measuring system 10 may be employed.

System 10 comprises a source of electromagnetic radiation 12. Source 12 is more typically a light or laser source. If the electromagnetic radiation is in the visible light range, then a filter monochromator 14 is normally essential in system 10. In contrast, if the radiation is laser radiation, then no filter monochromator is required. Radiation is typically passed from source 12 via filter monochromator 14 to a sample holder 16 into/onto which a sample 19 is placed. The incident radiation is transmitted through sample 19 to a detector 18.

Additionally, the radiation may be reflected from sample 19 to detector 18. Radiation may be passed through sample 19 prior to adsorption of a chemical thereto and following adsorption thereto (as is described hereinabove in FIGS. 1A and 1B). A comparison may be made to determine the difference in transmission of radiation of the sample with the chemical adsorbed thereto and the sample without the adsorbed chemical. System 10 may then provide an indication of a quantity or quality of at least one of the chemical substance-metallic islands moiety 65, a functionality thereof, the plurality of metallic islands 58, a functionality thereof, the chemical substance 66 and a functionality thereof.

| Abbreviations. | |
|---|---|
| UV/vis/IR | ultraviolet/visible/infra-red. |
| AFM | atomic force microscopy |
| PIC | plasmon intensity change |
| SPR | surface plasmon resonance |
| Cryo-HV | cryogenic high vacuum |
| SFM | scanning force microscopy |
| TEM | transmission electron microscopy |
| SAM | self-assembled monolayer |
| CA | contact angle |
| DPS | differential plasmon spectroscopy |
| TFE | 2,2,2-trifluoroethanol |
| $T_b$ | boiling temperature |
| 4PM | 4-mercaptopyridine |
| EtOH | ethanol |
| 4ATP | 4-aminothiophenol |
| DMF | dimethylformamide |
| FeTPPCl | iron tetraphenylporphyrine chloride |
| CoTPP | cobalt tetraphenylporphyrine |
| CoPc | cobalt phthalocyanine |
| THF | tetrahydrofurane |
| Deg | degrees |

Figure 2:
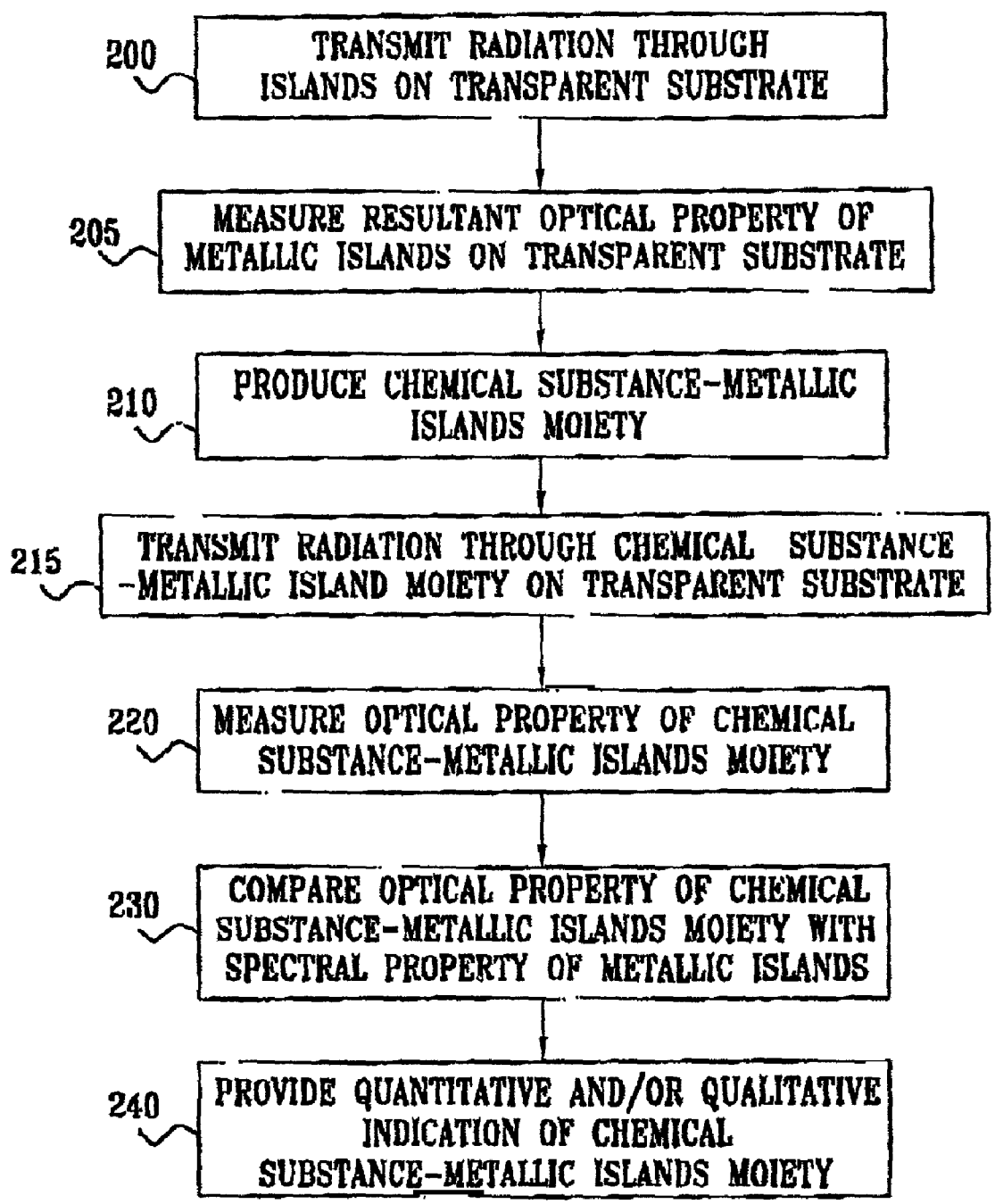
FIG. 2 is a simplified flowchart of a method for detecting and quantifying a chemical substance employing an optical transmission property of metallic islands on a transparent substrate, in accordance with a preferred embodiment of the present invention.

Reference is now made to FIG. 2, which is a simplified flowchart of a method for detecting and quantifying a chemical substance employing an optical property of metallic islands on a transparent substrate, in accordance with a preferred embodiment of the present invention. This method is exemplified in Example 1 and in Examples 5-9 hereinbelow.

In a transmission step 200, system 20 transmits radiation of 300-1100 nm wavelength through the plurality of metallic islands on transparent substrate 52 as described hereinabove.

In a measuring step 205, system 20 measures an optical property of adsorption system 50. Examples of the optical properties are provided in FIGS. 4E & 4F hereinbelow.

In a producing chemical substance-metallic islands moiety-step 210, the following reactions are performed, for example: A monolayer of 8 is formed on an non-annealed Au substrate (25 Å nominal thickness, evaporated on quartz), adsorbed from 2 mM solution of 8 in chloroform. Thus, the chemical substance-metallic islands moiety is the monolayer of 8 adsorbed onto gold.

In alternative embodiments of the present invention the metal islands are immersed in a solvent (see Examples 8-9 hereinbelow). This stage enables the conformation of the metallic islands to reach a steady state. Consequentially, the surface plasmon absorbance reaches a steady state. The chemical substance-metallic islands moiety 65 reaches steady state on substrate 52.

In a transmission step 215, a light or radiation ray 34 is transmitted through system 75.

In a measuring step 220, an optical property of chemical substance-metallic islands moiety 65 is measured. For example, an optical property of a monolayer of 8 adsorbed onto gold is measured. The optical property may include an absolute spectrum (FIG. 12A hereinbelow).

In a comparing step 230, the optical property of the chemical substance-metallic islands moiety may be compared with the optical property of the metallic islands. Typically, a system such as system 20 (FIG. 1) or system 10 of FIG. 1C provides difference spectra (obtained by subtraction of the 0 sec spectrum from the other spectra (as shown in FIG. 12A hereinbelow).

As is shown hereinbelow in FIG. 12D, a linear correlation is found between the plasmon intensity change (PIC) and the maximum absorbance of 8 at 365 nm (both from FIG. 12B). This linear correlation may be used to provide quantitative and/or qualitative indication of chemical substance-metallic islands moiety 65 in a provision step 240. Additionally or alternatively, the system may provide a qualitative and/or quantitative indication of at least one of the chemical substance-metallic islands moiety 65, a functionality thereof; the plurality of metallic islands 58, a functionality thereof, the chemical substance 66 and a functionality thereof.

In this context the word "functionality" is used broadly to include, but not to be limited to, a chemical functionality, a functionality, an optical functionality, an electronic functionality and a physical functionality.

A chemical functionality is used broadly to include, but not to be limited to, a chemical activity, a chemical reactivity, a chemical conformation, a concentration of a chemical part or all of the moiety, an isomeric conformation, a chemical kinetic functionality, a bonding conformation, a tautiomeric conformation, a chemical reaction intermediate, a pH, a surface property, and a surface reactivity.

A biological functionality is used broadly to include, but not to be limited to, a biological kinetic functionality, an enzymatic activity, an inhibitor activity, a cofactor activity, a nucleic acid activity, a hybridization activity, an antibody activity, an antigen activity, a biological amplification activity such as a polymerase chain reaction activity, an antibiotic activity, an operon activity, an activator activity, an ELISA system activity, a repressor activity, a microbiological activity, a plasmid activity, a viral activity and a tissue activity.

A physical functionality is used broadly to include, but not to be limited to, a temperature property, a pressure property, a magnetic property, a vapor pressure property, a contact angle property, a specific heat capacity, a phase-change transition, a solubility property, a surface tension property, a conductivity property and a density property.

An optical functionality is used broadly to include, but not to be limited to, a spectral transmission functionality, and spectral reflection functionality, a maximal wavelength of absorption, a minimum wavelength of absorption, a pigment functionality, a color functionality, a luminescence functionality, and an indicator functionality.

An electronic functionality is used broadly to include, but not to be limited to, an electrical conductivity, a capacitance, a resistance, an inductance, an ESR, a break down voltage, a voltage, a charge transfer, a redox potential and an amperage.

In this example, if system 20 provides a (plasmon intensity change) PIC value, then the chemical substance-metallic islands concentration may be calculated with an accuracy of +/−2%.

Figure 3A:
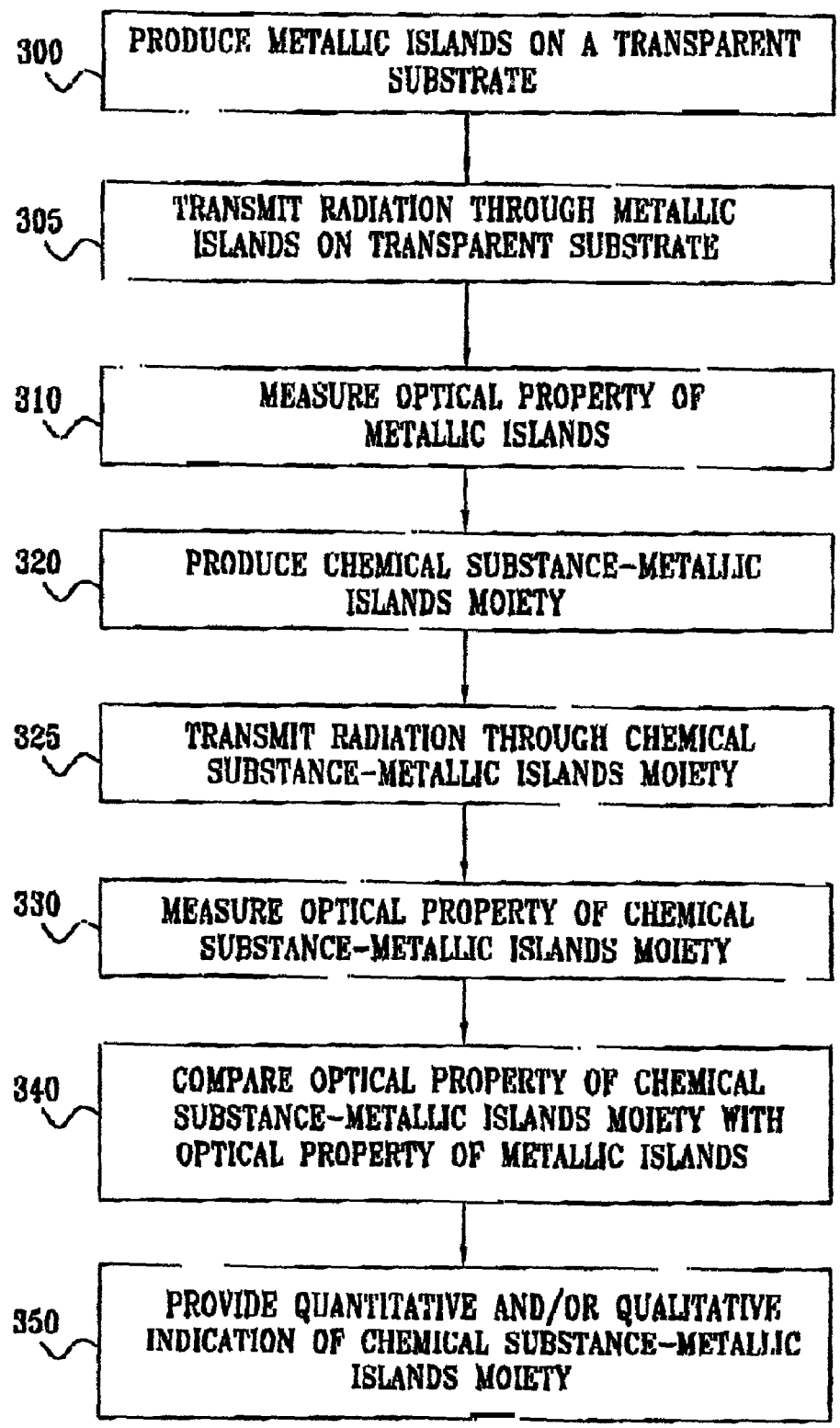
FIG. 3A is a simplified flowchart depicting a method for producing metallic islands on a transparent substrate and thereafter detecting and quantifying a chemical substance employing an optical property of the metallic islands, in accordance with a preferred embodiment of the present invention.

Reference is now made to FIG. 3A, which is a simplified flowchart depicting a method for producing metallic islands on a transparent substrate and thereafter detecting and quantifying a chemical substance employing an optical property of the metallic islands, in accordance with a preferred embodiment of the present invention. This method is exemplified in Example 1 and in Examples 5-9 hereinbelow.

In a metal deposition step 300, metallic islands are produced on a transparent substrate. For example, gold substrates utilized in this work were prepared using a cryo-HV evaporator (Key High Vacuum) equipped with a Maxtek TM-100 thickness monitor. Homogeneous deposition was obtained by moderate rotation of the substrate plate. Gold (99.99%) was evaporated from a tungsten boat at $4-5 \times 10^{-6}$ torr.

Ultrathin gold films (13-100 Å thick) were prepared by mounting freshly cleaved mica or extensively rinsed (with ethanol) glass or quartz slides in the evaporator. Gold (99.99%) was evaporated at a deposition rate of 0.05-4 Å/sec.

Post deposition thermal treatment (annealing) of evaporated Au-covered substrates was carried out in air, at 250° C. for 2.5-4 h. Additionally or alternatively, metal islands 58 may be produced by electroless deposition, electrolytic deposition or by hot-melt methods known in the art.

In a transmission step 305, radiation is transmitted through metallic islands on the transparent substrate.

An optical property of the metallic islands, such as the gold is then measured in a measuring step 310, which is substantially similar to step 200 hereinabove.

A chemical substance-metallic islands moiety is produced in an adsorption step 320. Step 320 may involve chemical and/or physical adsorption. Furthermore, the chemical substance may be bonded to the metallic islands, or may be loosely associated therewith (see FIG. 1B hereinabove). This step may be substantially similar to step 210 hereinabove.

In a transmission step 325, radiation is transmitted through chemical substance-metallic islands moiety and the transparent substrate.

Thereafter, in a measuring stem 330, an optical property of the chemical substance-metallic islands moiety is measured. Typically, system 20 (FIGS. 1A & 1B) comprises a spectrophotometer.

In a comparing step 340, the optical property of chemical substance-metallic islands moiety is compared with the optical property of metallic islands. This is further described in FIG. 12B hereinbelow.

Thereafter in an indicating step 350, a quantitative and/or qualitative indication of chemical substance-metallic islands moiety is provided. This indication may include, but is not limited to a quantity the chemical substance-metallic islands moiety, a functionality thereof; the plurality of metallic islands, a functionality thereof, the chemical substance and a functionality thereof.

Typically, system 20 provides a print-out on printer 48 or a screen-displayed result on screen 46. Additionally or alternatively, some manual calculations may be made to provide additional information concerning these quantitative and qualitative indications.

Figure 3B:
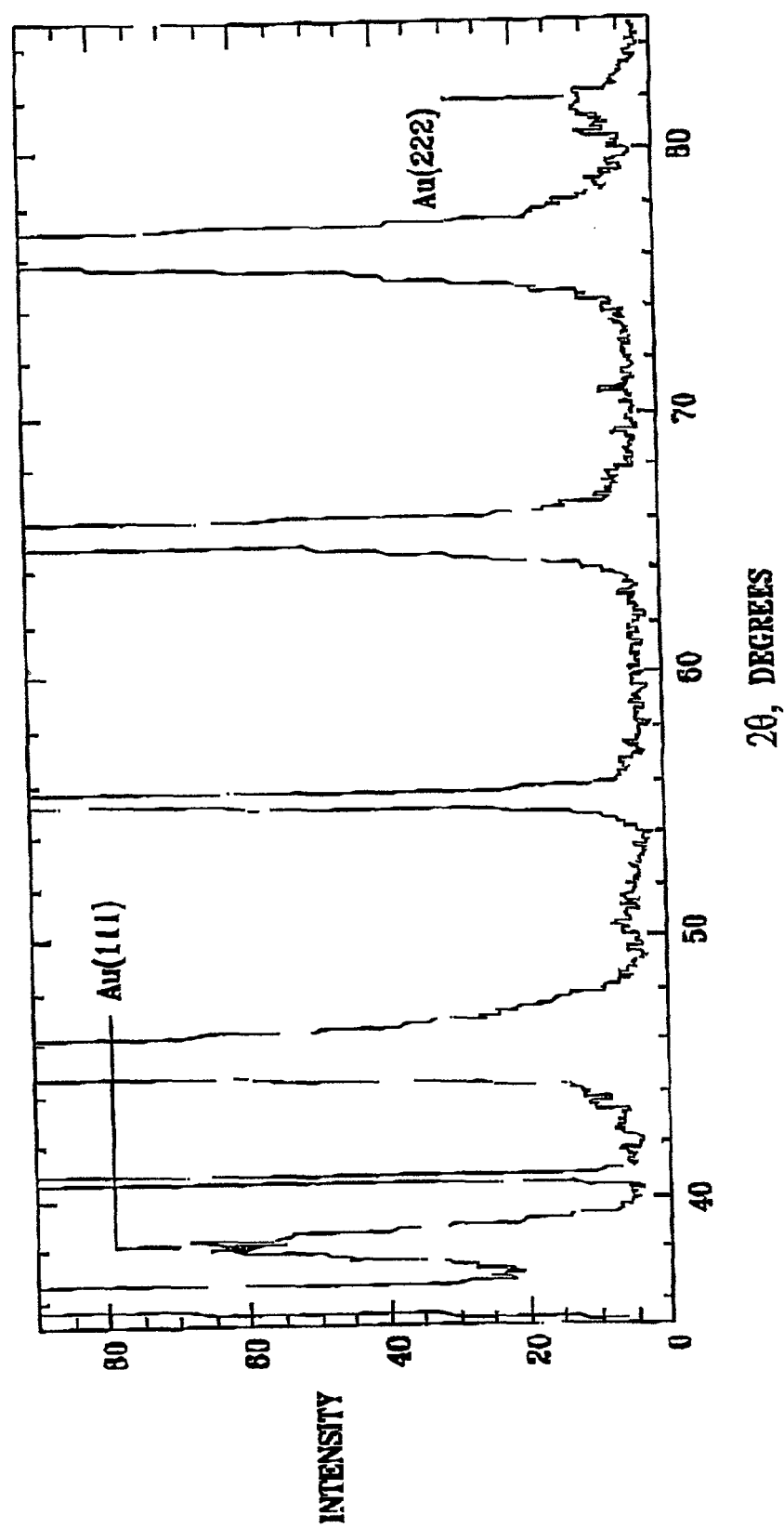
FIG. 3B is an X-ray diffraction pattern of a gold film produced by the method illustrated in FIG. 3A.

Reference is now made to FIG. 3B, which is an X-ray diffraction pattern of a gold film produced by the method illustrated in FIG. 3A;

The diffraction patterns of both annealed (FIG. 3B) and non-annealed (not shown) gold island films show a peak corresponding to Au(111). A much weaker peak corresponding to Au(222) may be resolved for the films of nominal thickness $\geq 25$ Å. The presence of Au(200), Au(220) and Au(311) reflections cannot be established due to the presence of intense mica lines. The Au(400), Au(331), Au(420) and Au(422) reflections are not detected even for the thickest (100 Å) films. These results indicate that the gold island films evaporated on mica are {111} textured, similar to thicker evaporated gold films.

The Au(111) line broadening was used to calculate the average island height using the Scherrer formula: $t=\lambda/B \cos \theta$, where t is the crystal height in Å, $\lambda$ is the X-ray wavelength (1.5406 Å), B is the line broadening in rad, and $\theta$ is the position of X-ray peak. As seen in Table 1, the calculated average crystal height of ultrathin gold films is notably different from the nominal thickness, although the discrepancy tends to decrease with increasing thickness. The crystal height of annealed films is larger than that of non-annealed films, in agreement with the SFM results. The difference in crystallinity (i.e. in average crystal size) between annealed and non-annealed films increases with increasing thickness, showing either that the thinner films need less energy to crystallize, or the role of the mica substrate. The large discrepancy between the nominal thickness and the X-ray calculated crystal height is attributed to (i) the island morphology of the film; (ii) the relatively large error (up to 50%) in crystal size calculated using the Scherrer formula; and (iii) in the case of a size distribution, the "average" size obtained from X-ray measurements is biased towards the larger crystals.

TABLE 1

Average crystal height in ultrathin gold films, calculated from the broadening of the Au (111) diffraction peak (see text).

| Nominal film thickness, ... | Annealing | 2 θ, degrees | Calculated crystal height, ... |
|---|---|---|---|
| 13 | + | 38.2 | 80 |
| 13 |   | 38.1 | 50 |
| 25 | + | 38.2 | 80 |
| 25 |   | 38.1 | 70 |
| 50 | + | 38.2 | 120 |
| 50 |   | 38.2 | 80 |
| 75 | + | 38.2 | 172 |
| 75 |   | 38.2 | 115 |
| 100 | + | 38.2 | 207 |
| 100 |   | 38.2 | 122 |

Figure 4A:
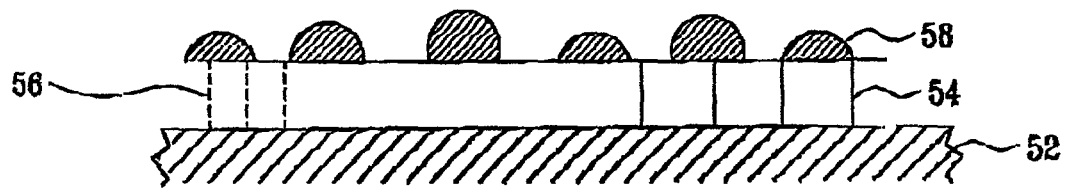
FIGS. 4A and 4B are simplified pictorial illustrations showing the effect of annealing on metallic islands' morphology.
Figure 4B:
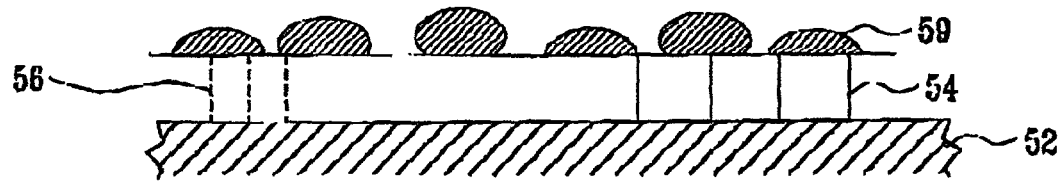

Reference is now made to FIGS. 4A and 4B, which are simplified pictorial illustrations showing the effect of annealing on metallic islands' morphology.

Prior to annealing, a cross section of a plurality of metallic islands shows the islands as small discrete hemi-spherical islands. The contact angle to the surface of substrate 52 may be from 0 to 180°. More typically, it is from 30 to 150°.

Comparison of the non-annealed islands 58 and the annealed films 59 shows that annealing leads to larger separation between individual islands, a noticeable increase in the island diameter and height, and flattening of the upper surface, exposing the (111) crystallographic face. The latter is also seen from the pseudo-hexagonal shape of islands and also from X-ray diffraction results (see FIG. 3B above). The island faceting is better seen in the expanded phase-shift image of the annealed 100 Å (nominal thickness) film (FIG. 4D) Image analysis manifested the hexagonal shape for the samples with lower nominal thickness as well (not shown).

Typically, annealing conditions comprise heating the metallic islands on the transparent substrate for 0-24 hours at temperatures of 150-400° C. Annealing is typically performed in an oven, or in situ in a sputter or evaporation machine.

Reference is now made to FIGS. 4C/1-4C/10, which are a series of images produced employing tapping mode scanning force microscopic topography prior to and following annealing, in accordance with a preferred embodiment of the present invention.

Ultrathin gold films of islands were prepared on mica (300 nm scan). The films were of nominal thickness 100, 75, 50, 25, and 13 Å (as indicated). Tapping mode SFM topographic images of these films prior to and following annealing are displayed in FIGS. 4C/1-4C/10.

A general dependence of the island size (average diameter and height) on the nominal thickness is observed for both non-annealed and annealed samples (FIGS. 4C/1-4C/10). It should be noted that the mica surface could be seen only in the annealed samples with a high nominal thickness. All other films look microscopically continuous, which appears to contradict data that these metallic islands are discontinuous (do not conduct electricity), where gold islands on glass or quartz were separated by distances comparable to their size. This may be explained by the different evaporation conditions (especially the low evaporation rates used here). With films of lower nominal thickness, it is possible that the SFM (scanning force microscopy) tip does not penetrate to the mica surface.

Figure 4D:
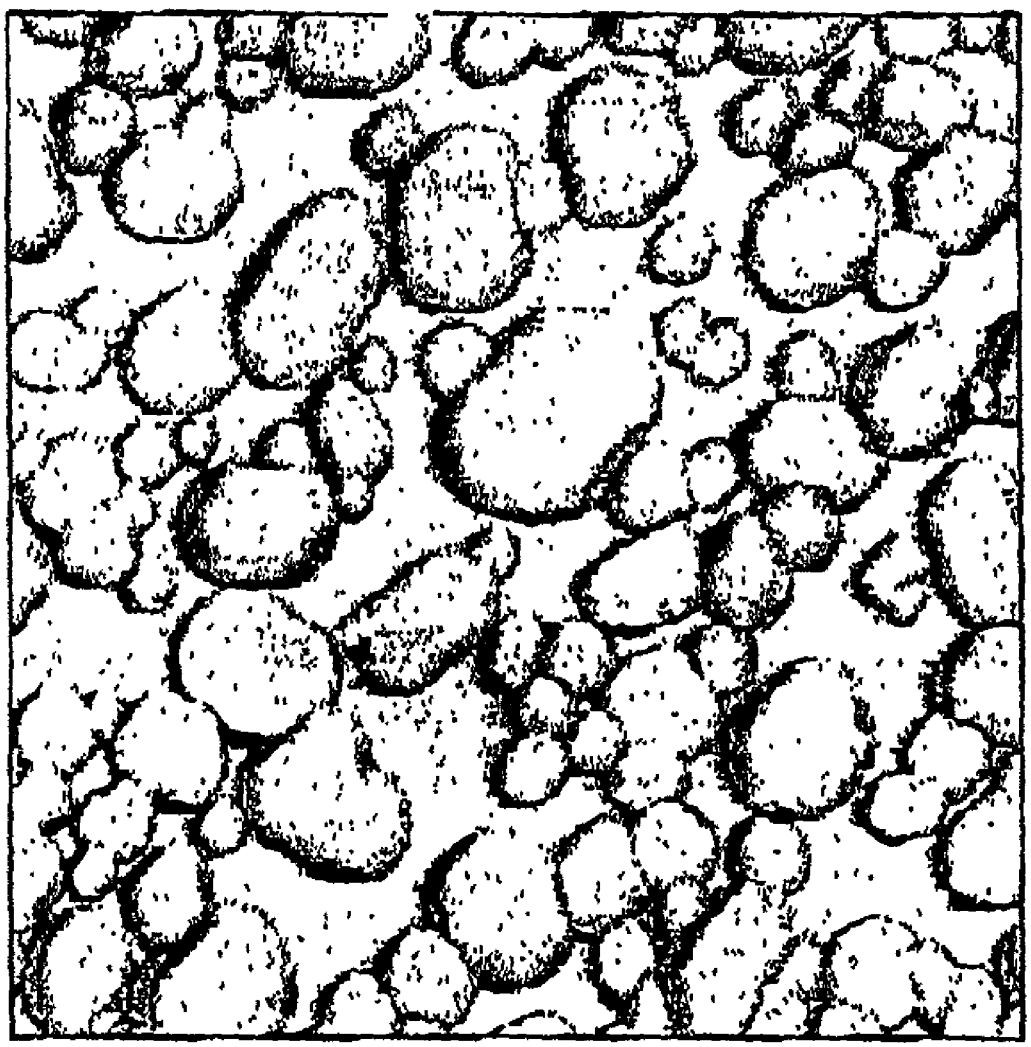
FIG. 4D is an image produced by tapping mode phase-shift scanning force microscopy of an annealed gold film of 100 Angstrom nominal thickness, in accordance with a preferred embodiment of the present invention.

Reference is now made to FIG. 4D, which is an image produced by tapping mode scanning force microscopic phase-shifting of an annealed gold film of 100 Angstrom nominal thickness, in accordance with a preferred embodiment of the present invention.

Gold islands of a nominal thickness 100 Å on a transparent substrate were prepared by standard methods described herein. The islands were annealed under standard conditions (see examples hereinbelow). The islands were viewed by phase-shift tapping mode SFM. The island faceting is well observed here (FIG. 4D).

Figure 4E:
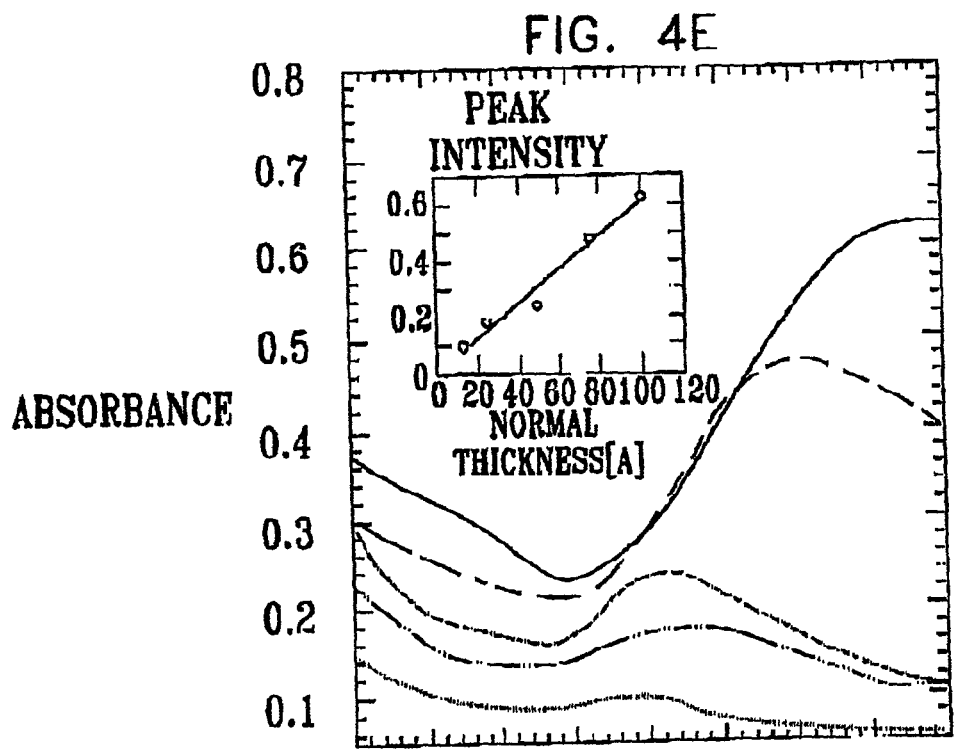
FIG. 4E displays a series of UV/visible/IR spectra of non-annealed ultra-thin gold films on mica, in accordance with a preferred embodiment of the present invention.
Figure 4F:
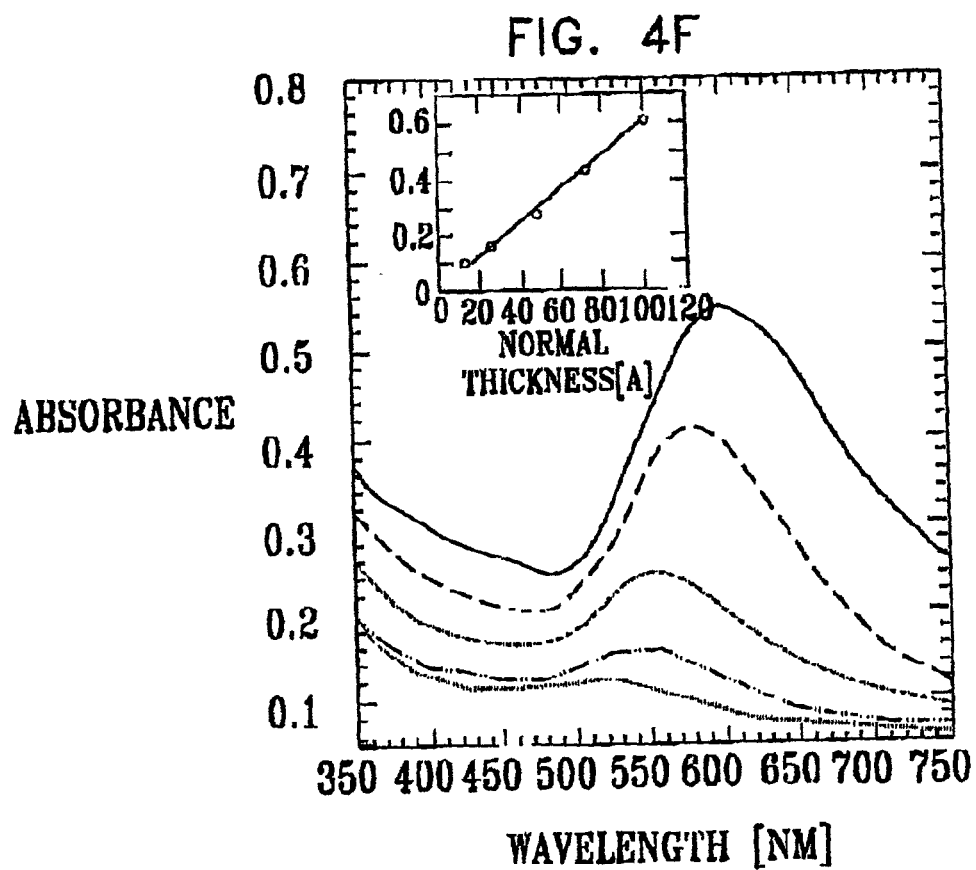
FIG. 4F displays a series of UV/visible/IR spectra of annealed ultra-thin gold films on mica, in accordance with a preferred embodiment of the present invention.

Reference is now made to FIG. 4E, which displays a series of UV/visible/IR spectra of non-annealed ultra-thin gold films on mica, and to FIG. 4F which displays a series of UV/visible/IR spectra of annealed ultra-thin gold films on mica, in accordance with preferred embodiments of the present invention.

The same gold films of islands as in FIGS. 4C/1-4C/10 were examined by transmission UV/vis spectroscopy. The spectra for the annealed films (FIGS. 4C/1-4C/5) demonstrate a defined gold surface plasmon band, shifting from 606 to 530 nm as the nominal thickness decreases from 100 Å to 13 Å, respectively. The intensity is nearly linearly correlated with the film nominal thickness (FIG. 4F, inset). The latter also applies to the non-annealed films (FIG. 4E), that show gold surface plasmon bands that are more intense and broader than the respective ones for the annealed films.

Reference is now made to FIGS. 4G/1-4G/12, which are a series of images produced by tapping mode scanning force microscopic topography of ultra-thin gold films on quartz, in accordance with a preferred embodiment of the present invention.

Figure 15:
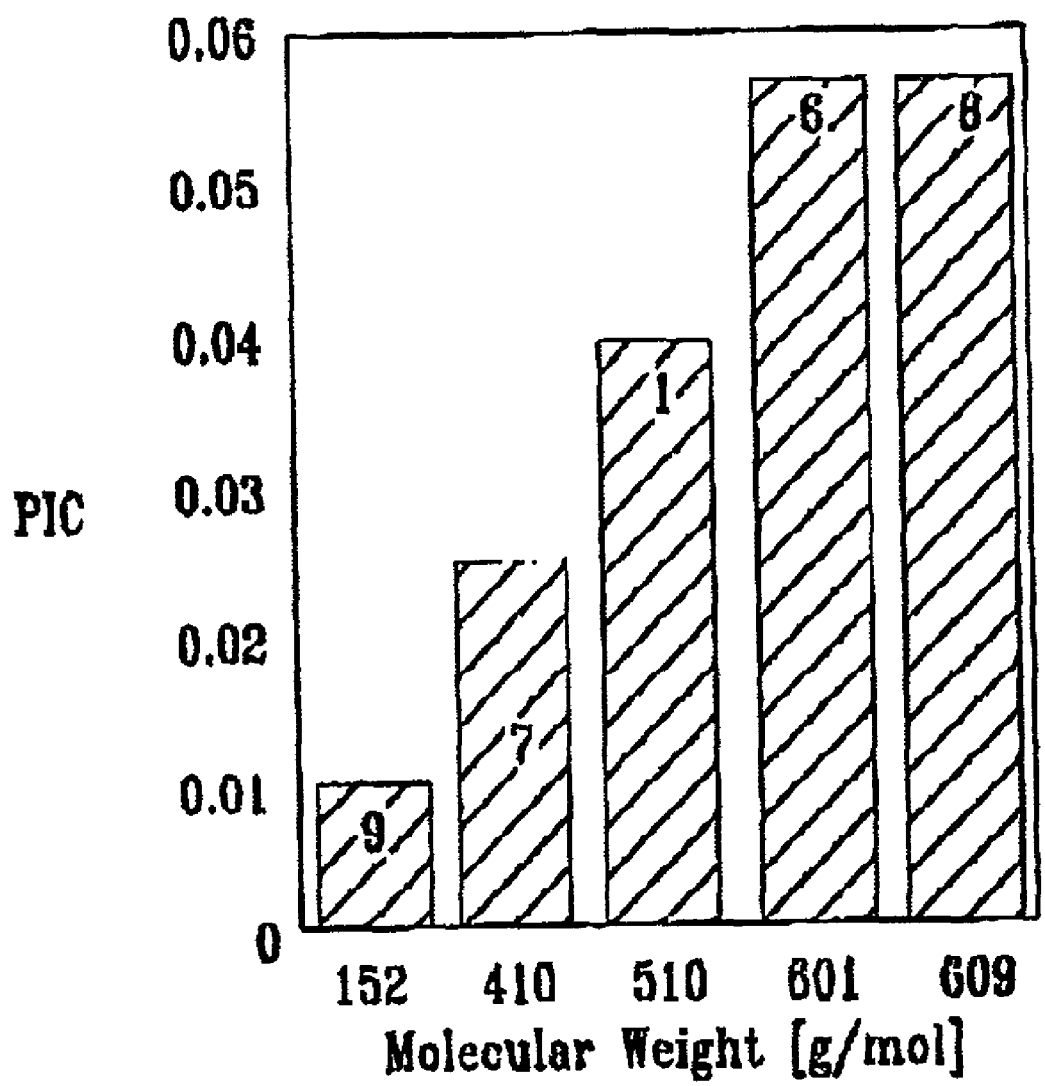
FIG. 15 is a graph showing the plasmon intensity change as a function of the molecular weight of ligands 1 and 6-9 (FIGS. 10A and 10B), in accordance with a preferred embodiment of the present invention.

A set of ultrathin gold films of nominal thickness 13, 25, 50 and 100 Å on quartz (transparent at wavelengths longer than 220 nm) was studied. SFM imaging of the ultrathin gold films on quartz shows essentially the same island structure, with a general dependence of the island size on the nominal thickness and a noticeable increase in the island diameter during annealing, as observed for the analogous films on mica (FIGS. 4G1-4G15). A more intensive annealing regime (12 h at 350° C.), did not result in noticeable changes in the size and separation of the islands, with the possible exception of the film with nominal thickness 100 Å.

Reference is now made to FIG. 4H, which is a series of UV/visible/IR spectra of non-annealed ultra-thin gold films on quartz, and to FIG. 4I which is a series of UV/visible/IR spectra of annealed ultra-thin gold films on quartz, in accordance with a preferred embodiment of the present invention.

The same gold films as shown in FIGS. 4G/1-4G/15 were examined by transmission UV/vis spectroscopy (FIGS. 4H-4I). Similarly to the films evaporated on mica shown in FIGS. 4E-4F), the spectra for the annealed and non-annealed films demonstrate a defined gold surface plasmon band. The band intensity is linearly correlated with the film nominal thickness (FIGS. 4H-4I, insets) for both annealed and non-annealed films in the thickness range 13-50 Å. The intensity for the 100 Å films shows a deviation, probably due to the longer evaporation times needed which is associated with certain induced annealing during evaporation. Analogously to the ultrathin films on mica, the surface plasmon band for the non-annealed films on quartz is more intense, broader and red shifted in comparison to the one for the annealed films.

Reference is now made to FIG. 5, which is a simplified flowchart depicting a method for producing metallic islands and annealing them on a transparent substrate and thereafter detecting and quantifying a chemical substance employing an optical property of the metallic islands, in accordance with a preferred embodiment of the present invention. This method is exemplified in Examples 2-4 hereinbelow.

In a production step 500, metallic islands on transparent substrate are prepared. This may be by sputtering, evaporation or any other deposition method as described hereinabove (FIG. 3A).

In an annealing step 510, metallic islands on transparent substrate are annealed. The annealing may be performed in situ in a metal evaporation or sputter machine. Additionally or alternatively, it may be performed in a standard oven. The annealing process typically comprises heating the substrate with the metallic islands for 0-24 hours at temperatures of 150-400° C. More preferably substrates are annealed at 250-350° C. for 2.5-12 hours.

In a transmission step 515, system 20 transmits radiation of 300-1100 nm wavelength through the plurality of metallic islands 58 on transparent substrate 52.

In a measuring step 520, the optical properties of the metallic islands are determined. This step is substantially similar to step 200 in FIG. 2.

Thereafter, in a production step 530, a chemical substance-metallic islands moiety is produced. This step may comprise at least one of a chemical reaction, a chemical adsorption process and a physical adsorption process, as described in FIG. 2, step 210.

In a transmission step 535, system 20 transmits radiation of 300-1100 nm wavelength through the chemical substance-metallic islands moiety 65 on transparent substrate 52.

Following this, in a measuring step 540, at least one measurement of an optical property of chemical substance-metallic islands moiety is made. This may be comprise use of a system, such as system 20 in FIG. 1.

In a comparison step 550, an optical property of chemical substance-metallic islands moiety is compared with the optical property of metallic islands. This step is substantially similar to step 230 in FIG. 2.

Thereafter, in a provision step 560, system 20 (FIG. 1) may provide a quantitative and/or qualitative indication of chemical substance-metallic islands moiety. This step may include provision of a quantitative and/or qualitative indication of at least one of the following: chemical substance-metallic islands moiety, a functionality thereof; the plurality of metallic islands, a functionality thereof, the chemical substance and a functionality thereof.

Figure 6:
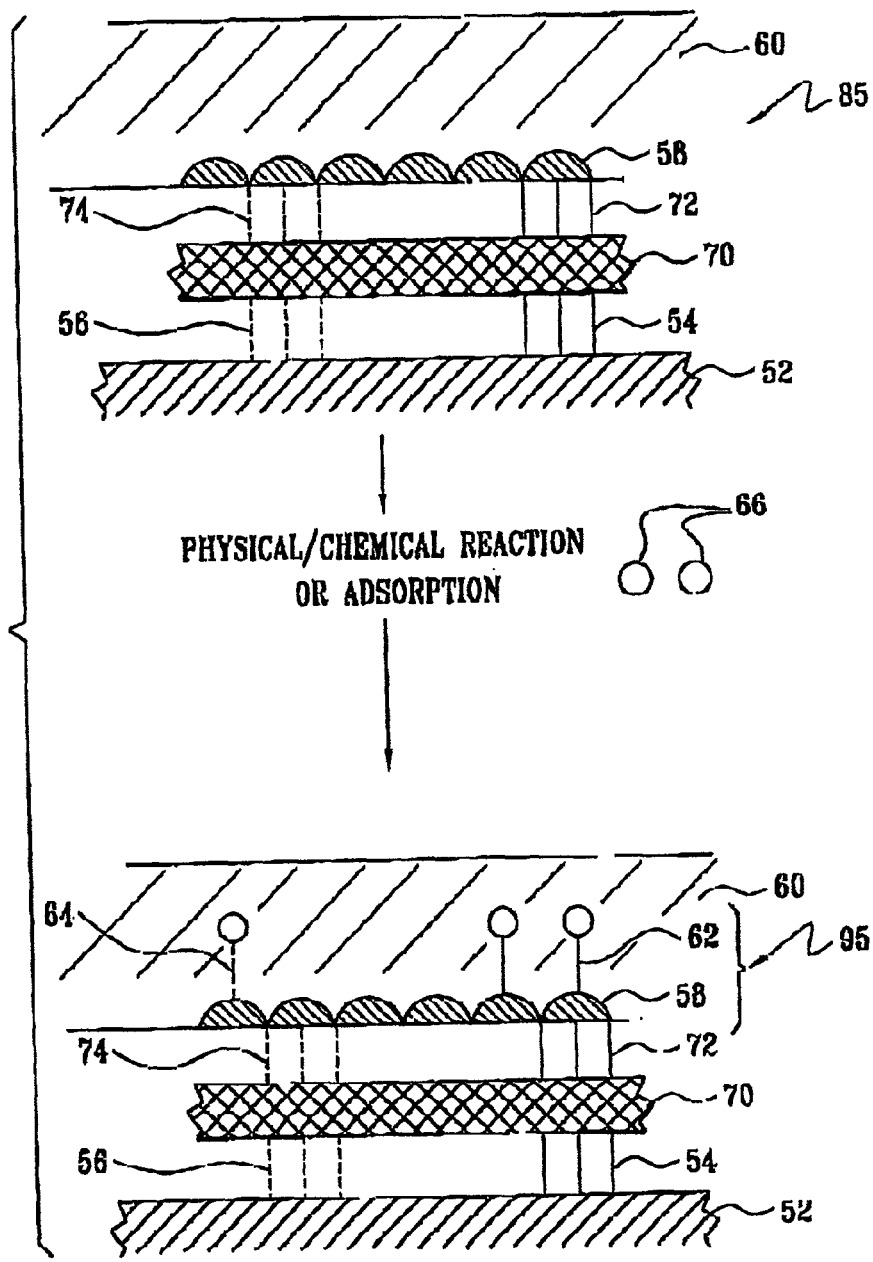
FIG. 6 are simplified pictorial illustrations showing a system of a chemical substance-metallic island moiety on an intermediate layer on a transparent substrate, in accordance with a preferred embodiment of the present invention.

Reference is now made to FIG. 6, which is a simplified pictorial illustration showing a system of a chemical substance-metallic island moiety on an intermediate layer on a transparent substrate, in accordance with a preferred embodiment of the present invention.

An intermediate layer 70 is adsorbed or reacted onto transparent substrate 52 by methods known in the art. This results in chemical bonds 54 or physical contact 56 communicating between the substrate and the intermediate layer. The intermediate layer may comprise one or more metals, one or more oxides, a polymeric material, an inorganic moiety or an organic moiety.

Thereafter metal islands are deposited onto the intermediate layer so as to produce one or more chemical bonds 72 and one or more physical contacts 74 between intermediate layer 70 and metallic islands 58. A chemical 66 is then chemically reacted or physically or chemically adsorbed onto metallic islands 58. This may take in a gaseous and/or liquid phase medium 60. Consequentially chemical 66 is bonded chemically by means of one or more chemical bonds 62 and/or adsorbed physically by one or more physical contacts 74 to metallic islands 58. Thus a system 85 comprising metallic islands 58 bound to intermediate layer 70 adsorbed onto transparent substrate 52 is formed.

Figure 7:
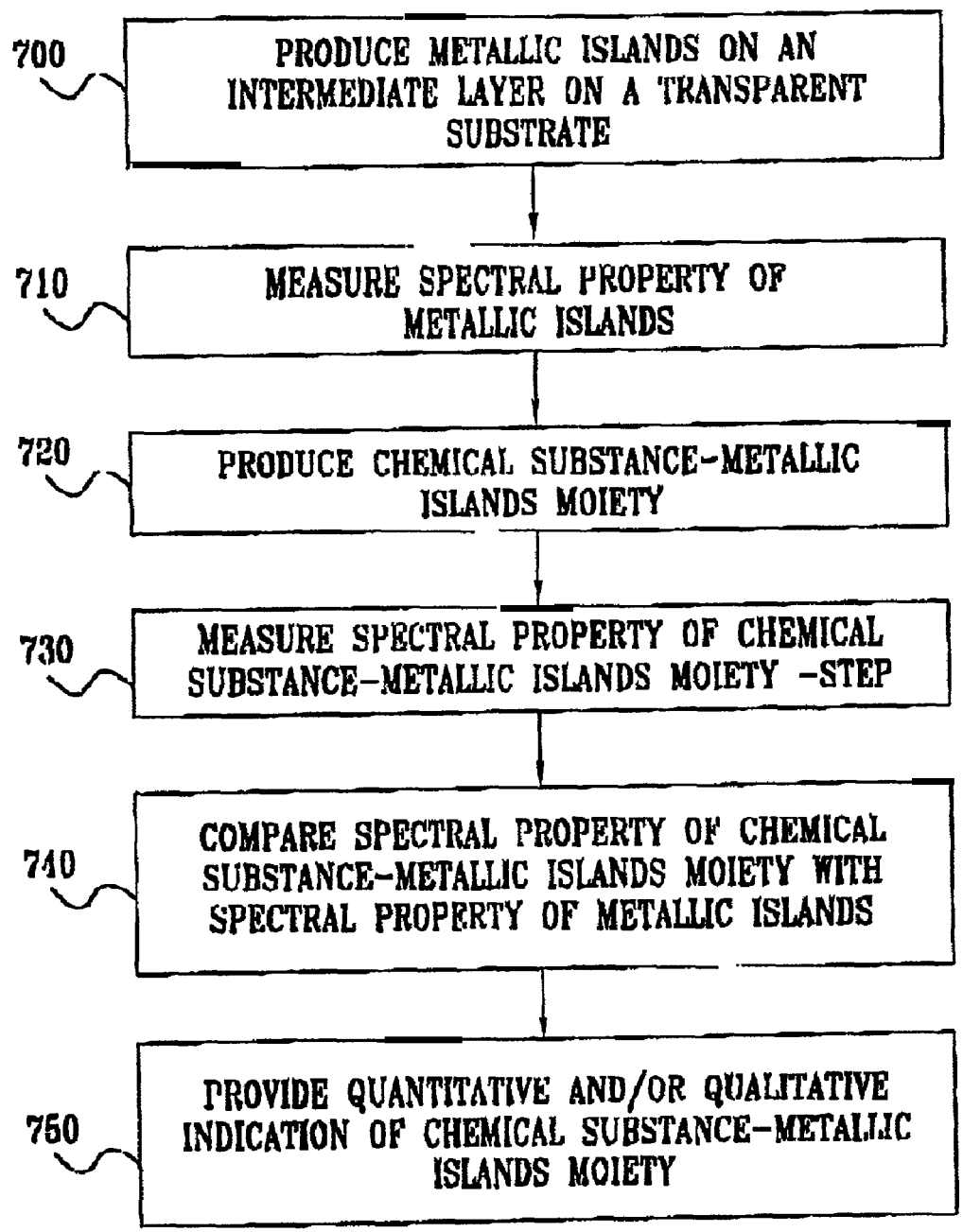
FIG. 7 is a simplified flowchart illustrating a method for producing the chemical substance-metallic island moiety on an intermediate layer on a transparent substrate of FIG. 6.

Reference is now made to FIG. 7, which is a simplified flowchart illustrating a method for producing the chemical substance-metallic island moiety on an intermediate layer on a transparent substrate of FIG. 6. This method is exemplified in Example 9 hereinbelow.

In a production step 700, metallic islands 58 are produced on intermediate layer 70 on transparent substrate 52. Transparent substrate may be any one of the substrates used in Examples 1-9 hereinbelow or may be any one or more of glass, plastic, polystyrene, a polymeric material, an inorganic material, quartz and mica. An example of production of an intermediate layer is provided in Example 9 hereinbelow.

In order to improve the adhesion between gold islands and the inorganic transparent substrate, an intermediate layer of oxides ($NiO$, $Cr_2O_3$, $TiO_2$) with thickness up to 5 nm may be deposited. Resistive evaporation of gold and/or other metals on these substrates is performed at rates 0.01-0.5 nm/s. Films with a gold layer thickness of less than 10 nm exhibit surface plasmon absorption band and are stable in organic as well as aqueous solutions.

Additionally or alternatively, improvement of the adhesion of gold to some substrates (e.g., glass, quartz) may also be obtained by silanization of the surface [Goss, C. A.; Charych, D. H.; Majda, M. *Anal. Chem.* 1991, 63, 85-88] prior to gold deposition. The parameters of gold deposition are the same as those for bare substrates.

In a transmission step 705, system 20 transmits radiation of 300-1100 nm wavelength through the plurality of metallic islands 58 and intermediate layer 70 on transparent substrate 52.

Thereafter, in a measuring step 710, an optical property of metallic islands on the intermediate layer on the transparent substrate is measured. This may be substantially similar to step 200 in FIG. 2. Typically, this measuring step is performed in a system such as system 20 of FIG. 1. Examples of the spectral properties are provided in FIGS. 4E & 4F hereinabove.

Additionally or alternatively, measuring step 710 may be performed by system 10 of FIG. 1C.

In a production step 720, a chemical substance-metallic islands moiety is produced. This step is substantially similar to step 210 in FIG. 2 hereinabove.

In a transmission step 725, system 20 transmits radiation of 300-1100 nm wavelength through the chemical substance-metallic islands moiety 65 on the intermediate layer 70 on transparent substrate 52.

In a measuring step 730, at least one optical property of a chemical substance-metallic islands moiety is measured. This is substantially similar to step 220 in FIG. 2 hereinabove. For example, an optical property of a monolayer of 8 adsorbed onto gold is measured The optical property may include an absolute spectrum (FIG. 12A hereinbelow).

In a comparing step 730, the optical property of the chemical substance-metallic islands moiety may be compared with the optical property of the metallic islands. Typically, a system such as system 20 (FIG. 1) provides difference spectra (obtained by subtraction of the 0 sec spectrum from the other spectra (as shown in FIGS. 12A-12D hereinbelow)).

In a provision step 750, a system such as system 20 (FIG. 1) provides a quantitative and/or qualitative indication of chemical substance-metallic islands moiety.

Additionally or alternatively, the system may provide a qualitative and/or quantitative indication of at least one of the chemical substance-metallic islands moiety, a functionality thereof; the plurality of metallic islands, a functionality thereof, the chemical substance and a functionality thereof.

Figure 8A:
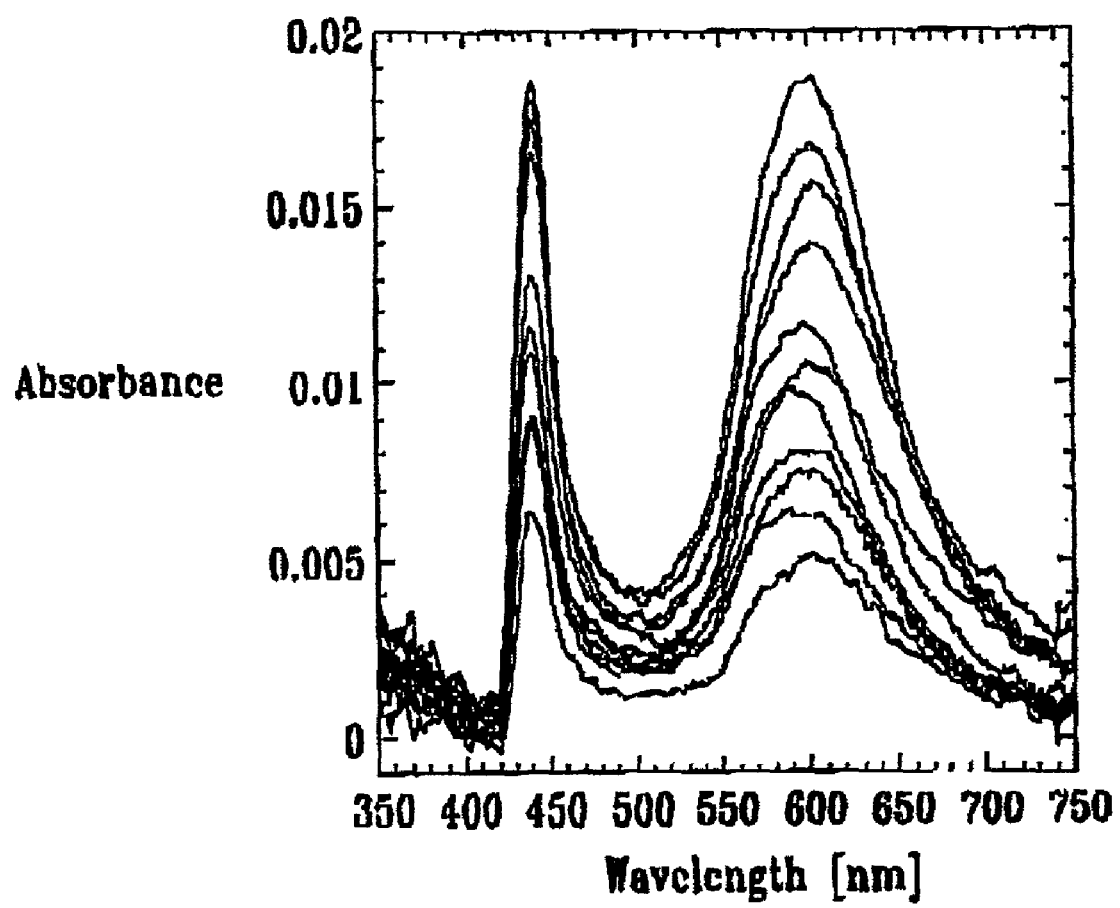
FIG. 8A is a series of successive UV/visible/IR spectra of cobalt tetraphenylporphyrin adsorbed onto a self-assembled monolayer of ligand 1, in accordance with a preferred embodiment of the present invention.

Reference is now made to FIG. 8A, which is a series of successive UV/visible/IR spectra of cobalt tetraphenylporphyrin adsorbed onto a self-assembled monolayer of ligand 1, in accordance with a preferred embodiment of the present invention. The gold island films were 25 Å (nominal thickness), evaporated on mica and annealed. All the samples were treated (washed, dried etc. as described hereinbelow (Example 1). FIG. 8A shows successive UV/vis spectra of CoTPP adsorbed onto a SAM of 1 from 1 mM solution in $CHCl_3$ for 1-540 s Successive UV/vis spectra of CoTPP adsorbed onto a SAM of 1 from 1 mM solution in $CHCl_3$ for 1-540 s. The methodology for measuring sequential spectra is both convenient and provides speedy UV/visible/IR measurements.

This methodology combined with sub-monolayer sensitivity achieved with gold island film substrates, provides a powerful mechanistic tool for analyzing, detecting and quantifying processes involving assembly or manipulation of monolayers containing chromophores. This is exemplified here using the process of CoTPP binding to a 1 monolayer on Au (FIG. 8A).

Figure 8B:
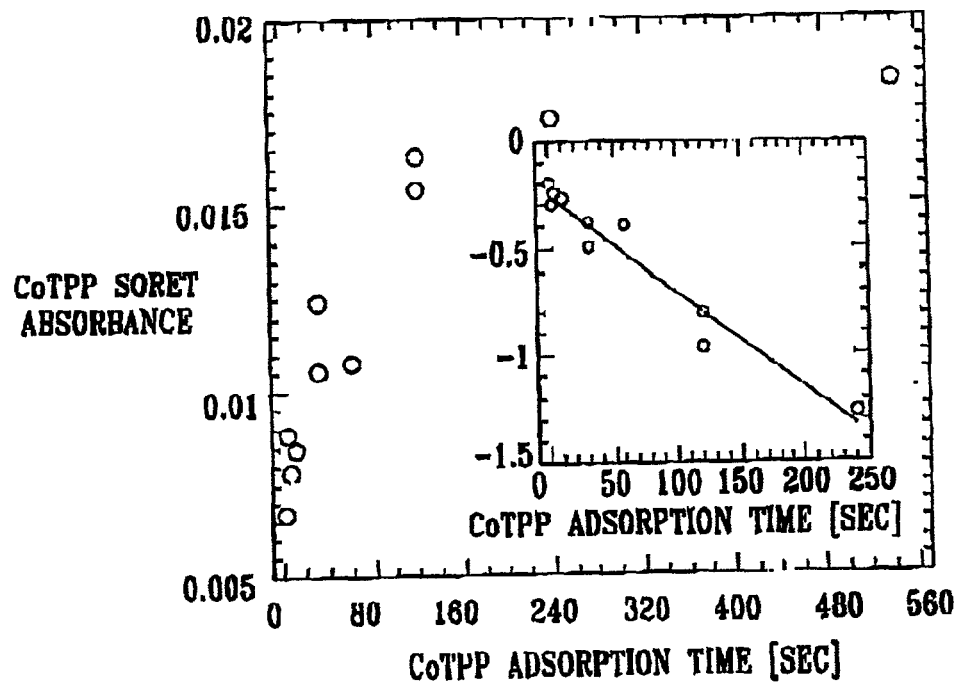
FIG. 8B is a graph showing the kinetics of tetraphenylporphyrin binding to the self-assembled monolayer of ligand 1, in accordance with a preferred embodiment of the present invention.

Reference is now made to FIG. 8B, which is a graph showing the kinetics of tetraphenylporphyrin binding to the self-assembled monolayer of ligand 1, in accordance with a preferred embodiment of the present invention. The high intensity of the Soret band of the 1-CoTPP SAMs on Au island films allows to monitor the kinetics of the process of chromophore binding to the monolayer on Au, as shown in FIG. 8A hereinabove. A plot of the CoTPP adsorption time against the CoTPP Soret absorbance shows typical first order saturation kinetics. The inset in FIG. 8B shows that the kinetics of the binding process follows first-order reaction kinetics.

Figure 8C:
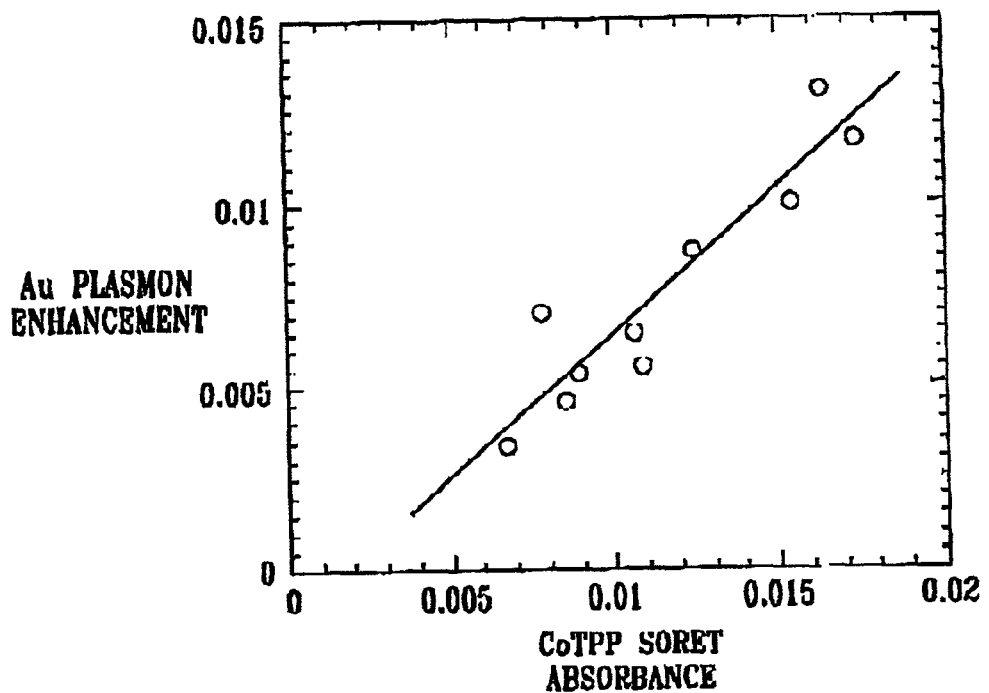
FIG. 8C is a graph depicting a correlation between the CoTPP Soret band absorbance and the enhanced plasmon absorbance, in accordance with a preferred embodiment of the present invention.

Reference is now made to FIG. 8C is a graph depicting a correlation between the CoTPP Soret band absorbance and the enhanced plasmon absorbance, in accordance with a preferred embodiment of the present invention.

The gold surface plasmon enhancement induced by the SAM is seen here rather prominently (FIG. 8C), as a linear correlation between the Soret band intensity of the CoTPP (i.e., the quantity of adsorbed CoTPP) and the Au surface plasmon enhancement, for the spectra in FIG. 8A. Thus it is proved here that the gold plasmon enhancement absorbance value may be used to indicate a quantity of the chemical substance bound on the metallic islands. This may be restated more generally, that the metallic plasmon enhancement absorbance measurement can be used as a quantitative tool indicating the amount of the chemical substance bound or adsorbed to the metallic islands. Further aspects of this methodology are further described in FIG. 17 and Examples 2 and 4 hereinbelow.

Figure 9A:
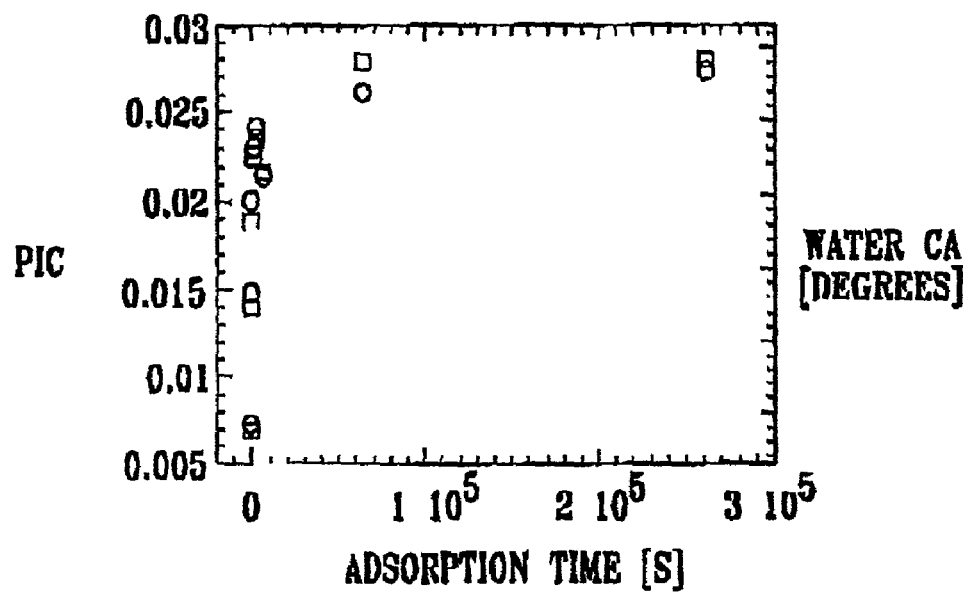
FIG. 9A is a graph depicting the kinetics of formation of a self assembled monolayer of ligand 6 adsorbed from a 2 mM solution of trichloromethane, showing the contact angle (CA) and the plasmon intensity change (PIC) of the gold islands, in accordance with a preferred embodiment of the present invention.

Reference is now made to FIG. 9A, which is a graph depicting the kinetics of formation of a self assembled monolayer of ligand 6 adsorbed from a 2 mM solution of trichloromethane, showing the contact angle (CA) and the plasmon intensity change of the gold islands, in accordance with a preferred embodiment of the present invention.

Figure 9B:
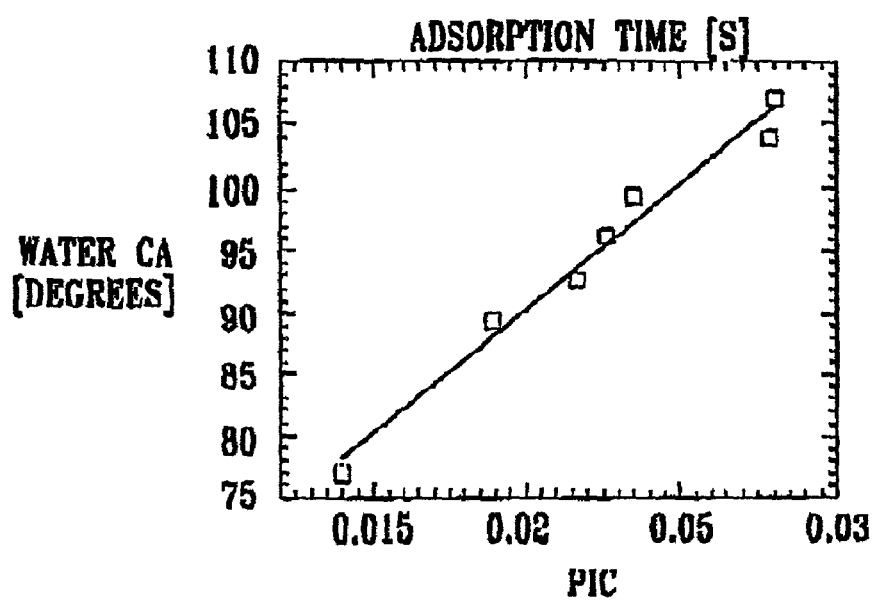
FIG. 9B is a graph showing a correlation of the plasmon intensity change as a function of the water contact angle of the gold islands of FIG. 9A.

Reference is now made to FIG. 9B, which is a graph showing a correlation of the plasmon intensity change as a function of the water contact angle of the gold islands of FIG. 9A. It is seen that there is a linear correlation between the PIC and water CAs. All the experimental points were measured on the same sample. The line shown in FIG. 9B is a linear fitting of the experimental data (from FIG. 9A). The gold substrate was 25 Å (nominal thickness) on quartz, and was annealed.

This correlation indicates that the PIC measurements may be used to give a quantitative indication of the concentration of the chemical substance.

Figure 10A:
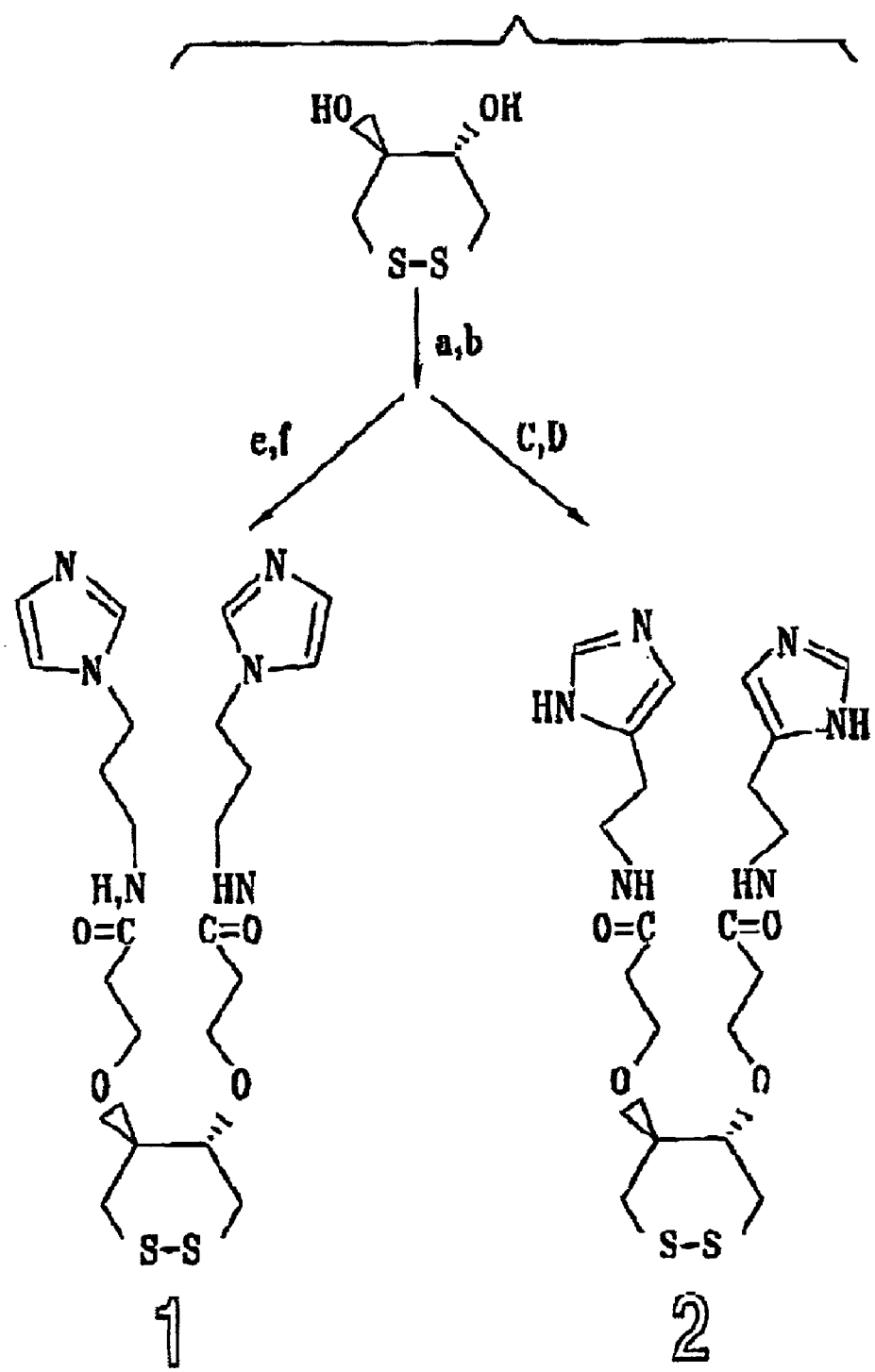
FIG. 10A is a schematic presentation of the synthesis of molecules 1 and 2 as is known in the art.

Reference is now made to FIG. 10A, which is a schematic presentation of the synthesis of molecules 1 and 2 as is known in the art. Molecule 1 is (CAS#227604-62-8):Propanamide, 3,3'-[[(4R,5R)-1,2-dithiane-4,5-diyl]bis(oxy)]bis[N-[3-(1H-imidazol-1-yl)propyl]-,rel-(9CI). Molecule 2 is (CAS#227604-63-9): Propanamide,3,3'-[[(4R,5R)-1,2-dithiane-4,5-diyl]bis(oxy)]bis[N-[3-(1H-imidazol-4-yl)propyl]-,rel-(9CI).

Reference is now made to FIG. 10B, which is a schematic representation of molecules 6-9 as is known in the art. Molecule 6 is (CAS# unknown):1,2-Dithiane-4,5-diol, dipentadecanoate, trans-.

Molecule 7 is (CAS# unknown): 1,2-Dithiane-4,5-diol, di(4-cyanobenzoate),trans-.

Molecule 8 is (CAS# unknown) 1,2-Dithiane-4,5-diol, di(2-pyrenecarboxilate), trans-.

Molecule 9 is (CAS# 14193-38-5) trans-1,2-Dithiane-4,5-diol.

Monolayers of $C_{16}H_{34}S$ and $C_{10}H_{22}S$ were adsorbed by immersion of gold substrates in a 2 mM solution in EtOH.

Monolayers of 1 or 2 were adsorbed by immersion of gold substrates in a 1-10 mM solution in $CHCl_3$ or DMF for 20 min to 15 h.

CoTPP was bound from $CHCl_3$ solutions. The slides were rinsed successively with dry chloroform and absolute ethanol and dried under a stream of purified nitrogen. Physically deposited layers were formed by applying several drops of the substance solutions onto the substrate surface followed by drying under a stream of purified air or nitrogen.

Monolayers of 6-8 were adsorbed by immersion of gold substrates in a 2 mM solution of the corresponding molecule in $CHCl_3$ for various times.

All the monolayers were rinsed successively with dry chloroform (or another solvent used for the adsorption) and absolute ethanol, then dried under a stream of purified air or nitrogen. Physically deposited layers were formed by applying several drops of the substance solutions onto the substrate surface followed by drying under a stream of purified air or nitrogen.

Reference is now made to FIG. 11A, which is a series of successive UV/visible/IR spectra of self-assembled monolayers of ligand 1 adsorbed from a 0.4 mM solution of trichloromethane, in accordance with a preferred embodiment of the present invention. UV/visible/IR spectra of self-assembled monolayers (SAMs) of 1 were adsorbed from 0.4 mM solution in $CHCl_3$ for 1 s-180 min.

The use of the surface plasmon intensity change (or PIC) for studying self-assembly of molecules that do not absorb light in the UV/visible/IR range is exemplified by monitoring the adsorption kinetics of a monolayer of 1 (which is transparent in the visible region), as shown in FIG. 11A.

Reference is now made to FIG. 11B, which is a series of successive UV/visible/IR spectra of cobalt tetraphenylporphyrin adsorbed onto a self-assembled monolayer of ligand 1, in accordance with a preferred embodiment of the present invention. FIG. 11B shows UV/visible/IR spectra of CoTPP bound to the SAMs of 1 from 1 mM solution in $CHCl_3$ for 10 min.

Reference is now made to FIG. 11C, which is a graph showing the relation between adsorption times and the normalized quantities of absorption bands of a) plasmon intensity change after adsorption of ligand 1 of FIG. 11A [triangles], b) the plasmon intensity change accompanying CoTPP binding to the self-assembled monolayer of 1 as in FIG. 11B [squares], and Soret band adsorbance after adsorption of CoTPP onto the self-assembled monolayer of ligand 1 of FIG. 11B.

As seen in FIG. 11C, plotting both the increase of the gold plasmon absorption (associated with the adsorption of 1) and the Soret band absorption of bound CoTPP vs. adsorption time shows very similar kinetics. The same dependance is observed when plotting the additional enhancement of the gold plasmon resulting from CoTPP binding (FIG. 11C). This correlation demonstrates the potential of this technique for the construction of molecular sensors, since, e.g., here the SAM of 1 may be considered a sensor for CoTPP. One may conclude from FIGS. 9A-9C that self-assembled monolayer of ligands such as 1, may be used in apparatus and methods for detection and/or quantification of chemical substances such as CoTPP. The apparatus may include machines and instrumentation such as a spectrophotometer. Additionally or alternatively, the apparatus may comprise a kit or a sensor.

Reference is now made to FIG. 12A, which is a series of absolute transmission UV/visible/IR spectra for the formation of a monolayer of ligand 8 on a non-annealed gold substrate, in accordance with a preferred embodiment of the present invention.

FIG. 12A displays absolute transmission spectra in the UV/visible/IR range for monitoring the formation of a monolayer of 8 on an non-annealed Au substrate (25 Å nominal thickness, evaporated on quartz), adsorbed from 2 mM solution of 8 in chloroform.

Figure 12B:
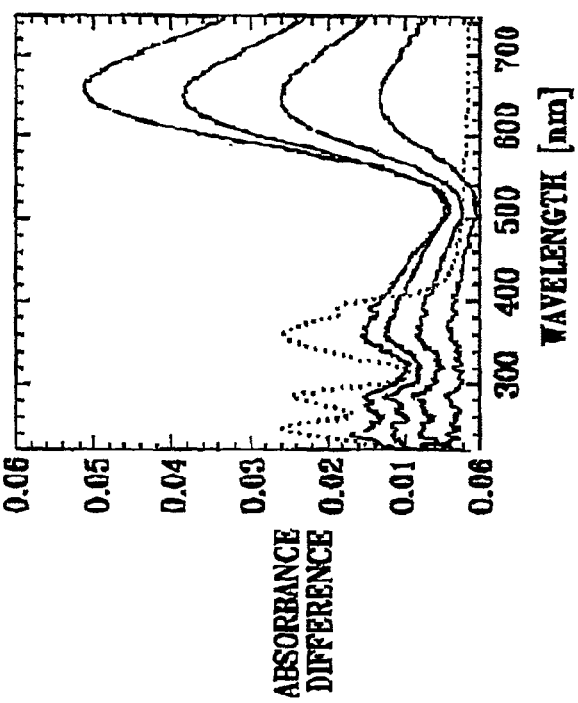
FIG. 12B is a series of difference transmission UV/visible/IR spectra for the formation of a monolayer of ligand 8 on a non-annealed gold substrate, in accordance with a preferred embodiment of the present invention.

Reference is now made to FIG. 12B, which is a series of difference transmission UV/visible/IR spectra for the formation of a monolayer of ligand 8 on a non-annealed gold substrate, in accordance with a preferred embodiment of the present invention. FIG. 12B displays difference spectra obtained by subtraction of the 0 sec spectrum from the other spectra in FIG. 12A. The dashed line corresponds to the spectrum of a thick layer of 8, obtained by evaporation of a drop on quartz (original spectrum divided by 6.

Self-assembled monolayers of 8. The molecule 8 shown in FIG. 10B is also used here to demonstrate the validity and generality of the method, possesses two pyrene residues showing three intense absorption bands in the UV region, while in the visible range the molecule is nearly transparent (FIG. 12B, dashed line). It enables to determine directly the amount of adsorbed molecules by the intensity of these three UV absorption bands, while simultaneously following changes in the gold surface plasmon absorption accompanying molecular binding to the gold.

The series of transmission UV/visible/IR absolute spectra (FIG. 12A) and difference spectra (FIG. 12B) spectra of a 25 Å Au island film show the changes observed during formation of a monolayer of 8. The self-assembly process (FIG. 12A) is accompanied by an increase of the chromophore absorption bands in the UV range, and an increase and a red shift of the Au surface plasmon absorption band around 600 nm. The concurrent development of the pyrene bands and the Au surface plasmon absorption is seen more clearly in the differential plasmon spectroscopy (DPS) presentation (FIG. 12B), obtained by subtracting the background spectrum (0 s in FIG. 12A).

Figure 12D:
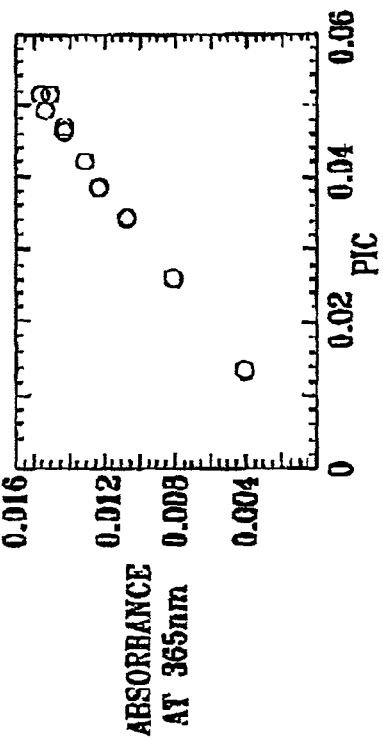
FIG. 12D is a graph showing a correlation between the plasmon intensity change and the maximum absorbance of ligand 8, in accordance with a preferred embodiment of the present invention.
Figure 12A:
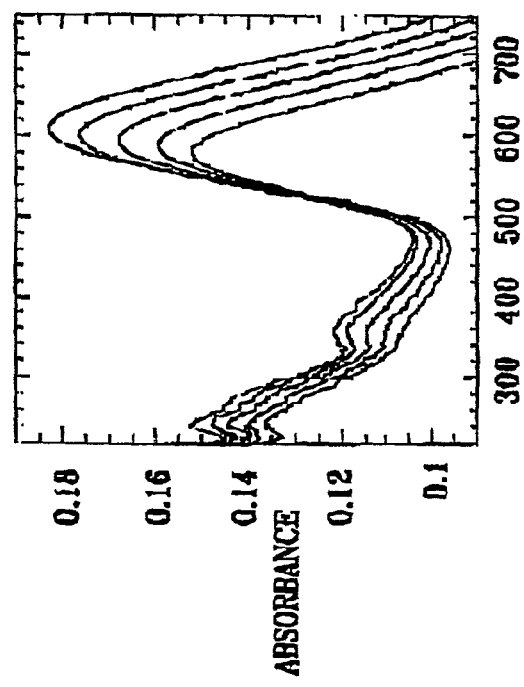
FIG. 12A is a series of absolute transmission UV/visible/IR spectra for the formation of a monolayer of ligand 8 on a non-annealed gold substrate, in accordance with a preferred embodiment of the present invention.
Figure 12C:
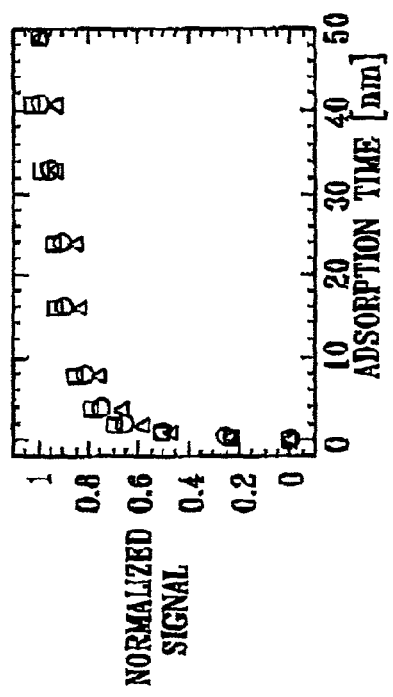
FIG. 12C is a graph showing a correlation of the normalized quantities of the plasmon absorbance with respect to the adsorption time, in accordance with a preferred embodiment of the present invention.

Reference is now made to FIG. 12C, which is a graph showing a correlation of the normalized quantities of the plasmon absorbance with respect to the adsorption time, in accordance with a preferred embodiment of the present invention. As shown in FIG. 12C, the absolute plasmon intensity and position (FIG. 12A) as well as the plasmon intensity change (FIG. 12B) may be used to monitor the binding of the molecule to the gold, showing essentially identical behavior. Quantitative determination of the intensity change may be more accurate than that of either the absolute intensity or the position of the plasmon band.

Reference is now made to FIG. 12D, which is a graph showing a correlation between the plasmon intensity change and the maximum absorbance of ligand 8, in accordance with a preferred embodiment of the present invention.

FIG. 12D shows a linear relationship with a low standard deviation between the plasmon intensity change and the intensity of the pyrene band, indicating that the intensity change is linearly correlated with the amount of molecules bound to the Au surface. This relationship, not previously shown, forms the basis for application of using gold island films as optical sensors using Au surface plasmon absorption measurements. As seen in FIG. 12D, the sensitivity of the method is ca. 2% of a monolayer. A similar sensitivity is observed with other molecules studied by this method (see hereinabove and hereinbelow). One may conclude from FIG. 12A-12D that the linear relationship between the plasmon intensity change of gold islands, against the absorbance of molecules such as 8 provides a linear correlation. Thus, this linear correlation may be used to quantify the adsorption of molecules such as 8 onto metallic islands. This phenomenon may be applied in apparatus and methods for measuring detection and/or quantification of chemical substances such as 8. The apparatus may include machines and instrumentation such as a spectrophotometer. Additionally or alternatively, the apparatus may comprise a kit or a sensor.

Figure 13A:
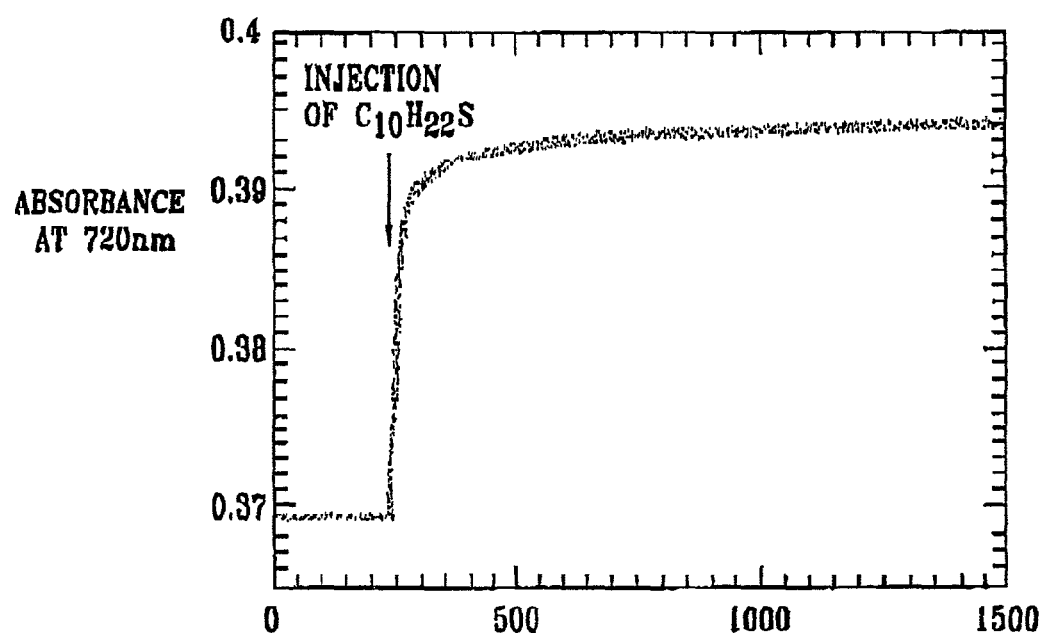
FIG. 13A is a graph depicting the kinetics of formation of a self-assembled monolayer of $C_{10}H_{22}S$ on a gold film on mica from trifluorpropanol in a liquid phase, in accordance with a preferred embodiment of the present invention.

Reference is now made to FIG. 13A, which is a graph depicting the kinetics of formation of a self-assembled monolayer of $C_{10}H_{22}S$ on a gold film on mica from trifluorethanol in a liquid phase, in accordance with a preferred embodiment of the present invention. A 50 Å non-annealed gold film was evaporated on mica from 2 mM solution in $CF_3CH_2OH$. The absorbance at 720 nm is shown as a function of time. The arrows indicate the time of injection.

Figure 13B:
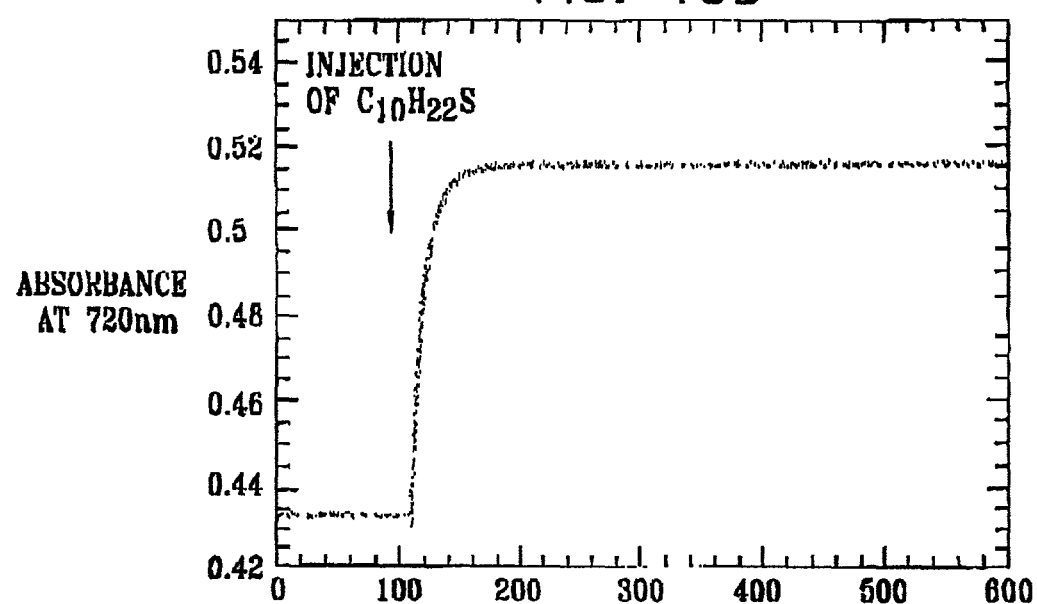
FIG. 13B is a graph depicting the kinetics of formation of a self-assembled monolayer of $C_{10}H_{22}S$ on a gold film on mica from a gaseous phase, in accordance with a preferred embodiment of the present invention.

PIC measurements may also be applied for in situ quantitative monitoring of adsorption on gold. FIGS. 13A & 13B show the kinetics of formation of a SAM of 1-decanethiol ($C_{10}H_{22}S$) on a 50 Å non-annealed Au island film evaporated on mica, from solution and gas phase.[100] The measurement was carried out by monitoring the absorbance at a fixed wavelength (720 nm for the measurements shown in FIGS. 13A & 13B) chosen to be as close as possible to the plasmon intensity change (PIC) maximum. A fairly steady baseline surface plasmon absorption at 720 nm (0-250 s in FIG. 13B and 0-100 s in FIG. 13b) implies stability of the ultrathin gold film both in 2,2,2-trifluoroethanol (TFE) and in air and absence of impurities. Injection of $C_{10}H_{22}S$ results in an increase of the absorption at 720 nm, rapidly reaching a steady state. The value of the PIC (at 720 nm) accompanying $C_{10}H_{22}S$ adsorption from gas phase is several times greater than the one obtained in solution (compare FIGS. 13A & 13B).

Reference is now made to FIG. 13B, which is a graph depicting the kinetics of formation of a self-assembled monolayer of $C_{10}H_{22}S$ on a gold film on mica from a gaseous phase, in accordance with a preferred embodiment of the present invention. A 50 Å non-annealed gold film was evaporated on mica from a gas phase. The absorbance at 720 nm is shown as a function of time. The arrows indicate the time of injection.

Figure 14A:
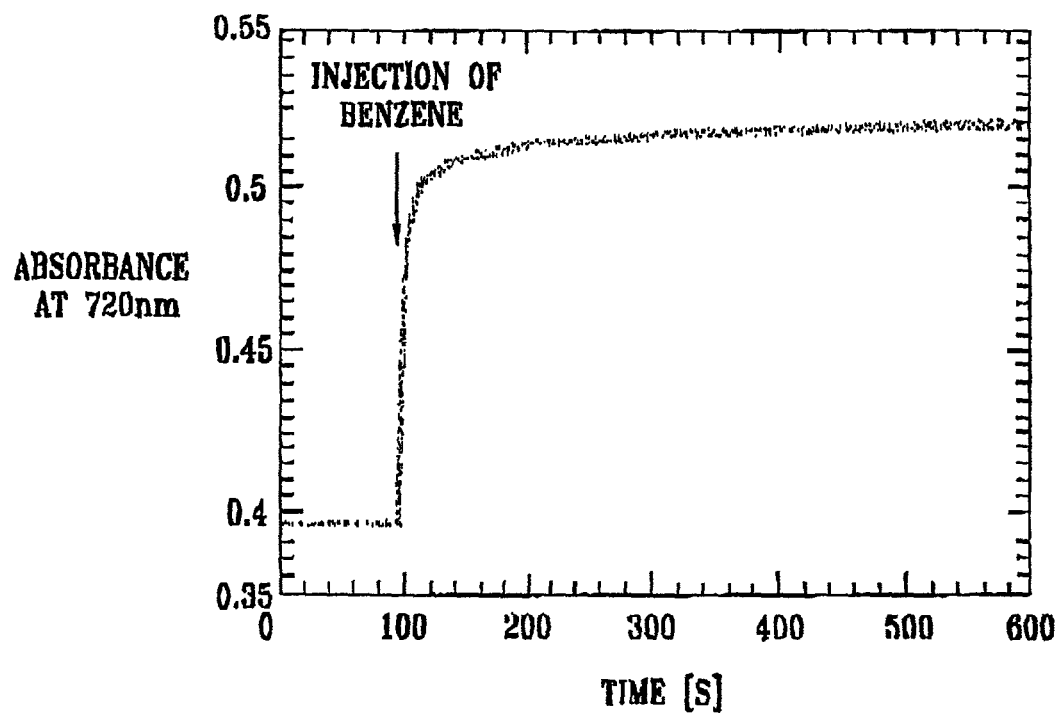
FIG. 14A is a graph depicting the kinetics of adsorption from a gas phase of benzene on a non-annealed gold film on mica, in accordance with a preferred embodiment of the present invention.

Reference is now made to FIG. 14A, which is a graph depicting the kinetics of adsorption from a gas phase of benzene of a non-annealed gold film on mica, in accordance with a preferred embodiment of the present invention. FIG. 14A shows kinetics of adsorption from gas phase of benzene to a 50 Å non-annealed Au film evaporated on mica. The absorbance at 720 nm is shown as a function of time. The arrow indicate the time of injection.

Figure 14B:
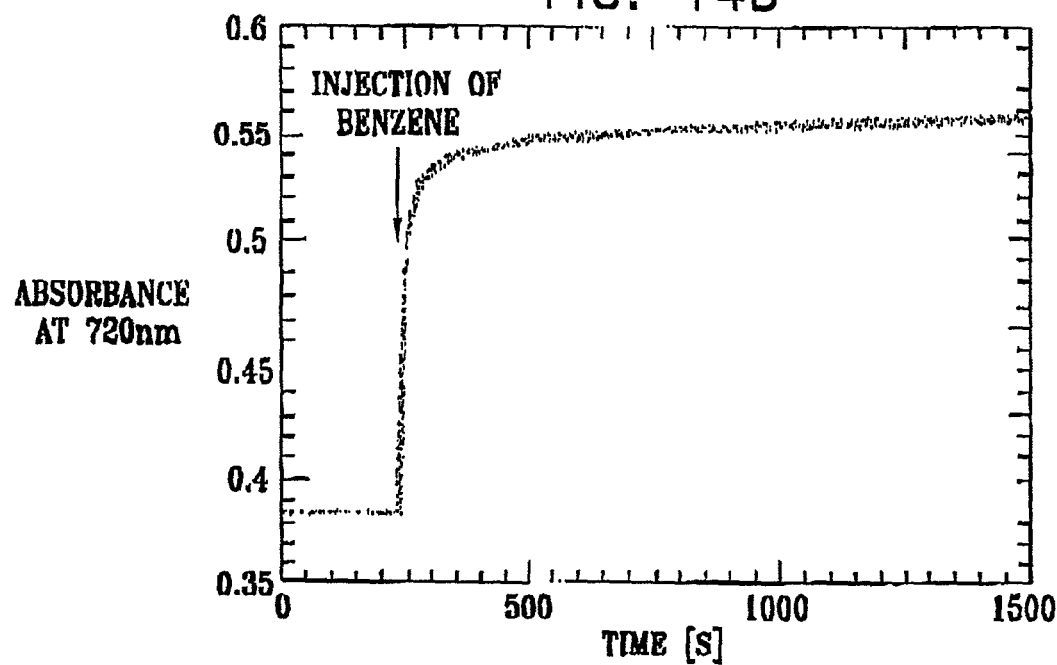
FIG. 14B is a graph depicting the kinetics of adsorption of pyridine onto a 50 angstrom non-annealed gold layer on mica, in accordance with a preferred embodiment of the present invention.

Reference is now made to FIG. 14B, which is a graph depicting the kinetics of adsorption of pyridine onto a 50 angstrom non-annealed gold layer on mica, in accordance with a preferred embodiment of the present invention.

FIG. 14B shows kinetics of adsorption from gas phase of pyridine to a 50 Å non-annealed Au film evaporated on mica. The absorbance at 720 nm is shown as a function of time. The arrow indicate the time of injection.

In situ measurements of PIC of Au island films also allow to monitor physical adsorption of various substances. Such measurements are impossible in ex situ arrangement, since physically adsorbed molecules desorb upon exposure of the interface to the ambient. The possibility to monitor the physical adsorption was exemplified by following the adsorption from gas phase of pyridine and benzene onto 50 Å non-annealed Au films evaporated on mica (FIGS. 14A & 14B). The steady state for benzene adsorption is reached faster than for pyridine, which correlates with the lower boiling temperature of benzene ($T_b$=80.1° C. for benzene, $T_b$=115.6° C. for pyridine). It is possible that more than one monolayer is formed here of benzene and pyridine, as in the case of adsorption of $C_{10}H_{22}S$.

Analogous in situ measurements either in solution or in gas phase for 1-hexadecanethiol ($C_{16}H_{34}S$), 4ATP and for a number of cyclic disulfides (not shown) showed similar results to those obtained for benzene and pyridine (FIGS. 14A & 14B).

The morphology of ultrathin gold island films (and hence their optical properties) are strongly dependent of preparation conditions such as nominal thickness and annealing regime. In order to find the optimal parameters for monitoring molecular self-assembly with maximal sensitivity and reproducibility, a set of ultrathin gold films with nominal thickness of 13, 25, 50 and 100 Å were studied as substrates for SAMs of 6, prepared under identical adsorption conditions (Table 2). Part of the slides were annealed for 4 h at 250° C.

As seen from Table 2 below, the PIC (and hence, the sensitivity) obtained with non-annealed gold films is considerably greater than the one for annealed films. For non-annealed gold films it increases with nominal thickness (reaching a plateau at 100 Å). For annealed films the PIC reaches a maximum at 50 Å. The smaller PIC values with the annealed films lead to lower reproducibility (compared with non-annealed films), becoming unreliable at 100 Å. The maximal sensitivity (obtained with the non-annealed gold film with nominal thickness of 100 Å) is 0.7% of a monolayer, a value comparable to the sensitivity of SPR spectroscopy. Annealed gold films would be better substrates for transmission UV/vis spectroscopy of SAMs, as the lower gold absorption provides better resolution of the monolayer absorption. Annealed gold films are also more stable with respect to rinsing with organic solvents.

TABLE 2

Comparison of PIC response obtained with various gold island films for the formation of a SAM of 6, adsorbed from 2 mM solution in $CHCl_3$.

| Nominal thickness... | Annealing regime | PIC maximum (average of 4 samples) | Standard deviation, % | Sensitivity, % of monolayer |
|---|---|---|---|---|
| 13 | Non-annealed | 0.021 | 7 | 5 |
|  | 4 h at 250° C. | 0.005 | 4 | 20 |
| 25 | Non-annealed | 0.057 | 7 | 2 |
|  | 4 h at 250° C. | 0.010 | 18 | 10 |
| 50 | Non-annealed | 0.121 | 9 | 0.8 |
|  | 4 h at 250° C. | 0.012 | 13 | 8 |
| 100 | Non-annealed | 0.148 | 4 | 0.7 |
|  | 4 h at 250° C. | 0.005 | 78 | 20 |

Reference is now made to FIG. 15, which is a graph showing the plasmon intensity change as a function of the molecular weight of ligands 1 and 6-9 (FIGS. 10A and 10B), in accordance with a preferred embodiment of the present invention.

FIG. 15 shows a comparison of PIC response obtained for SAMs of molecules 1, 6-9 adsorbed from 2 mM solutions in $CHCl_3$ (1, 6-8) or in $CHCl_3$/EtOH (1:1) (9) for 40 min. The shown PIC values are averages of the PIC obtained for 4 samples. The Au substrates were 25 Å (nominal thickness), evaporated on mica and non-annealed. All the samples were treated (washed, dried etc.) in the same way.

It appears that the PIC response for SAMs of different molecules should be generally different. Except for surface coverage (that obviously should affect the PIC), other factors that theoretically may affect the PIC response are refractive index, dipole moment, molecular size, presence/absence of an electron λ-system, intensely absorbing groups, etc. In order to get an indication on which of the above factors influence the PIC most, the cyclic disulfides 1 (FIG. 10A) and 6-9 (FIG. 10B) were adsorbed from 2 mM solutions for the same time (40 min; in the experiments mentioned above it was shown that the time is sufficient to obtain 95% of a monolayer coverage). This comparison provides only qualitative results since the surface coverage may vary for different molecules; however, the presence of the cyclic disulfide group in all the molecules allows to assume that the difference in the surface coverage is not high. FIG. 15 shows the PIC for the molecules 1, 6-9. As seen in the figure, the PIC value correlates with molecular weight of the molecules. Evidently, other factors have minor influence; e.g., the SAMs of molecules 6 and 8, showing very similar PIC response, differ in electronic structure, refractive index and light absorption (8 is a chromophore while 6 is not). Since all the molecules consist mainly of carbon and nitrogen (except for the cyclic disulfide group) which have close atomic weights, their molecular weight generally correlates with the size of the molecules, and (assuming again similar surface coverage) with the monolayer thickness. The refractive index of effective media (consisting in this case of the monolayer and surrounding air) depends linearly on the fractional volume of the monolayer and, therefore, on its thickness. Hence, the correlation of the PIC with the molecular weight of an adsorbate is, in fact, correlation with the refractive index of the medium.

Figure 16:
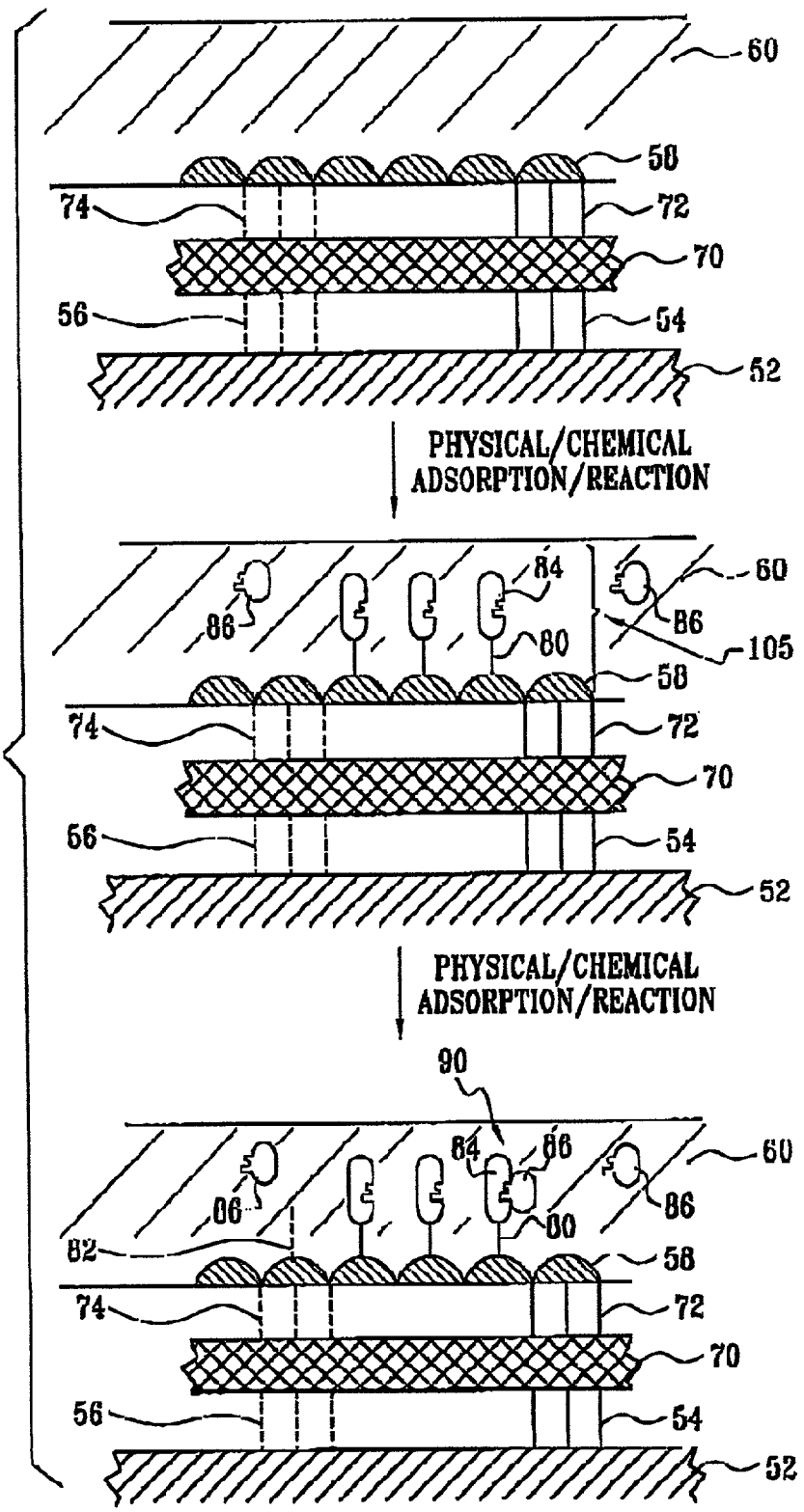
FIG. 16 is a simplified pictorial illustration depicting the application of the system of FIG. 6 to produce a first chemical substance-metallic islands moiety, and then to form a second chemical substance-first chemical substance metallic islands moiety in accordance with a preferred embodiment of the present invention.

Reference is now made to FIG. 16, which is a simplified pictorial illustration depicting the application of the system of FIG. 6 to adsorb a first chemical substance onto the metallic island forming a first chemical substance-metallic islands moiety to which a second chemical substance binds to form a second chemical substance-first chemical substance-metallic islands moiety, in accordance with a preferred embodiment of the present invention.

A first chemical substance 84 is physically/chemically reacted/adsorbed onto system 85 of FIG. 6 so as to form a first chemical substance-metallic islands moiety 105. Chemical substance 84 may be an ion, a small chemical molecule, a biological molecule such as a protein or a nucleic acid. Moiety 105 may be similar to moiety 65 in FIG. 1B, but typically moiety 105 is bound onto intermediate layer 70. Alternatively, there may be no intermediate layer 70. A second chemical substance 86 is then communicated with moiety 105. This may be in a gaseous- and/or liquid-phase medium 60. Substance 86 may react with moiety 105 to form a second chemical substance-first chemical substance-metallic islands moiety 90. Moiety 90 may be, for example, an enzyme-substrate-metallic islands complex, a enzyme-inhibitor-metallic islands complex, an antigen-antibody-metallic islands complex or a DNA-RNA-metallic islands complex.

Figure 17:
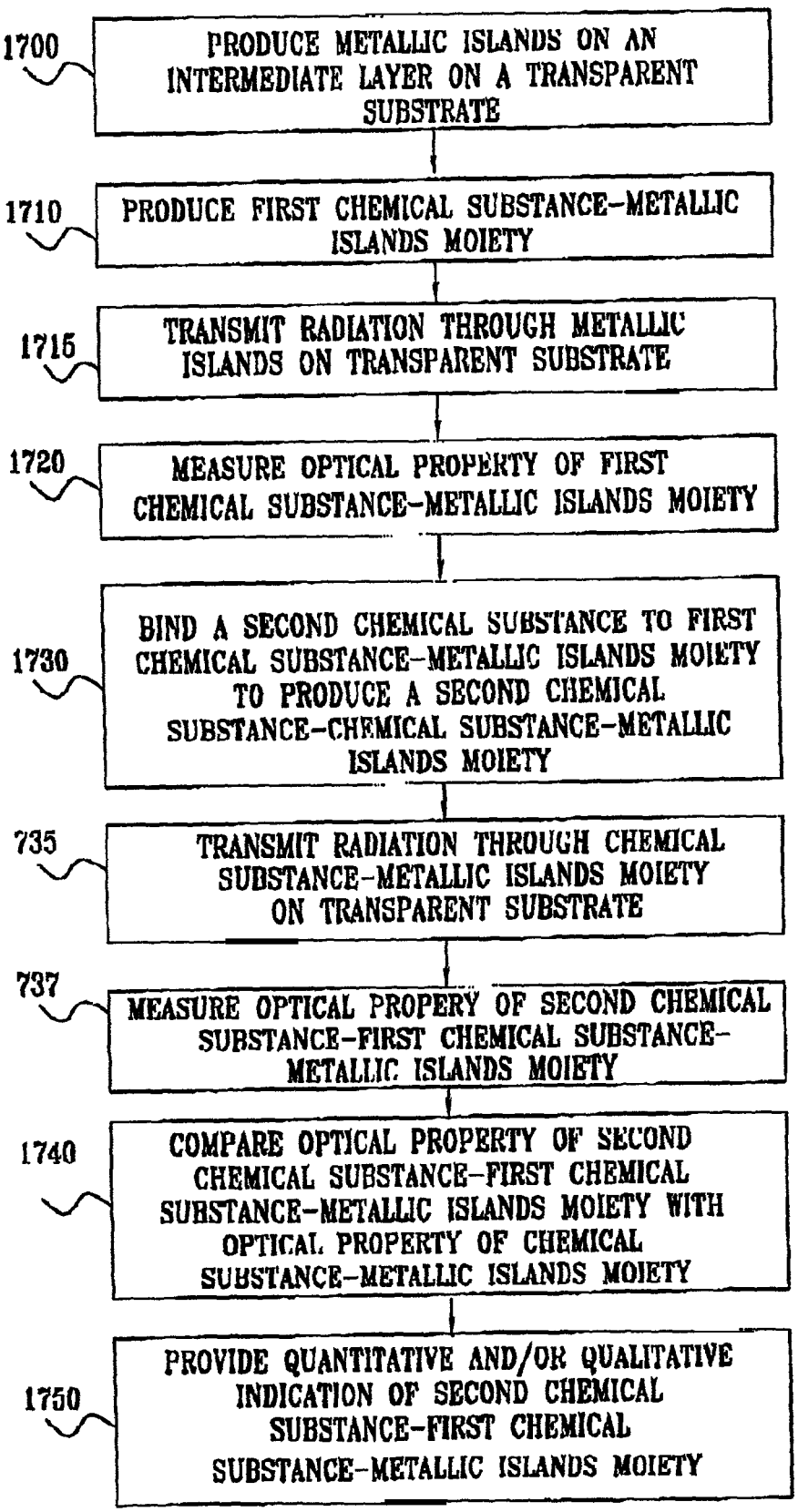
FIG. 17 is a simplified flowchart depicting a method for using a second chemical substance-first chemical substance-metallic islands moiety for detecting or quantifying the second chemical substance, in accordance with a preferred embodiment of the present invention.

Reference is now made to FIG. 17, which is a simplified flowchart depicting a method for using a second chemical substance-first chemical substance-metallic islands moiety for detecting or quantifying the second chemical substance, in accordance with a preferred embodiment of the present invention. This method is exemplified in Examples 2 and 4 hereinbelow.

In a production step 1700 metallic islands are produced on an intermediate layer on a transparent substrate. This step may be substantially similar to step 700 in FIG. 7 and as further described hereinabove and in Example 7 hereinbelow. Alternatively, the metallic islands may be produced directly on the transparent substrate as described in Example 2 hereinbelow.

In a producing step 1710 a first chemical substance-metallic islands moiety is produced. This is exemplified in Examples 2 &4 hereinbelow.

Examples of methods of binding a first chemical substance to a plurality of metallic islands are provided hereinbelow. For example, monolayers of $C_{16}H_{34}H$ and $C_{10}H_{22}S$ were adsorbed by immersion of gold substrates in a 2 mM solution in EtOH.

Monolayers of 1 or 2 were adsorbed by immersion of gold substrates in a 1-10 mM solution in $CHCl_3$ or DMF for 20 min to 15 h. Monolayers of 1-TPPFeCl or 2-TPPFeCl were also adsorbed from 15-18 mM solution of the corresponding complex in $CHCl_3$ or DMF for 5 min to 6 h.

FeTPPCl was bound from 15 mM solutions in $CHCl_3$ for 1 min. CoTPP was bound from $CHCl_3$ solutions. CoPc was bound from THF solutions. The slides were rinsed successively with dry chloroform and absolute ethanol and dried under a stream of purified nitrogen. Physically deposited layers were formed by applying several drops of the substance solutions onto the substrate surface followed by drying under a stream of purified air or nitrogen.

Monolayers of 6-8 were adsorbed by immersion of gold substrates in a 2 mM solution of the corresponding molecule in $CHCl_3$ for various times.

All the monolayers were rinsed successively with dry chloroform (or another solvent used for the adsorption) and absolute ethanol, then dried under a stream of purified air or nitrogen. Physically deposited layers were formed by applying several drops of the substance solutions onto the substrate surface followed by drying under a stream of purified air or nitrogen.

Several molecules based on a cyclic disulfide that binds to gold were chosen for this work (see molecule 1 in FIG. 10A and molecules 6-9 in FIG. 10B. The choice of molecules was based on the observation that thiols sometimes slowly dissolved ultrathin gold films, while the cyclic disulfides did not show this effect.

In a transmission step 1715, system 20 transmits radiation of 300-1100 nm wavelength through the first chemical substance-metallic islands moiety 105 on the transparent substrate 52.

In a measuring step 1720, an optical property of the first chemical substance-metallic islands moiety is measured. The optical property is typically determined after radiation is transmitted through the first chemical substance-metallic islands moiety and a resultant optical property is detected. This is typically performed on a system such as system 20, which may be a spectrophotometer.

Examples of chemical substance-metallic islands moiety 65 include self assembled monolayer (SAMs) of 1. The use of the surface plasmon intensity change (or PIC) for studying self-assembly of molecules that do not absorb light in the UV/visible/IR range is exemplified by monitoring the adsorption kinetics of a monolayer of 1 (which is transparent in the visible region), as shown in FIG. 11A hereinabove.

In a binding step 1730, a chemical reaction and or physical/chemical adsorption process is carried out so as to bind a second chemical substance to first chemical substance-metallic islands moiety to produce second chemical substance-first chemical substance-metallic islands moiety 90. This is exemplified in Examples 2 & 4 hereinbelow. CoTPP may be used as a second chemical substance. The imidazole groups of the molecule may bind CoTPP; since the amount of bound CoTPP correlates with the coverage of the gold by the SAM of 1, direct observation of the adsorption of 1 using the PIC (FIG. 11A) can be confirmed by measurement of the quantity of bound CoTPP (FIG. 11B hereinabove), thus using the CoTPP binding as a "development" tool. As seen in FIG. 11C, plotting both the increase of the gold plasmon absorption (associated with the adsorption of 1) and the Soret band absorption of bound CoTPP vs. adsorption time shows very similar kinetics. Interestingly, the same dependence is observed when plotting the additional enhancement of the gold plasmon resulting from CoTPP binding (FIG. 11C) This correlation demonstrates the potential of this technique for the construction of molecular sensors, since, e.g., here the SAM of 1 may be considered a sensor for CoTPP.

Thus, the gold plasmon adsorption associated with the binding of 1 may be used to provide a concentration of CoTPP bound to 1.

In a transmission step 1735, system 20 transmits radiation of 300-1100 nm wavelength through the second chemical substance-first chemical substance-metallic islands moiety 90 on transparent substrate 52.

In a measuring step 1737, an optical property of the second chemical substance-first chemical substance-metallic islands moiety 90 is measured.

In a comparison step 1740, an optical property of second chemical substance-first chemical substance-metallic islands moiety 90 is compared with the optical property of chemical substance-metallic islands moiety (such as moiety 65 in FIG. 1B). The optical property of the second chemical substance-first chemical substance-metallic islands moiety 90 is typically detected after radiation is transmitted through the second chemical substance-first chemical substance-metallic islands moiety.

In a provision step 1750, an optical property measuring system, such as system 20 of FIG. 1, provides quantitative and/or qualitative indication of second chemical substance-first chemical substance-metallic islands moiety 90.

Additionally or alternatively, system 20 may provide an indication of a quantity of at least one of the second chemical substance, a functionality thereof, the second chemical substance-first chemical substance-metallic islands moiety, a functionality thereof; the first chemical substance-metallic islands moiety, a functionality thereof; the plurality of metallic islands, a functionality thereof, the first chemical substance and a functionality thereof.

The following examples provide further details and practical examples to the figures described hereinabove:

Example 1

Polished quartz slides (Heraeus Amersil, Inc. Duluth, Ga.) were washed with absolute ethanol (GR, Merck, KGaA, Darmstadt, Germany), dried under stream of dry nitrogen (Oxygen Center Ltd., Herzlia, Israel), mounted on a rotation stage and placed in a cryo high vacuum evaporator (Key High Vacuum, Nesconset, N.Y.). A gold island film, 2.5 nm thickness, was evaporated at a rate of 0.01 nm s$^{-1}$ using a resistively heated tungsten boat with gold (99.99%, Holland-Moran, Or-Yehuda, Israel). The evaporation rate and the film thickness were controlled by a thickness monitor (Maxtek TM-100, Maxtek, Inc., Santa Fe Springs, Calif.). The gold coated quartz slides were stored in a desiccator containing silica gel with a moisture indicator (blue gel, Merck, KGaA, Darmstadt, Germany) as desiccant.

Prior to the measurement, the sample (a quartz slide coated with a gold island film as described above) was rinsed with absolute ethanol and dried under an argon stream. Transmission UV-vis spectrum of the sample was measured, using a Jasco V-570 UV/vis/NIR spectrophotometer (Jasco International Co., Ltd., Tokyo, Japan). The scan speed was 100 nm/min. The bandwidth of the light source in the UV/vis region was chosen as 5 nm. A baseline correction procedure was executed prior to each measurement session. In all measurements the reference beam was passed through air.

The sample was then immersed in a 2 mM solution of molecule 8 (FIG. 10B) (propanamide,3,3'-[[(4R,5R)-1,2-dithiane-4,5-diyl]bis(oxy)] bis[N-[3-(1H-imidazol-1-yl)propyl]-,rel-(9CI); CAS#227604-62-8) in CHCl$_3$ (AR, Bio Lab, Ltd., Jerusalem, Israel, passed through a column of activated basic alumina (Alumina B, Akt. 1, ICN Biomedicals, Eschwege, Germany)) for different periods of time, up to 49 min (FIG. 12A-12D). Following immersion the sample was rinsed sequentially with chloroform and ethanol, and dried under an argon stream. A transmission UV-vis spectrum of the sample was then measured.

The molecule 8 (FIG. 10B) possesses a cyclic disulfide for attachment to a gold surface, and two pyrene residues showing three intense absorption bands in the UV region, while in the visible range the molecule is nearly transparent (FIG. 12B, dashed line).

The series of transmission UV/vis absolute (FIG. 12A) and difference (FIG. 12B) spectra of a 2.5 nm Au island film show the changes observed during formation of a monolayer of molecule 8. The self-assembly process (FIG. 12A) is accompanied by an increase of the molecule absorption bands in the UV range, and an increase and a red shift of the Au surface plasmon absorption band around 600 nm. The concurrent development of the pyrene bands and the Au surface plasmon absorption is seen more clearly in the differential plasmon spectroscopy (DPS) presentation (FIG. 12B), obtained by subtracting the background spectrum (0 s in FIG. 12A). As shown in FIG. 12C, the absolute plasmon intensity and position (FIG. 12A) as well as the plasmon intensity change (FIG. 12B) can be used to monitor the binding of the molecule to the Au, showing essentially identical behavior.

FIG. 12D shows a linear relationship with a low standard deviation between the plasmon intensity change and the intensity of the pyrene band, indicating that the intensity change is linearly correlated with the amount of molecules bound to the Au surface. This relationship, not previously shown, forms the basis for application of Au island films as optical sensors using Au surface plasmon absorption measurements in the transmission mode.

Example 2

Mica sheets (SPI Mica, Structural Probe, West Chester, Pa.) were cleaved and mounted on the rotation stage of a cryo high vacuum evaporator (as in Example 1). A gold island film, 2.5 nm thickness, was evaporated using the same parameters as in Example 1. After evaporation the mica sheets coated with the Au island film were placed in a Neytech 85P furnace (Ney, Yucaipa, Calif.), heated to 250 deg C. at a rate of 5 deg/min, annealed at a constant temperature of 250 deg C. for 2.5 hours and then left to cool to room temperature in the furnace. Cleaning and storing of gold coated mica sheets were identical to quartz slides (Example 1).

Self-assembled monolayers (SAMs) of propanamide, 3,3'-[[(4R,5R)-1,2-dithiane-4,5-diyl]bis(oxy)]bis[N-[3-(1H-imidazol-4-yl)propyl]-,rel-(9CI), CAS#227604-63-9 (molecule 1, FIG. 10A) were adsorbed by immersion of the gold coated mica in a solution of 2 mM 1 in CHCl$_3$ for 20 min. After adsorption the samples were rinsed with chloroform and absolute ethanol and dried under a nitrogen stream. Transmission UV-vis spectrum of the samples was measured as described in Example 1.

A gold-coated mica sample was inserted in a 1 mM solution of cobalt (II) tetraphenylporphyrin (CoTPP, Aldrich Chemical Company, Milwaukee, Wis.)) for 1 sec. After removal from the solution, the sample was rinsed with chloroform and absolute ethanol and died under a nitrogen stream. Transmission UV-vis spectrum of the sample was then measured, as described in Example 1. The procedure of dipping the sample in CoTPP solution, rinsing, and measuring the spectrum was repeated several times with the same sample. The overall adsorption time, calculated as sum of all adsorption steps, was 540 sec. The sequence of spectra obtained in this experiment, corrected for the spectrum of the sample before the first dipping in CoTPP solution, is presented in FIG. 8.

Example 3

Gold island films, 2.5 nm thickness, were prepared on quartz slides following the procedure described in Example 1. After evaporation the samples were annealed as described in Example 2.

A gold coated quartz slide was rinsed with chloroform, absolute ethanol and dried under a nitrogen stream. The advancing water contact angle (CA) of a water drop on the gold side of the sample was measured using a goniometer (Rame-Hart NRL Model 100, Rame-Hart, Inc., Mountain Lakes, N.J.) and UV-vis transmission spectrum was recorded according to the procedure described in Example 1.

Adsorption of 1,2-Dithiane-4,5-diol, dipentadecanoate, trans-(molecule 6, FIG. 10B) was performed by dipping the sample in a 2 mM solution of 6 in chloroform. Sequential absorptions were carried out following the procedure described in Example 2. After each adsorption step the CA and UV-vis transmission spectrum were measured. Experimental data showing the change in gold plasmon absorbance and the water CAs after each adsorption step are presented in FIG. 9A, while the correlation between the two parameters is shown in FIG. 9B.

Example 4

Gold island films were prepared on freshly cleaved mica sheets following a procedure identical to that described in Example 2. Cleaning and storing of the gold coated mica sheets were identical to those applied to quartz slides (Example 1).

SAMs of molecule 1 (FIG. 10A) were adsorbed by immersion of the gold coated mica sheets in a solution of 0.4 mM of 1 in $CHCl_3$ for different periods of time, from 1 s to 130 min. Each sample was immersed for a different period of time. After adsorption the samples were rinsed with chloroform and absolute ethanol and dried under a nitrogen stream. Transmission UV-vis spectra of the samples were measured as described in Example 1, and are shown in FIG. 11A.

Each of the gold-coated mica samples with an adsorbed SAM of 1 was then inserted in a 1 mM solution of CoTPP for 10 min. After removal from the solution, each sample was rinsed with chloroform and absolute ethanol and dried under a nitrogen stream. Transmission UV-vis spectrum of the sample was then measured as described in Example 1. Difference spectra of all samples, corrected for the spectrum of the sample with a SAM of 1 (no CoTPP), are presented in FIG. 11B. The correlation between the increase in the absorbance of the Soret band of CoTPP and the change in the gold surface plasmon intensity is shown in FIG. 10C.

Example 5

Gold island films (nominal thickness: 5 nm) were prepared on freshly cleaved mica sheets following the procedure in Example 2, skipping the annealing step after evaporation. Cleaning and storing of the gold coated mica sheets were identical to those applied to quartz slides (Example 1).

A gold coated mica sample was mounted in a 1 cm optical pass spectrophotometric quartz cuvette (Aldrich Chemical Company, Milwaukee, Wis.) isolated from the ambient by a teflon cap. The cuvette was filled with 2 ml of 2,2,2-trifluoroethanol (Sigma Chemical Company, St. Louis, Mo.). A UV-vis spectrum was then recorded following the procedure in Example 1, and the position of the maximum absorption of the gold surface plasmon band was determined as 720 nm.

4.1 µL of 1-decanethiol ($C_{10}H_{22}S$, Aldrich Chemical Company, Milwaukee, Wis.), corresponding to a concentration of 2 mM in the solution, were injected into the solution in the cell. Following the injection, formation of a SAM of 1-decanethiol on the gold island film was monitored by continuous measurement of the absorbance at a constant wavelength of 720 nm.

The kinetics, i.e., the change of absorbance vs. time as a result of formation of a monolayer of 1-decanethiol, are presented in FIG. 13A.

Example 6

A gold island film was prepared on freshly cleaved mica as described in Example 5. Cleaning and storing of the gold coated mica sheets were identical to those applied to quartz slides (Example 1).

A gold coated mica sample was mounted in a 1 cm optical pass spectrophotometric quartz cuvette isolated from the ambient by a teflon cap. A UV-vis spectrum was then recorded following the procedure in Example 1, and the position of the maximum absorption of the gold surface plasmon band was determined as 720 nm.

A small drop of liquid 1-decanethiol ($C_{10}H_{22}S$, Aldrich Chemical Company, Milwaukee, Wis.) was placed in the cuvette using a syringe. Formation of a SAM of 1-decanethiol in air was monitored by continuous measurement of the absorbance at a constant wavelength of 720 nm. The kinetics, i.e., the change of absorbance vs. time as a result of formation of a monolayer of 1-decanethiol, are presented in FIG. 13B.

Example 7

The experimental procedure was identical to that described in Example 6.

Formation of a physically adsorbed layer of benzene ($C_6H_6$, Aldrich Chemical Company, Milwaukee, Wis.) in air was monitored by continuous measurement of the absorbance at a constant wavelength of 720 nm, after placing a drop of benzene in the cuvette.

The kinetics, i.e., the change of absorbance vs. time as a result of formation of a monolayer of benzene, are presented in FIG. 14A.

Example 8

Polystyrene Petri dishes (90×12 mm, Miniplast Ein-Shemer, Ein-Shemer, Israel) were cut with a hot knife into slides of 1×2 cm. The slides were rinsed with absolute ethanol, dried under a nitrogen stream and mounted on the rotation stage of the metal evaporator described in Example 1. A gold island film, 1.5 nm thickness, was deposited by evaporation onto the slides as described in Example 1, at a deposition rate of 0.01 nm/s. After evaporation the slides were dipped 12 hours in triply distilled water.

UV-vis transmission spectra of the samples were then measured using a spectrophotometer (Cary 50, Varian Australia Pty Ltd., Mulgrave, Australia). The measurement was carried out in the baseline correction mode, with the baseline recorded at the beginning of each session. Data acquisition was performed at 0.5 sec/point, at 1 nm resolution. Each slide was rinsed with absolute ethanol and dried under a nitrogen stream before each spectral measurement.

Figure 18:
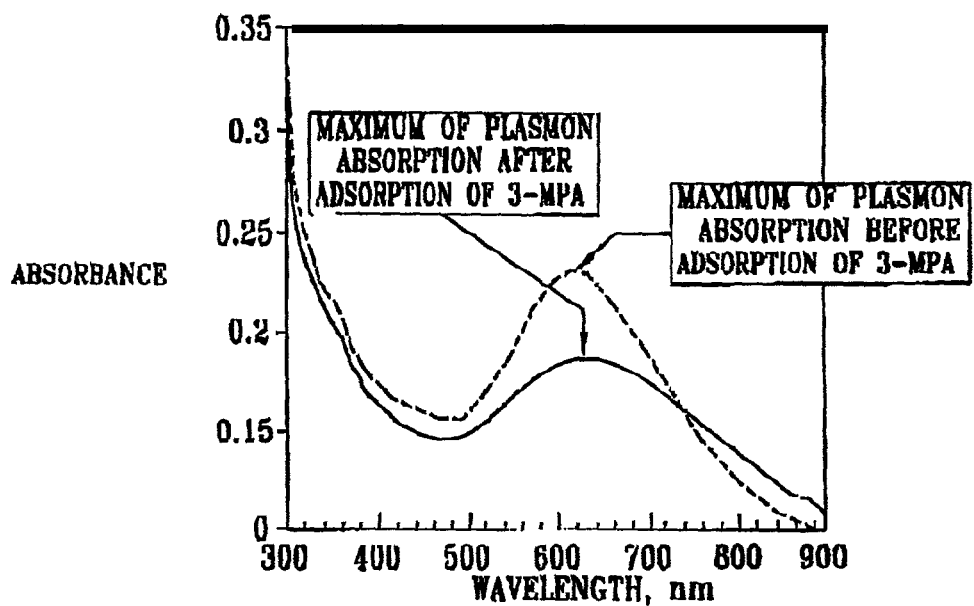
FIG. 18 is a graph of absorbance of a gold island film on polystyrene before (dashed line) and after (solid line) adsorption of a monolayer of 3-mercaptopropionic acid (3-MPA), in accordance with a preferred embodiment of the present invention.

Reference is now made to FIG. 18, which is a graph of absorbance of a gold island film on polystyrene before (dashed line) and after (solid line) adsorption of a monolayer of 3-mercaptopropionic acid (3-MPA), in accordance with a preferred embodiment of the present invention. Film thickness: 1.5 nm. The monolayer was adsorbed by dipping the sample in a 10 mM aqueous solution of 3-MPA for two hours.

The spectrum of a polystyrene slide coated with a gold island film and treated by dipping in water is shown in FIG. 18 (dashed line). Following the measurement the slide was dipped in 10 mM aqueous solution of 3-mercaptopropionic acid (3-MPA, for synthesis, MerckKGaA, Darmstadt, Germany) for two hours. The spectrum of the sample after adsorption of 3-MPA is shown in FIG. 18 (solid line), showing that the intensity of the gold surface plasmon decreased as a result of 3-MPA adsorption.

Example 9

Microscope cover glass slides, 22×22 mm, No. 1 (Paul Marienfeld GmbH & Co. KG, Lauda-Koenigshofen, Germany) were cut with a diamond pen to a size of ca. 10×20 mm. The slides were rinsed with absolute ethanol and dried under a nitrogen stream. The slides then underwent three times the following procedure: insertion into a boiling/refluxed mixture of 7 ml $H_2O$+6.74 ml 3-(mercaptopropyl)trimetoxysilane, 95% (Aldrich Chemical Company, Inc., Milwaukee, Wis.)+359 ml 2-propanol (AR, Bio Lab, Ltd., Jerusalem, Israel) for 10 min; washing with copious amount of 2-propanol; drying under a nitrogen stream; 8 min in a vacuum oven (Tuttnauer, Jerusalem, Israel) at 100-107 deg C.

The experimental procedure applied to the glass slides pretreated by the above method was identical to the one applied to polystyrene slides (Example 8).

Figure 19:
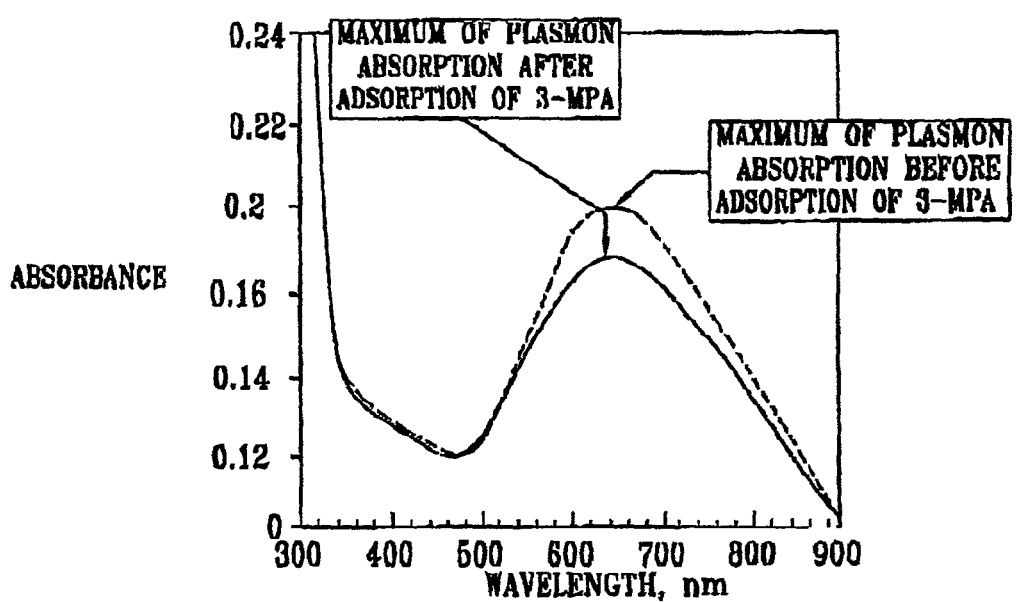
FIG. 19. is a graph of absorbance of a gold island film on a pretreated glass slide before (dashed line) and after (solid line) adsorption of monolayer of 3-mercaptopropionic acid, in accordance with a preferred embodiment of the present invention.

Reference is now made to FIG. 19, which is a graph of absorbance of a gold island film on a pretreated glass slide before (dashed line) and after (solid line) adsorption of monolayer of 3-mercaptopropionic acid (3-MPA), in accordance with a preferred embodiment of the present invention. The monolayer was adsorbed by dipping the sample in a 10 mM aqueous solution of 3-MPA for two hours.

The spectrum of a gold coated glass sample before (dashed line) and after (solid line) formation of a monolayer of 3-MPA is shown in FIG. 19, showing that the intensity of the gold surface plasmon decreased as a result of 3-MPA adsorption.

It may be concluded that use of ultrathin gold island films on transparent substrates and measurement of changes in the Au surface plasmon absorption in transmission UV/vis spectroscopy, provide a novel scheme for quantitative determination of molecular binding to Au surfaces. The method is widely applicable, sub-monolayer sensitive and exceedingly simple, requiring just a conventional spectrophotometer. A linear relationship was shown between the plasmon intensity change and the Au surface coverage, suggesting possible use of the system in sensing applications. Compared with related techniques, the present method does not require complicated and expensive instrumentation (as in surface plasmon resonance spectroscopy, SPR) or relatively complex sample preparation (as in colloid films). The method is widely applicable to different chemical and biological molecules, as any binding to the Au surface produces change in the plasmon absorption. Selectivity may be induced by applying a selective layer on the Au film and following molecular binding to the layer. This was shown here by monitoring the binding of a metalloporphyrin to an Au island film pre-coated with a self-assembled monolayer which binds metallo-macrocycle molecules. Application of the method to a wide range of chemical and biological sensors may be envisioned.

It is appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination.

It will be appreciated by persons skilled in the art that the present invention is not limited to what has been particularly shown and described hereinabove. Rather, the scope of the present invention is defined only by the claims that follow.

The invention claimed is:

1. An analytical method comprising:
transmitting electromagnetic radiation through a first structure comprising a substantially transparent substrate carrying a plurality of metallic islands;
detecting the electromagnetic radiation transmitted through the first structure at an opposite side of the substrate from which the electromagnetic radiation was applied to generate a first measurement corresponding to a first surface plasmon intensity of the first structure;
forming a second structure by contacting the first structure by a substance;
transmitting electromagnetic radiation through the second structure, and
detecting the electromagnetic radiation transmitted through the second structure at the opposite side of the substrate from which the electromagnetic radiation was applied,
to generate a second measurement corresponding to a second surface plasmon intensity of the second structure; and
sensing a presence or absence of binding of the substance to the first structure by utilizing the first and the second measurements to determine a change of intensity between the second surface plasmon intensity and the first surface plasmon intensity.

2. The method of claim 1, wherein the first structure further comprises an intermediate layer bound to the metallic islands.

3. The method of claim 1, wherein the metallic islands are made of Au or Ag.

4. The method of claim 1, wherein the electromagnetic radiation is in the UV, infrared or visible spectrum.

5. The method of claim 1, wherein the substance is a chemical substance.

6. The method of claim 1, wherein the substance is a biological substance.

7. An analytical method comprising:
transmitting electromagnetic radiation through a first structure comprising a substantially transparent substrate, a plurality of metallic islands deposited onto the transparent structure, and a layer deposited onto the metallic islands;
detecting the electromagnetic radiation transmitted through the first structure at an opposite side of the substrate from which the electromagnetic radiation was applied, to generate a first measurement corresponding to a first surface plasmon intensity of the first structure;
forming a second structure by contacting the first structure by a substance;
transmitting electromagnetic radiation through the second structure, and
detecting the electromagnetic radiation transmitted through the second structure at the opposite side of the substrate from which the electromagnetic radiation was applied,
to generate a second measurement corresponding to a second surface plasmon intensity of the second structure; and
sensing a presence or absence of binding of the substance to the layer of the first structure by utilizing the first and the second measurements to determine a change of intensity between the second surface plasmon intensity and the first surface plasmon intensity.

8. The method of claim 7, wherein the layer is characterized by specific affinity to a ligand in the substance.

9. The method of claim 7, wherein the substance is in a liquid form.

10. The method of claim 7, wherein the substance is in a gaseous form.

11. The method of claim 7, wherein sensing the presence or absence of binding of the substance to the layer comprises contacting the first structure by a solution containing the substance.

12. The method of claim 7, wherein the first surface plasmon intensity and the second surface plasmon intensity are measured in the transmitted electromagnetic radiation of a single wavelength $\lambda$.

13. An analytical method comprising:
transmitting electromagnetic radiation through a first structure comprising a substantially transparent substrate, a plurality of metallic islands deposited onto the transparent structure, and a layer deposited onto the metallic islands;

detecting the electromagnetic radiation transmitted through the first structure at an opposite side of the substrate from which the electromagnetic radiation was applied, to generate a first measurement corresponding to a first surface plasmon intensity of the first structure;

forming a second structure by contacting the first structure by a phase comprising an analyte;

transmitting electromagnetic radiation through the second structure, and detecting the electromagnetic radiation transmitted through the second structure at the opposite side of the substrate from which the electromagnetic radiation was applied, to generate a second measurement corresponding to a second surface plasmon intensity of the second structure; and determining a concentration of the analyte in the phase by quantitatively monitoring binding of the analyte to the layer of the first structure by utilizing the first and the second measurements to determine a change of intensity between the second surface plasmon intensity and the first surface plasmon intensity.

14. The method of claim 13, further comprising utilizing determining the concentration of the analyte to monitor kinetics of a chemical reaction.

15. The method of claim 13, wherein the analyte comprises chemical of biological molecules.

16. The method of claim 13, wherein the metallic islands are made of Au or Ag.

17. The method of claim 13, wherein the electromagnetic radiation is in the UV, infrared or visible spectrum.

18. The method of claim 13, wherein the first surface plasmon intensity and the second surface plasmon intensity are measured in the transmitted electromagnetic radiation of a single wavelength $\lambda$.

19. The method of claim 13, wherein the concentration of the analyte in the phase linearly correlates with the change of intensity between the second surface plasmon intensity and the first surface plasmon intensity.

20. A sensing system comprising:
a sensor comprising a first structure comprising a substantially transparent substrate, a plurality of metallic islands deposited onto the transparent substrate, and a layer deposited onto the metallic islands;
a source for generating electromagnetic radiation at a first side of the sensor; an adsorption enabling element serving to bring an analyte in contact with the sensor;
a detector for detecting a spectral change in the electromagnetic radiation transmitted through the sensor at an opposite side of the sensor, the spectral change in the transmitted electromagnetic radiation correlating with a change in a localized surface plasmon intensity in the metallic islands, the change in the localized surface plasmon intensity occurring due to adsorption or desorption of the analyte onto the layer deposited onto the metallic islands.

21. The system of claim 20, further comprising a processor coupled to the detector, the processor serving to receive data from the detector and perform qualitative and/or quantitative sensing of the absorption or desorption of the analyte.

22. The system of claim 20, wherein the analyte is a chemical substance or a biological substance.

23. The system of claim 20, wherein the adsorption enabling element further comprises a flow cell for contacting the sensor by the analyte.

24. The system of claim 20, wherein the electromagnetic radiation is UV, infrared or visible radiation.

25. The system of claim 20, wherein the plurality of metallic islands comprises metallic films of a thickness not exceeding 10 nm.

26. The system of claim 20, wherein the metallic films are made of Au or Ag.

27. The system of claim 20, wherein the analyte is in a liquid or gaseous phase.

28. A kit for analysis comprising: a sensor comprising a substantially transparent substrate, a plurality of metallic islands deposited onto the transparent substrate, and a binding layer deposited onto the metallic islands;
a source for generating electromagnetic radiation at a first side of the sensor; an adsorption enabling element serving to bring a phase in contact with the binding layer;
a detector for detecting a spectral change in the electromagnetic radiation transmitted through the sensor at an opposite side of the sensor, the spectral change in the transmitted electromagnetic radiation correlating with a change in a localized surface plasmon intensity in the metallic islands, the change in the localized surface plasmon intensity occurring due to binding of an analyte having specific affinity to the binding layer; and
means for providing qualitative or quantitative information about the presence or absence of the analyte in the phase.

29. The kit of claim 28, wherein the phase can be liquid or gaseous.

30. The kit of claim 28, further comprising a processor coupled to the detector and to the means for providing, the processor serving to receive data from the detector and perform qualitative and/or quantitative sensing of binding of the analyte.

31. The kit of claim 28, wherein the information about the presence or absence of the analyte in the phase comprises information about a concentration of the analyte, kinetics of a chemical reaction involving the analyte.

32. The system of claim 28, wherein the analyte is a chemical substance or a biological substance.

33. The system of claim 28, wherein the adsorption enabling element further comprises a flow cell for contacting the sensor by the phase.

34. The system of claim 28, wherein the electromagnetic radiation is UV, infrared or visible radiation.

35. The system of claim 28, wherein the plurality of metallic islands comprises metallic films of a thickness not exceeding 10 nm.

36. The system of claim 28, wherein the metallic films are made of Au or Ag.

* * * * *